US011390863B2

(12) United States Patent
Beekwilder et al.

(10) Patent No.: US 11,390,863 B2
(45) Date of Patent: Jul. 19, 2022

(54) SANTALENE SYNTHASE

(71) Applicant: ISOBIONICS B.V., Geleen (NL)

(72) Inventors: Martinus Julius Beekwilder, Renkum (NL); Adèle Margaretha Maria Liduina Van Houwelingen, Wekerom (NL); Hendrik Jan Bosch, Wageningen (NL); Georg Friedrich Lentzen, Geleen (NL); Elena Melillo, Geleen (NL); Hendrik Wouter Wisselink, Culemborg (NL)

(73) Assignee: ISOBIONICS B.V., Geleen (NL)

( * ) Notice: Subject to any disclaimer, the term of this patent is extended or adjusted under 35 U.S.C. 154(b) by 152 days.

(21) Appl. No.: 16/490,107

(22) PCT Filed: Mar. 2, 2018

(86) PCT No.: PCT/NL2018/050130
§ 371 (c)(1),
(2) Date: Aug. 30, 2019

(87) PCT Pub. No.: WO2018/160066
PCT Pub. Date: Sep. 7, 2018

(65) Prior Publication Data

US 2020/0010822 A1 Jan. 9, 2020

(30) Foreign Application Priority Data

Mar. 2, 2017 (NL) ..................................... 2018457

(51) Int. Cl.

| | |
|---|---|
| ***C12N 15/82*** | (2006.01) |
| ***C12N 9/88*** | (2006.01) |
| ***C07K 16/40*** | (2006.01) |
| ***C12P 5/00*** | (2006.01) |
| ***C12P 7/02*** | (2006.01) |
| ***C12N 15/80*** | (2006.01) |

(52) U.S. Cl.
CPC ................ *C12N 9/88* (2013.01); *C07K 16/40* (2013.01); *C12N 15/80* (2013.01); *C12N 15/8242* (2013.01); *C12P 5/002* (2013.01); *C12P 7/02* (2013.01); *C12Y 402/03083* (2013.01)

(58) Field of Classification Search
CPC ............................................ C12Y 402/03082
See application file for complete search history.

(56) References Cited

FOREIGN PATENT DOCUMENTS

| | | |
|---|---|---|
| WO | 2011/000026 | 1/2011 |
| WO | 2015/153501 | 10/2015 |
| WO | 2016/064347 | 4/2016 |

OTHER PUBLICATIONS

Di Girolamo et al Archives of Biochemistry and Biophysics vol. 695 Publication 108647, 12 pages (Year: 2020).*

Stubbs et al Journal of Essential Oil Research vol. 16 pp. 9-14 (Year: 2004).*

International Search Report for PCT/NL2018/050130, dated Jun. 21, 2018, 5 pages.

Written Opinion of the ISA for PCT/NL2018/050130, dated Jun. 21, 2018, 6 pages.

Jones et al., "Sandalwood Fragrance Biosynthesis Involves Sesquiterpene Synthases of Both the Terpene Synthase (TPS)-a and TPS-b Subfamilies, including Santalene Synthases", Journal of Biological Chemistry, vol. 286, No. 20, pp. 17445-17454, May 2011.

* cited by examiner

*Primary Examiner* — David H Kruse

(74) *Attorney, Agent, or Firm* — Faegre Drinker Biddle & Reath LLP

(57) ABSTRACT

The invention is directed to a santalene synthase, to a nucleic acid encoding said santalene synthase, to an expression vector comprising said nucleic acid, to a host cell comprising said expression vector, to a method of preparing santalene, to a method of preparing santalol and to a method of preparing a santalene synthase. The invention is further directed to an antibody specific for the santalane synthase.

21 Claims, 11 Drawing Sheets

Figure 1:
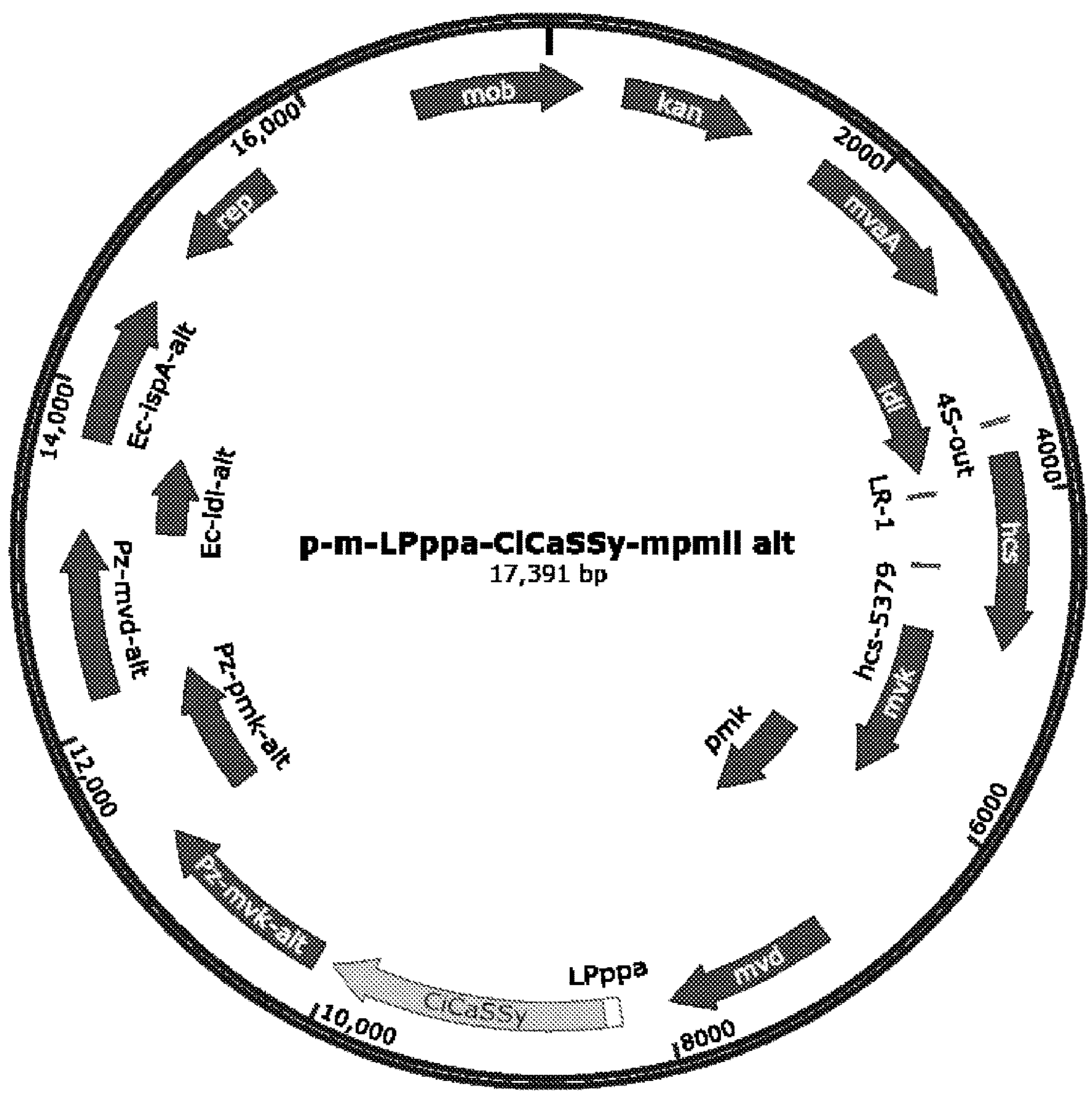

Specification includes a Sequence Listing.

```
TS23-3    MDSMEVRRSAIYHSTFWDIDSIRALLARRDCTAAAALSHDHHKRLKERIQRRLQDITQPH
TS23-1    MDSMEVRRSANYHSTFWDIDSIRALLARRDCTVAAALSHDHHKRLKERIQRRLQDITQPH
TS23-2    MDSMEVRRSANYHSTFWDIDSIRALLARRDCTVAAALSHDHHKRLKERIQRRLQDITQPH
          ********** *********************.***************************

TS23-3    HLLGLIDAVQRLGVAYQFEEEISDALHGLHSENTEHAIKDSLHHTSLYFRLLRQHGCNLS
TS23-1    HLLGLIDAVQRLGVAYQFEEEISDALHGLHSENTEHAIKDSLHHTSLYFRLLRQHGCNLS
TS23-2    HLLGLIDAVQRLGVAYQFEEEISDALHGLHSENTEHAVKDSLHHTSLYFRLLRQHGCNLS
          *************************************:**********************

TS23-3    SDIFNKFKKEGGGFKASLCEDAMGLLSLYEAVRLSVKGEAILEEAQVFSIANLKILMERV
TS23-1    SDIFNKFKKEGGGFKASLCEDAMGLLSLYEAAHLGVKSEAILEEAQVFSTSNLKILMERV
TS23-2    TDIFNKFKKEGGGFKASLCEDAMGLLSLYEAAHLGVKSEAILEEAQVFSTSNLKILMERV
          :******************************.:*.**.*********** :*********

TS23-3    ERKLADRIEHALEIPLYWRAPRLEARWYIDVYEKEDGRIDDLLDFAKLDFNRVQMLYQTE
TS23-1    ERKLADRIDHALEIPLYWRAPRVEARWYIDVYEKEDGRIDDLLDFAKLDFNRVQMLYQTE
TS23-2    ERKLADRIDHALEIPLYWRAPRVEARWYIDVYEKEDGRIDDLLDFAKLDFNRVQMLYQTE
          ********:*************:*************************************

TS23-3    LKELSMWWELLGLPAKMGFFRDRLLENHLFSIAVVVEPQYSQCRVAITKAIVLMTAMDDF
TS23-1    LKELSMWWELLGLPEKMGFFRDRLLESHLFSIGVVVEPQYSQCRVAITKALVLFTAMDDF
TS23-2    LKELSMWWELLGLPEKMGFFRDRLLESHLFSIGVVVEPQYSQCRVAITKALVLFTAMDDF
          ************** ***********.*****.*****************:**:******

TS23-3    YDVHGLPDELKVFTDTVNRWDLEGIDQLPEYMKLYYLALYNTTNETAYIILKEKGFNATH
TS23-1    YDVHGLPEELKVFTDTVNRWDLEGIDQLPEYMKLYYLALYNTTNETAYIILKEKGFNATH
TS23-2    YDVHGLPEELKVFTDTVNRWDLEGIDQLPEYMKLYYLALYNTTNETAYIILKEKGFNATH
          *******:****************************************************

TS23-3    YLKKLWAMQSNAYFREAQWFNSGYIPKFDEYLDNALVSVGAPFVLGLSYPMIQQQISKEE
TS23-1    YLKKLWAMQSNSYFREAQWFNSGYIPKFDEYLDNALVSVGVPLLLGLSYPMIQQHISKAE
TS23-2    YLKKLWAMQSNSYFREAQWFNSGYIPKFDEYLDNALVSVGVPLLLGLSYPMIQQHISKAE
          ***********:****************************.*::**********:*** *

TS23-3    IDLIPEDLNLLRWASIIFRLYDDLATSKAEQQRGDVPKSIQCYMHETGSSEEVAANHIRD
TS23-1    IDLIPEDLNLLRWASIIFRLYNDLATSKAEQQRGDVPKSIQCYMHETGSSEEVAANHIRD
TS23-2    IDLIPEDLNLLRWASIIFRLYNDLATSKAEQQRGDVPKSIQCYMHETGSSEEVAANHIRD
          *********************:**************************************

TS23-3    LISDAWKEVNAECLKPTSLSKHYVGVAPNSARSGVLMYHHDFDGFASPHGRTNAHITSIF
TS23-1    LISDAWKELNAECLKPTSLSKHYVGVAPNSARSGVLMYHHDFDGFASPHSRTNAHITSIF
TS23-2    LISDAWKEVNAECLKPTSLSKHYVGVAPNSARSGVLMYHHDFDGFASPHSRTNAHITSIF
          ********:****************************************.**********

TS23-3    FEPVPLKESINLG
TS23-1    FEPVPLKESINLG
TS23-2    FEPVPLKESINLG
          *************
```

Figure 7 pACYCDuet rt12.708 tetradecane pACYCDuet_TS23-1 rt12.708 tetradecane pACYCDuet_TS23-3(=CicaSSy)

| | |
|---|---|
| rt12.708 | tetradecane |
| rt13.046 | α-santalene |
| rt13.213 | trans-α-bergamotene |
| rt13.564 | β-santalene |

pACYCDuet_SaSSy

| | |
|---|---|
| rt12.708 | tetradecane |
| rt13.064 | α-santalene |
| rt13.213 | trans-α-bergamotene |
| rt13.560 | β-santalene |

SANTALENE SYNTHASE

This application is the U.S. national phase of International Application No. PCT/NL2018/050130 filed 2 Mar. 2018, which designated the U.S. and claims priority to NL Patent Application No. 2018457 filed 2 Mar. 2017, the entire contents of each of which are hereby incorporated by reference.

The invention is directed to a santalene synthase, to a nucleic acid encoding said santalene synthase, to an expression vector comprising said nucleic acid, to a host cell comprising said expression vector, to a method of preparing santalene, to a method of preparing santalol and to a method of preparing a santalene synthase.

Many organisms have the capacity to produce a wide array of terpenes and terpenoids. Terpenes are actually or conceptually built up from 2-methylbutane residues, usually referred to as units of isoprene, which has the molecular formula $C_5H_8$. One can consider the isoprene unit as one of nature's common building blocks. The basic molecular formulae of terpenes are multiples of that formula: $(C_5H_8)_n$, wherein n is the number of linked isoprene units. This is called the isoprene rule, as a result of which terpenes are also denoted as isoprenoids. The isoprene units may be linked together "head to tail" to form linear chains or they may be arranged to form rings. In their biosynthesis, terpenes are formed from the universal 5 carbon precursors isopentenyl diphosphate (IPP) and its isomer, dimethylallyl diphosphate (DMAPP). Accordingly, a terpene carbon skeleton generally comprises a multiple of 5 carbon atoms. Most common are the 5-, 10-, 15-, 20-, 30- and 40-carbon terpenes, which are referred to as hemi-, mono-, sesqui-, di-, tri- and tetraterpenes, respectively. Besides "head-to-tail" connections, tri- and tetraterpenes also contain one "tail-to-tail" connection in their centre. The terpenes may comprise further functional groups, like alcohols and their glycosides, ethers, aldehydes, ketones, carboxylic acids and esters. These functionalised terpenes are herein referred to as terpenoids. Like terpenes, terpenoids generally have a carbon skeleton having a multiple of 5 carbon atoms. It should be noted that the total number of carbons in a terpenoid does not need to be a multiple of 5, e.g. the functional group may be an ester group comprising an alkyl radical having any number of carbon atoms.

Apart from the definitions given above, it is important to note that the terms "terpene", "terpenoid" and "isoprenoid" are frequently used interchangeably in open as well as patent literature.

Santalene is a naturally occurring sesquiterpene, produced in specific plants, such as the sandalwood tree. Santalene, and especially 8-santalene is useful as a starting material for the chemical synthesis or the biosynthesis of santalol and in particular for β-santalol, which is a major constituent of sandalwood oil. Sandalwood oil is an important perfumery ingredient obtained by steam distillation of the heartwood of various species of the sandalwood (*Santalum*) tree, e.g *Santalum album* and *Santalum spicatum*. Sandalwood oil is used in perfumes, cosmetics, and for flavouring. Sandalwood oil contains more than 90% sesquiterpene alcohols of which 40-60% is the α-santalol, whilst β-santalol comprises 15-25%. Whilst other constituents such as α-santalol, epi-β-santalol and bergamotol may also contribute to the typical sandalwood oil sensory profile, β-santalol is considered as the most important odour-defining molecule in sandalwood oil. The exact composition of the oil depends on the *Santalum* species, the harvest conditions and the distillation process employed.

Sandalwood trees have been over-exploited to produce sandalwood and sandalwood oil over a long period, leading to the threatened status of several sandalwood species (Teixeira da Silva et al., 2016). Consequently, the supply of sandalwood oil has decreased significantly over the past years. It is therefore desirable to provide an alternative source of sandalwood oil terpenes, and especially the α- and β-santalols which are the key molecules in defining the sweet, warm and woody odour of sandalwood oil (Baldovini et al., 2011) (Diaz-Chavez et al., 2013).

It has been proposed to prepare santalene (or santalol) microbiologically, making use of micro-organisms genetically modified by incorporation of a gene that is coding for a protein having santalene synthase activity. A santalene synthase can be used for the preparation of santalene from FPP, a conversion which might be executed as an isolated reaction (in vitro) or as part of a longer metabolic pathway eventually leading to the production of santalene from sugar (in vivo).

WO/2010/067309 describes a method for producing β-santalene using a santalene synthase from *Santalum* (Schalk. 2014). U.S. Pat. No. 8,993,284, WO201100026 and Jones et al. (2011) describe terpene synthases from three different *Santalum* species (*Santalum album, S. austrocaledonicum*, and *S. spicatum*) producing ct-santalene, α-trans-bergamotene, epi-β-santalene and β-santalene concurrently (Zulak et al., 2016). WO2015153501 describes modified santalene synthase enzymes derived from the *S. album* santalene synthase with increased terpene synthase activity when compared to the native *S. album* santalene synthase. WO2012/110375 describes a synthesis route for an intermediate that can be used for the chemical synthsis of beta-santalol.

The only terpene synthases known to form α-santalene, β-santalene, epi-β-santalene, and bergamotene have so far been identified in the genus *Santalum*. Other plants have however been described to produce some of the santalol-type sesquiterpenoids: WO2006/134523 describes a terpene synthase capable of synthesizising sesquiterpenes with a santalene backbone, like epi-β-santalene and trans-α-bergamotene, but no production of β-santalene and α-santalene is described (SCHALK, 2006). Epi-β-santalene cannot be used for the synthesis of the desired β-santalol. WO2009/109597 describes another terpene synthase capable of producing terpenes of the santalene type (Schalk, 2016). However, the described synthase does produce α-santalene from E,E-farnesyl pyrophosphate, but no β-santalene. WO 2008/142318 describes an α-santalene synthase from *Solanum habrochailes*. This enzyme uses Z,Z-farnesyl pyrophosphate as a sbubstrate to produce α-santalene. Again, the described synthase produces only α-santalene and no β-santalene. Essential oils derived from hydrodistillation of leafs, stem and bark of the camphor tree, *Cinnamomum camphora* have been described to contain santalene-type terpenes, namely α-santalene, cis-α-bergamotene, epi-beta-santalene and beta-santalene (Pelissier & Bessiere, 1995), but no corresponding terpene synthases have been identified.

The currently known santalene synthases have a number of distinct drawbacks which are in particular undesirable when they are applied in an industrial santalene production process wherein santalene (or santalol and in particular β-santalol) is prepared from FPP, either in an isolated reaction (in vitro), e.g. using an isolated santalene synthase or (permeabilized) whole cells, or otherwise, e.g. in a fermentative process being part of a longer metabolic pathway eventually leading to the production of β-santalol from sugar (in vivo).

Thus, there is a need for an alternative santalene synthase which may be used in the preparation of santalene, in particular β-santalene and/or β-santalol. In particular there is a need for an alternative santalene synthase that displays an improved expression, at least in selected host cells; an alternative santalene synthase that has a high enzymatic activity at least under specific conditions, such as at a neutral or alkaline pH and/or intracellularly in the cell wherein it has been produced: and/or an alternative santalene synthase that is highly specific, in particular that has improved specificity compared to santalene synthase from *Santalum album*, with respect to catalysing the conversion of FPP into β-santalene, at least under specific conditions, such as at about neutral or at alkaline pH and/or intracellularly in the cell wherein it has been produced.

It has been found that a specific polypeptide that was hitherto unknown has santalene synthase activity and that this polypeptide can be used as a catalyst that may serve as an alternative to known santalene synthases.

Accordingly, the present invention relates to a santalene synthase comprising an amino acid sequence as shown in SEQ ID NO: 3, or a functional homologue thereof, said functional homologue being a santalene synthase comprising an amino acid sequence which has a sequence identity of at least 60% with SEQ ID NO: 3. Said homologue may in particular be a santalene synthase comprising an amino acid sequence which has a sequence identity of at least 65%, at least 70%, at least 75%, at least 80%, at least 85%, at least 90%, at least 95%, at least 98% or at least 99% with SEQ ID NO: 3.

Further, the invention relates to an antibody having binding affinity to a santalene synthase according to the invention. An antibody according to the invention thus specifically binds to a santalene synthase according to the invention.

The antibody, which may either be monoclonal or polyclonal, may be produced by methods known in the art, e.g. as described by Hudson et al., Practical Immunology, Third Edition (1989), Blackwell Scientific Publications.

The invention further relates to a nucleic acid, comprising a nucleic acid sequence encoding a santalene synthase according to the invention, or comprising a nucleic acid sequence complementary to said encoding sequence. In particular, the nucleic acid may be selected from nucleic acids comprising a nucleic acid sequence as shown in SEQ ID NO: 1 or SEQ ID NO: 2, and other nucleic acid sequences encoding a santalene synthase according to the invention, said other sequences comprising a nucleic acid sequence having a sequence identity of at least 60%, in particular of at least 65%, at least 70%, at least 80%, at least 85%, at least 90%, at least 95%, at least 98% or at least 99% with the nucleic acid sequence shown in SEQ ID NO: 1 or SEQ ID NO: 2, or respectively nucleic acids complementary thereto. Said other nucleic acid sequence encoding a santalene synthase according to the invention may herein after be referred to as a functional analogue.

A santalene synthase or nucleic acid according to the invention may be a natural compound or fragment of a compound isolated from its natural source (e.g. *Cinnamomum camphora*), be a chemically or enzymatically synthesised compound or fragment of a compound or a compound or fragment of a compound produced in a recombinant cell, in which recombinant cell it may be present or from which cell it may have been isolated.

The invention further relates to an expression vector comprising a nucleic acid according to the invention.

The invention further relates to a host cell, which may be an organism per se or part of a multi-cellular organism, comprising an expression vector comprising a nucleic acid, preferably a nucleic acid heterologous to said host cell, according to the invention. The host cell is preferably selected form the group of bacterial cells, fungal cells (including yeast) and plant cells.

The invention further relates to a method for preparing santalene, comprising converting FPP to santalene in the presence of a santalene synthase according to the invention. Four different geometric isomers of FPP can exist, i.e. 2E,6E-FPP, 2Z,6E-FPP. 2E,6Z-FPP, and 2Z,6Z-FPP. Good results have been obtained with 2E,6E-FPP, although in principle any other isomer of FPP may be a suitable substrate for an enzyme according to the invention.

The invention is further directed to a method for producing a santalene synthase according to the invention, comprising culturing a host cell according to the invention under conditions conducive to the production of the santalene synthase and, optionally, recovering the santalene synthase from the host cell.

A santalene synthase according to the invention has been found to be more specific towards santalene and in particular β-santalene synthesis than a santalene synthase from *S. album*, in particular at or around neutral pH in an in vitro assay or in a method wherein santalene, and in particular β-santalene, is synthesised intracellularly in a host cell genetically modified to produce a santalene synthase according to the invention and a *S. album* santalene synthase, respectively. Initial results show that under identical conditions, the amount of major side product (bergamotene) formed with the novel enzyme of the invention is significantly lower, namely a molar ratio α-santalene/bergamotene=2:1 (0.5:1 for *S. album*)

β-santalene/bergamotene=0.9:1 (0.3:1 for *S. album*)

α+β-santalene/bergamotene=2.9:1 (0.8:1 for *S. album*)

In accordance with the invention it has been found possible to bring the santalene synthase to expression with good yield in distinct organisms. For instance, the santalene synthase has been found to be expressed well in *E. coli, Rhodobacter sphaeroides* and in *Nicotiana benthamiana* plants.

Thus, in an advantageous embodiment, the present invention provides a santalene synthase with improved specificity towards the catalysis of santalene synthesis and an improved production rate for β-santalene, when used in a method for preparing santalene, in particular compared to santalene synthase from *S. album* or another santalene synthase according to the prior art, cited herein.

In a preferred embodiment, a method for preparing santalene according to the invention is provided, wherein the santalene is prepared in a host cell, a plant or plant culture, or a mushroom or mushroom culture, according to the invention, expressing said santalene synthase. Preferably, the method for preparing santalene according to the invention further comprises isolating the santalene from said host cell, plant or plant culture, or mushroom or mushroom culture. Preferably, the method for preparing santalene according to the invention results in an α-santalene to α-bergamotene ratio that is higher than 1:1, more preferably higher than 1.5:1, more preferably higher than 1.7:1, more preferably higher than 1.9:1, most preferably about. 2:1. Preferably, the method for preparing santalene according to the invention results in a ratio β-santalene to α-bergamotene higher than 0.5:1, more preferably higher than 0.6:1, more preferably higher than 0.7:1, more preferably higher than 0.8:1, most preferably about 0.9:1. Preferably, the method for preparing santalene according to the invention results in a ratio of santalenes (α- and β-santalene) to α-bergamotene higher than 2:1, more preferably higher than 2.3:1, more preferably higher than 2.5:1, more preferably higher than 2.7:1, more preferably higher than 2.8:1, most preferably about 2.9:1.

Without being bound by theory, it is thought that a high specificity towards the catalysis of santalene synthesis at neutral or mildly alkaline pH is in particular considered desirable for methods wherein the santalene is prepared intracellularly, because various host cells are thought to have a neutral or slightly alkaline intracellular pH, such as a pH of 7.0-8.5 (for intracellular pH values of bacteria, see for instance: Booth, Microbiological Reviews (1985) 49: 359-378). When, for instance, *E. coli* cells were exposed to pH values ranging from 5.5 to 8.0, the intracellular pH was between 7.1 and 7.9 (Olsen et al., Appl. Environ. Microbiol. (2002) 68: 4145-4147). This may explain an improved specificity towards the synthesis of santalene of a santalene synthase according to the invention, also intracellularly.

The term "or" as used herein is defined as "and/or" unless specified otherwise. The term "a" or "an" as used herein is defined as "at least one" unless specified otherwise.

When referring to a noun (e.g. a compound, an additive, etc.) in the singular, the plural is meant to be included.

The terms farnesyl diphosphate and farnesvlpyrophosphate (both abbreviated as FPP) as interchangeably used herein refer to the compound 3,7,11-trimethyl-2,6,10-dodecatrien-1-yl pyrophosphate and include all known isomers of this compound.

The term "recombinant" in relation to a recombinant cell, vector, nucleic acid or the like as used herein, refers to a cell, vector, nucleic acid or the like, containing nucleic acid not naturally occurring in that cell, vector, nucleic acid or the like and/or not naturally occurring at that same location. Generally, said nucleic acid has been introduced into that strain (cell) using recombinant DNA techniques.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced. Generally, though not necessarily, such nucleic acids encode proteins that are not normally produced by the cell in which the DNA is expressed.

A gene that is endogenous to a particular host cell but has been modified from its natural form, through, for example, the use of DNA shuffling, is also called heterologous. The term "heterologous" also includes non-naturally occurring multiple copies of a naturally occurring DNA sequence. Thus, the term "heterologous" may refer to a DNA segment that is foreign or heterologous to the cell, or homologous to the cell but in a position and/or a number within the host cell nucleic acid in which the segment is not ordinarily found. Exogenous DNA segments are expressed to yield exogenous polypeptides. A "homologous" DNA sequence is a DNA sequence that is naturally associated with a host cell into which it is introduced.

Any nucleic acid or protein that one of skill in the art would recognize as heterologous or foreign to the cell in which it is expressed is herein encompassed by the term heterologous nucleic acid or protein.

The term "mutated" or "mutation" as used herein regarding proteins or polypeptides means that at least one amino acid in the wild-type or naturally occurring protein or polypeptide sequence has been replaced with a different amino acid, or deleted from, or inserted into the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook, J., and Russell, D. W. Molecular Cloning: A Laboratory Manual.3d ed., Cold Spring Harbor Laboratory Press, Cold Spring Harbor, N.Y., (2001). The term "mutated" or "mutation" as used herein regarding genes means that at least one nucleotide in the nucleotide sequence of that gene or a regulatory sequence thereof, has been replaced with a different nucleotide, or has been deleted from or inserted into the sequence via mutagenesis.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The term "transgenic" for a transgenic cell or organism as used herein, refers to an organism or cell (which cell may be an organism per se or a cell of a multi-cellular organism from which it has been isolated) containing a nucleic acid not naturally occurring in that organism or cell and which nucleic acid has been introduced into that organism or cell (i.e. has been introduced in the organism or cell itself or in an ancestor of the organism or an ancestral organism of an organism of which the cell has been isolated) using recombinant DNA techniques.

A "transgene" refers to a gene that has been introduced into the genome by transformation and preferably is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Transformation" and "transforming", as used herein, refers to the introduction of a heterologous nucleotide sequence into a host cell, irrespective of the method used for the insertion, for example, direct uptake, transduction, conjugation, f-mating or electroporation. The exogenous polynucleotide may be maintained as a non-integrated vector, for example, a plasmid, or alternatively, may be integrated into the host cell genome.

"Coding sequence" refers to a DNA or RNA sequence that codes for a specific amino acid sequence and excludes the non-coding sequences. It may constitute an "uninterrupted coding sequence", i.e. lacking an intron, such as in a cDNA or it may include one or more introns bound by appropriate splice junctions. An "intron" is a sequence of RNA which is contained in the primary transcript but which is removed through cleavage and re-ligation of the RNA within the cell to create the mature mRNA that can be translated into a protein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters.

Examples of regulatory sequences include promoters (such as transcriptional promoters, constitutive promoters, inducible promoters), operators, or enhancers, mRNA ribosomal binding sites, and appropriate sequences which control transcription and translation initiation and termination. Nucleic acid sequences are "operably linked" when the regulatory sequence functionally relates to the cDNA sequence of the invention.

Each of the regulatory sequences may independently be selected from heterologous and homologous regulatory sequences.

"Promoter" refers to a nucleotide sequence, usually upstream (5') to its coding sequence, which controls the expression of said coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions. The term "nucleic acid" as used herein, includes reference to a deoxyribonucleotide or ribonucleotide polymer, i.e. a polynucleotide, in either single-or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are "polynucleotides" as the term is used herein. It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including among other things, simple and complex cells.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, the term "conservatively modified variants" refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. The terms "polypeptide", "peptide" and "protein" are used interchangeably herein to refer to a polymer of amino acid residues.

The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

Within the context of the present application, oligomers (such as oligonucleotides, oligopeptides) are considered a species of the group of polymers. Oligomers have a relatively low number of monomeric units, in general 2-100, in particular (3-100. "Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

The term "vector" as used herein refers to a construction comprised of genetic material designed to direct transformation of a targeted cell. A vector contains multiple genetic elements positionally and sequentially oriented, i.e., operatively linked with other necessary elements such that the nucleic acid in a nucleic acid cassette can be transcribed and when necessary, translated in the transformed cells.

In particular, the vector may be selected from the group of viral vectors, (bacterio)phages, cosmids or plasmids. The vector may also be a yeast artificial chromosome (YAC), a bacterial artificial chromosome (BAC) or *Agrobacterium* binary vector. The vector may be in double or single stranded linear or circular form which may or may not be self transmissible or mobilizable, and which can transform prokaryotic or eukaryotic host either by integration into the cellular genome or exist extrachromosomally (e. g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e. g. higher plant, mammalian, yeast or fungal cells). Preferably the nucleic acid in the vector is under the control of and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

Vectors containing a polynucleic acid according to the invention can be prepared based on methodology known in the art per se. For instance use can be made of a cDNA sequence encoding the polypeptide according to the invention operably linked to suitable regulatory elements, such as transcriptional or translational regulatory nucleic acid sequences.

The term "vector" as used herein, includes reference to a vector for standard cloning work ("cloning vector") as well as to more specialized type of vectors, like an (autosomal) expression vector and a cloning vector used for integration into the chromosome of the host cell ("integration vector").

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular, an expression vector comprises a nucleotide sequence that comprises in the 5' to 3' direction and operably linked: (a) a transcription and translation initiation region that are recognized by the host organism, (b) a coding sequence for a polypeptide of interest, and (c) a transcription and translation termination region that are recognized by the host organism. "Plasmid" refers to autonomously replicating extrachromosomal DNA which is not integrated into a microorganism's genome and is usually circular in nature.

An "integration vector" refers to a DNA molecule, linear or circular, that can be incorporated into a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" or "operatively linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

The term "santalene synthase" is used herein for polypeptides having catalytic activity in the formation of santalene and santalene-like terpenes like α-santalene, β-santalene, trans-α-bergamotene and epi-β-santalene from farnesyl diphosphate, and for other moieties comprising such a polypeptide. Examples of such other moieties include complexes of said polypeptide with one or more other polypeptides, fusion proteins of comprising a santalene synthase polypeptide fused to a peptide or protein tag sequence, other complexes of said polypeptides (e.g. metalloprotein complexes), macromolecular compounds comprising said polypeptide and another organic moiety, said polypeptide bound to a support material, etc. The santalene synthase can be provided in its natural environment, i.e. within a cell in which it has been produced, or in the medium into which it has been excreted by the cell producing it. It can also be provided separate from the source that has produced the polypeptide and can be manipulated by attachment to a carrier, labeled with a labeling moiety, and the like.

The term "functional homologue" of a sequence, or in short "homologue", as used herein, refers to a polypeptide comprising said specific sequence with the proviso that one or more amino acids are substituted, deleted, added, and/or inserted, and which polypeptide has (qualitatively) the same enzymatic functionality for substrate conversion in case the term 'functional homologue' is used for an enzyme, i.e. a homologue of the sequence with SEQ ID NO: 3 having catalytic activity in the formation of santalene from farnesyl diphosphate. In the examples a test is described that is suitable to verify whether a polypeptide or a moiety comprising a polypeptide is a santalene synthase ("Santalene synthase activity test"). Moreover, the skilled artisan recognises that equivalent nucleotide sequences encompassed by this invention can also be defined by their ability to hybridize, under low, moderate and/or stringent conditions, with the nucleotide sequences that are within the literal scope of the instant claims.

A preferred homologue to SEQ ID NO: 3 according to the invention has a specificity towards catalysis of santalene formation, expressed as the molar ratio santalene to bergamotene (a known side-product, formed in known santalene synthase catalysed reactions) of at least 1:1, in particular of at least 1.5:1, more particular of at least 2:1, more particular of at least 2.4:1, most particular of at least 2.8:1, when determined at pH 7, using the santalene synthase activity test described herein below in the Examples (using a purified polypeptide). Said ratio may be infinite (1:0; i.e. no detectible amount of bergamotene formed), or up to 100:1, or up to 10:1 or up to 5:1. Sequence identity or similarity is defined herein as a relationship between two or more polypeptide sequences or two or more nucleic; acid sequences, as determined by comparing those sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Sequence identity as used herein is the value as determined by the EMBOSS Pairwise, Alignment Algorithm "Needle", for instance at the server of the European Bioinformatics institute. For alignment of amino acid sequences the default parameters are: Matrix=Blosum62; Open Gap Penalty=10.0; Gap Extension Penalty=0.5. For alignment of nucleic acid sequences the default parameters are: Matrix-DNA full; Open Gap Penalty=10.0; Gap Extension Penalty=0.5.

Discrepancies between a santalene synthase according to SEQ ID NO: 3 or a nucleic acid according to SEQ ID NO: 1 or SEQ ID NO: 2 on hand and a functional homologue of said santalene synthase may in particular be the result of modifications performed, e.g. to improve a property of the santalene synthase or polynucleic acid (e.g. improved expression) by a biological technique known to the skilled person in the art, such as e.g. molecular evolution or rational design or by using a mutagenesis technique known in the art (random mutagenesis, site-directed mutagenesis, directed evolution, gene recombination, etc.). The amino acid sequence or the coding nucleic acid sequence of santalene synthase may be altered compared to the sequences of SEQ ID NO: 3 and SEQ ID NO: 1 or SEQ ID NO: 2, respectively, as a result of one or more natural occurring variations. Examples of such natural modifications/variations are differences in glycosylation (more broadly defined as "post-translational modifications"), differences due to alternative splicing, and single-nucleic acid polymorphisms (SNPs). The nucleic acid may be modified such that it encodes a polypeptide that differs by at least one amino acid from the polypeptide of SEQ ID NO: 3, so that it encodes a polypeptide comprising one or more amino acid substitutions, deletions and/or insertions compared to SEQ ID NO: 3, which polypeptide still has santalene synthase activity. Further, use may be made of codon optimisation or codon pair optimisation, e.g. based on a method as described in WO 2008/000632 or as offered by commercial DNA synthesizing companies like DNA2.0, Geneart, and GenScripi. Examples of one codon optimised sequence is SEQ ID NO: 2. One or more sequences encoding appropriate signal peptides that are not naturally associated with the polypeptides of the invention can be incorporated into (expression) vectors. For example, a DNA sequence for a signal peptide leader can be fused in-frame to a nucleic acid sequence of the invention so that the polypeptide of the invention is initially translated as a fusion protein comprising the signal peptide. Depending on the nature of the signal peptide, the expressed polypeptide will be targeted differently. A secretory signal peptide that is functional in the intended host cells, for instance, enhances extracellular secretion of the expressed polypeptide. Other signal peptides direct the expressed polypeptides to certain organelles, like the chloroplasts, mitochondria and peroxisomes. The signal peptide can be cleaved from the polypeptide upon transportation to the intended organelle or from the cell. It is possible to provide a fusion of an additional peptide sequence at the amino or carboxyl terminal end of a polypeptide according to SEQ ID NO: 3 or homologue thereof.

As mentioned above the invention further relates to a host cell comprising a vector according to the invention. By "host cell" is meant a cell which contains a vector and supports the replication and/or expression of the vector.

The nucleic acid of the invention is heterologous to the host cell of the invention. The host cell may be a prokaryotic cell, a eukaryotic cell or a cell from a member of the Archaea. The host cell may be from any organism, in particular any non-human organism. In particular, the host cell may be selected from bacterial cells, fungal cells, archaea, protists, plant cells (including algae), cells originating from an animal (in particular isolated from said animal). The host cell may form part of a multicellular organism, other than human or the organism from which the enzyme naturally originates (such as *Cinnamomum camphora* in case of the santalene synthase of SEQ ID NO: 3). In a specific embodiment, host cells of the invention are in a culture of cells originating from a multicellular organism, yet isolated therefrom.

In general, the host cell is an isolated cell comprising genes for expressing the enzymes for catalysing the reaction steps of the mevalonate pathway or another metabolic pathway (such as the deoxyxylulose-5-phosphate (DXP) pathway) enabling the production of the C5 prenyl diphosphates isopentenyl diphosphate (IPP) and dimethylallyl diphosphate (DMAPP), which are the universal isoprenoid building blocks. As far as known, unless specific genes have been knocked-out, all known organisms comprise such a pathway. Eukaryotes generally are naturally capable of preparing IPP via the mevalonate pathway. This IPP is then isomerized into DMAPP by the action of the enzyme isopentenyl diphosphate isomerase (ldi). The DXP pathway, which is furnishing IPP and DMAPP in a 5:1 ratio, is common to prokaryotes, although several prokaryotes are naturally capable of preparing IPP via the mevalonate pathway. These pathways are known in the art, and have been described, e.g., by Withers & Keasling in Appl. Microbiol. Biotechnol. (2007) 73: 980-990. The genes of these pathways may each independently be homologous or heterologous to the cell.

The host cells further will, either endogenically or from heterologous sources, comprise one or more genes for expressing enzymes with prenyl transferase activity catalysing the head-to-tail condensation of the C5 prenyl diphosphates producing longer prenyl diphosphates. The universal sesquiterpene precursor farnesyl diphosphate (FPP), for instance, is formed by the action of these enzymes through the successive head-to-tail addition of 2 molecules of IPP to 1 molecule of DMAPP. In an embodiment, the host cell is a bacterium. The bacterium may be gram-positive or gram-negative. Gram-positive bacteria may be selected from the genera of *Bacillus* and *Lactobacillus*, in particular from the species of *Bacillus subtilis* and *Lactobacillus casei*.

In a preferred embodiment, the bacterium is selected from the group of Gram-negative bacteria, in particular from the group of *Rhodobacter, Paracoccus* and *Escheriehia*, more in particular from the group of *Rhodobacter capsulatus, Rhodobacter sphaeroides, Paracoccus carotinifaciens, Paracoccus zeaxanthinifaciens* and *Escherichia coli. Rhodobacter sphaeroides* is an example of an organism naturally containing all genes needed for expressing enzymes catalysing the various reaction steps in the DXP pathway, enabling the intracellular production of IPP and DMAPP.

In a preferred embodiment, the host cell is a fungal cell, in particular a fungal cell selected from the group of *Aspergillus, Makeslea, Penicillium, Phaffia* (*Xanthophyllomyces*), *Pichia, Saccharomyces* and *Yarrowia*, more in particular from the group of *Aspergillus nidulans, Aspergillus niger, Aspergillus oryzae, Blakeslea trispora, Penicillium chrysogenum, Phaffia rhodozyma* (*Xanthophyllomyces dendrorhous*), *Pichia pastoris, Saccharomyces cerevisiae* and *Yarrowia lipolytica.*

It is also possible to express the nucleic acids of the invention in cells derived from higher eukaryotic organisms, such as plant cells and animal cells, such as insect cell, or cells from mouse, rat or human. Said cells can be maintained in a cell or tissue culture and be used for in vitro production of santalene synthase.

A multicellular organism comprising host cells according to the invention may in particular be selected from the group of multicellular plants and mushrooms (*Basidiomycetes*).

Thus, in a specific embodiment, the invention relates to a transgenic plant or plant cell or tissue culture comprising transgenic plant cells, said plant or culture comprising plant host cells according to the invention. The transgenic plant or culture of transgenic plant cells may in particular be selected from *Nicotiana* spp., *Solanum* spp., *Cichorum intybus, Lactuca sativa, Mentha* spp., *Artemisia annua*, tuber forming plants, such as *Helianthus tuberosus*, cassava and *Beta vulgaris*, oil crops, such as *Brassica* spp., *Elaeis* spp. (oil palm tree), *Helianthus annuus, Glycine max* and *Arachis hypogaea*, liquid culture plants, such as duckweed *Lemna* spp., tobacco BY2 cells and *Physcomitrella patens*, trees, such as pine tree and poplar, respectively a cell culture or a tissue culture of any of said plants. In a specific embodiment, the tissue culture is a hairy root culture.

In a further specific embodiment, the invention relates to a transgenic mushroom or culture comprising transgenic mushroom cells. The transgenic mushroom or culture comprising transgenic host cells, may in particular be selected from the group of *Schizophyllum, Agaricus* and *Pleurotus*, more in particular from *Schizophyllum commune*, the common mushroom (*Agaricus bisporus*), the oyster mushroom (*Pleurotus ostreotus* and *Pleurotus sapidus*), respectively a culture comprising cells of any of said mushrooms.

A host cell according to the invention may be produced based on standard genetic and molecular biology techniques that are generally known in the art, e.g. as described in Sambrook, J., and Russell, D. W. "Molecular Cloning: A Laboratory Manual" 3d ed., Cold Spring Harbor Laboratory Press, Cold Spring Harbor, N.Y., (2001); and F. M. Ausubel et al, eds., "Current protocols in molecular biology", John Wiley and Sons, Inc., New York (1987), and later supplements thereto.

Methods to transform *Basidiomycetes* are known from, for example, Alves et al. (Appl. Environ. Microbiol. (2004) 70: (3379-6384), Godio et al. (Curr. Genet. (2004) 46: 287-294), Schuurs et al. (Genetics (1997) 147: 589-596), and WO 06/096050. To achieve expression of a suitable santalene synthase gene in basidiomycetes, its complete open reading frame is typically cloned into an expression vector suitable for transformation of basidiomycetes. The expression vector preferably also comprises nucleic acid sequences that regulate transcription initiation and termination. It is also preferred to incorporate at least one selectable marker gene to allow for selection of transformants. Expression of a santalene synthase can be achieved using a basidiomycete promoter, e.g. a constitutive promoter or an inducible promoter. An example of a strong constitutive promoter is the glyceraldehyde-3-phosphate dehydrogenase (gpdA) promoter. This promoter is preferred for constitutive expression when recombinant DNA material is expressed in a basidiomycete host.

Other examples are the phosphoglycerate kinase (pgk) promoter, the pyruvate kinase (pki) promoter, TPI, the triose phosphate isomerase (tpi) promoter, the APC synthetase subunit g (oliC) promoter, the sc3 promoter and the acetamidase (amdS) promoter of a basidiomycete (WO 96/41882).

If needed, the primary nucleotide sequence of the santalene synthase gene can be adapted to the codon usage of the basidiomycete host.

Further, expression can be directed especially to the (monokaryotic) mycelium or to the (dikaryotic) fruiting bodies. In the latter case, the Fbh1 promoter of *Pleurotis* is especially useful (Penas, M. M. et at, Mycologia (2004) 96: 75-82).

Methodologies for the construction of plant transformation constructs are described in the art. Overexpression can be achieved by insertion of one or more than one extra copy of the selected gene. It is not unknown for plants or their progeny, originally transformed with one or more than one extra copy of a nucleotide sequence to exhibit overexpression.

Obtaining sufficient levels of transgenic expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell or tissue. In some cases, expression in multiple tissues is desirable, and constitutive promoters such as the 35S promoter series may be used in this respect. However, in some of the embodiments of the present invention it is preferred that the expression in transgenic plants is leaf-specific, more preferably, the expression of the gene occurs in the leaf plastids. The promoter of the isoprene synthase gene from *Populus alba* (PaIspS) (Sasaki et al., FEBS Letters (2005) 579: 2514-2518) appears to drive plastid-specific expression. Hence, this promoter is a very suitable promoter for use in an expression vector of the present invention.

Other suitable leaf-specific promoters are the rbcS (Rubisco) promoter (e.g. from coffee, see WO 02/092822); from *Brassica*, see U.S. Pat. No. 7,115,733; from soybean, see Dhanker, O., et al., Nature Biotechnol. (2002) 20: 1140-1145), the cy-FBPase promoter (see U.S. Pat. No. 6,229,067), the promoter sequence of the light-harvesting chlorophyll a/b binding protein from oil-palm (see US 2006/0288409), the STP3 promoter from *Arabidopsis thaliana* (see, Büttner, M. et al., Plant cell & Environ. (2001) 23: 175-184), the promoter of the bean PAL2 gene (see Sablowski, R. W. et al., Proc. Natl. Acad. Sci. USA (1995) 92: 6901-6905), enhancer sequences of the potato ST-LS1 promoter (see Stockhaus, J. et al., Proc. Natl. Acad. Sci. USA (1985) 84: 7943-7947), the wheat CAB1 promoter (see Gotor, C. et al., Plant J. (1993) 3: 509-518), the stomata-specific promoter from the potato ADP-glucose-phosphorylase gene (see U.S. Pat. No. 5,538,879), the LPSE1 element from the P(D540) gene of rice (see CN 2007/10051443), and the stomata specific promoter, pGC1(At1g22690) from *Arabidopsis thaliana* (see Yang, Y. et al., Plant Methods (2008) 4: 6).

Plant species may, for instance, be transformed by the DNA-mediated transformation of plant cell protoplasts and subsequent regeneration of the plant from the transformed protoplasts in accordance with procedures well known in the art.

Further examples of methods of transforming plant cells include microinjection (Crossway et al., Mol. Gen. Genet. (1986) 202: 179-185), electroporation (Riggs, C. D. and Bates, G. W., Proc. Natl. Acad. Sci. USA (1986), 83: 5602-5606), *Agrobacterium*-mediated transformation (Hinchee et al., Bio/Technol. (1988) 6: 915-922), direct gene transfer (Paszkowski. J. et al., EMBO J. (1984) 3: 2717-2722), and ballistic particle acceleration using devices available from Agracetus, Inc., Madison, Wis. and BioRad, Hercules, Calif. (see, for example, Sanford et al., U.S. Pat. No. 4,945,050 and European Patent Application EP 0 332 581).

It is also possible to employ the protoplast transformation method for maize (European Patent Application EP 0 292 435, U.S. Pat. No. 5,350,689).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., Bio/technol. (1985) 3: 241; Byrne M. C. et al., Plant Cell Tissue and Organ Culture (1987) 8: 3-15; Sukhapinda, K. et al., Plant Mol. Biol. (1987) 8: 209-217; Hiei, Y. et al., The Plant J. (1994) 6: 271-282). The use of T-DNA to transform plant cells has received extensive study and is amply described (e.g. EP-A 120 516). For introduction into plants, the chimeric genes of the invention can be inserted into binary vectors as described in the examples.

Other transformation methods are available to those skilled in the art, such as direct uptake of foreign DNA constructs (see EP-A 295 959), techniques of electroporation (Fromm, M. E. et al., Nature (1986), 319: 791-793) or high velocity ballistic bombardment with metal particles coated with the nucleic acid constructs (e.g. U.S. Pat. No. 4,945,050). Once transformed, the cells can be regenerated by those skilled in the art.

Of particular relevance are the methods to transform foreign genes into commercially important crops, such as rapeseed (De Block, M. et al., Plant Physiol. (1989) 91: 694-701), sunflower (Everett, N. P. et al., Bio/Technology (1987) 5: 1201-1204), soybean (EP-A 301 749), rice (Hiei, Y. et al., The Plant J. (1994) 6: 271-282), and corn (Fromm et al., 1990, Bio/Technology 8: 833-839).

Those skilled in the art will appreciate that the choice of method might depend on the type of plant, i.e., monocotyledonous or dicotyledonous.

In another embodiment, the vector as described herein may be directly transformed into the plastid genome. Plastid transformation technology is extensively described in, e.g., U.S. Pat. Nos. 5,451,513, 5,545,817, 5,545,818 and WO 95/16783. The basic technique for chloroplast transformation involves introducing regions of cloned plastid DNA flanking a selectable marker together with the gene of interest into a suitable target tissue, e.g., using biolistics or protoplast transformation (e.g. calcium chloride or PEG mediated transformation).

*Agrobacterium tumefaciens* cells containing a vector according to the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known. These typically carry at least one T-DNA border sequence and include vectors such as pBIN19 (Bevan, Nucl. Acids Res. (1984) 12: 8711-8720).

Methods using either a form of direct gene transfer or *Agrobacterium*-mediated transfer usually, but not necessarily, are undertaken with a selectable marker which may provide resistance to an antibiotic (e. g. kanamycin, hygromycin or methotrexate) or a herbicide (e. g. phosphinothricin). The choice of selectable marker for plant transformation is not, however, critical to the invention.

General methods of culturing plant tissues are provided for example by Maki, K. Y. et al., Plant Physiol. (1993) 15: 473-497; and by Phillips, R. I. et al. In: Sprague G F. Dudley J W, eds. *Corn and corn improvement.* 3rd edn. Madison (1988) 345-387.

After transformation, the transgenic plant cells are placed in an appropriate selective medium for selection of transgenic cells which are then grown to callus. Shoots are grown from callus and plantlets generated from the shoot by growing in rooting medium. The particular marker used will allow for selection of transformed cells as compared to cells lacking the DNA which has been introduced.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR and "biochemical" assays, such as detecting the presence of a protein product, e.g., by immunological means (ELISAs and Western blots) or by enzymatic function. The presence of enzymatically active santalene synthase may be established by chemical analysis of the volatile products (santalene) of the plant.

A santalene synthase according to the invention may be used for the industrial production of santalene, which santalene may be used per se as a flavour or aroma, e.g. in a food product, or as a fragrance, e.g. in a household product, or as an intermediate for the production of another isoprenoid, e.g. santalol.

A method for producing santalene according to the invention comprises preparing santalene in the presence of santalene synthase. In principle, such a method can be based on any technique for employing an enzyme in the preparation of a compound of interest.

The method can be a method wherein FPP or any of its precursors (such as farnesol, IPP, isopentenyl phosphate, 3-methylbut-3-en-1-ol and even mevalonate) is fed as a substrate to cells comprising the santalene synthase. Alternatively, the method can also be a method wherein use is made of a living organism that comprises an enzyme system capable of forming FPP from a suitable carbon source, thus establishing a full fermentative route to santalene. It should be noted that the term "fermentative" is used herein in a broad sense for processes wherein use is made of a culture of an organism to synthesise a compound from a suitable feedstock (e.g. a carbohydrate, an amino acid source, a fatty acid source). Thus, fermentative processes as meant herein are not limited to anaerobic conditions, and extended to processes under aerobic conditions. Suitable feedstocks are generally known for specific species of (micro-)organisms.

Also, use may be made of the santalene synthase isolated from the cell wherein it has been produced, e.g. in a reaction system wherein the substrate (FPP) and the santalene synthase are contacted under suitable conditions (pH, solvent, temperature), which conditions may be based on the prior art referred to herein and the present disclosure, optionally in combination with some routine testing. The santalene synthase may e.g. be solubilised in an aqueous medium wherein also the FPP is present or the santalene synthase may be immobilised on a support material in a manner known in the art and then contacted with a liquid comprising the FPP. Since the enzyme has a high activity and/or selectivity towards the catalysis from FPP to santalene, the present invention is also advantageous for such an in vitro method, not only under acidic conditions, but also in case the pII is about neutral or alkaline. Suitable conditions may be based on known methodology for known santalene synthases, e.g. referred to in the literature referred to herein, the information disclosed herein, common general knowledge and optionally some routine experimentation.

In a particularly advantageous method of the invention, santalene is fermentatively prepared, i.e. by cultivating cells expressing santalene synthase in a culture medium.

The actual reaction catalysed by the santalene synthase may take place intracellularly or—if the santalene synthase is excreted into the culture medium—extracellularly in the culture medium.

The cells used for in a method for preparing santalene according to the invention may in particular be host cells according to the invention. If desired, these host cells may be engineered to supply the FPP to the santalene synthase in increased amounts. This can for instance be done by enhancing the flux of carbon towards FPP, which in itself can be realized in different ways. In host cells with an endogenous DXP pathway (like *E. coli* and *R. sphaeroides*) deregulation of the expression of these pathway's enzymes can have a clear positive effect on isoprenoids formation. Overexpression of dxs encoding 1-deoxy-D-xylulose-5-phosphate synthase (DXP-synthases), the first enzyme of the DXP pathway and thus one of the main targets for metabolic engineering, has resulted in increased biosynthesis of several isoprenoids (e.g., Matthews and Wurtzel, Appl. Microbiol. Biotechnol. (2000) 53: 396-400; Huang et al., Bioorg. Med. Chem. (2001) 9: 2237-2242; Harker and Bramley, FEBS Lett (1999) 448: 115-119; Jones et al. Metab. Eng. (2000) 2: 328-338; and Yuan et al. Metab. Eng. (2006) 8: 79-90). Also overexpression of dxr coding for DXP isomeroreductase (also known as 1-deoxy-D-xylulose-5-phosphate reductoisomerase), the enzyme catalyzing the second and committed step in the DXP pathway, can lead to increased isoprenoid production (Albrecht et al., Biotechnol. Lett. (1999) 21: 791-795), which effect can be further increased by co-overexpressing dxs at the same time (Kim & Keasling, Biotechnol Bioeng (2001) 72: 408-415). A positive effect on isoprenoid biosynthesis was further obtained by overexpression of isopentenyl diphosphate isomerase (IPP isomerase, Idi), the enzyme that catalyzes the interconversion of IPP to dimethylallyl diphosphate, DMAPP (e.g., Kajiwara et al. Biochem. J. (1997) 324: 421-426); Misawa and Shimada, J. Biotech. (1998) 59: 169-181; and Yuan et al. Metab. Eng. (2006) 8: 79-90) and the enzymes MEP cytidylyltransferase (also known as 4-diphosphocytidyl-2-C-methyl-D-erythritol synthase, IspD) and 2C-methyl-D-erythritol 2,4-cyclodiphosphate synthase (IspF), that are transcribed as one operon ispDF in *E. coli* (Yuan et al. Metab. Eng. (2006) 8: 79-90).

An alternative and more efficient approach to engineer strains with an endogenous DXP pathway for high-level production of isoprenoids is the introduction of a heterologous mevalonate pathway. Coexpression in *E. coli* of the *Saccharomyces cerevisiae* mevalonate pathway with a synthetic amorpha-4,11-diene synthase gene resulted in the formation of the sesquiterpene amorphadiene in titres of more than 110 mg/L when the recombinant *E. coli* strain was cultivated in an LB+ glycerol medium (Martin et al. Nat. Biotechnol. (2003) 21: 796-802). This *E. coli* strain was subsequently improved by the introduction of extra copies of the gene tHMG1 encoding the C-terminal catalytic domain of the yeast enzyme 3-hydroxy-3-methyl-glutaryl-coenzyme A (HMG-CoA) reductase. By increasing the formation and thus the activity of this enzyme, the intracellular level of the toxic mevalonate pathway intermediate HMG-CoA was reduced thereby overcoming growth inhibition and leading to an increased production of mevalonate (Pitera et al. Metab. Eng. (2007) 9: 193-207). Further improvement of the flux through the heterologous mevalonate pathway was obtained by codon optimization of the first three genes of this pathway in combination with replacement of the wild-type lac promoter with the two-fold stronger lacUV5 promoter (Anthony et al. Met. Eng. (2009) 11: 13-19). The production of amorphadiene could be even more increased by replacing the yeast genes for HMG-CoA synthase and HMG-CoA reductase with the equivalent genes from the gram positive bacterium *Staphylococcus aureus*. In combination with an optimized fermentation protocol, cultivation of this novel engineered *E. coli* strain yielded an amorphadiene titre of 27.4 g/L (Tsuruta et al. PloS ONE (2009) 4(2): e4489. doi:10.1371/journal.pone.0004489). Similarly, an *E. coli* strain engineered with the mevalonate pathway from *Streptococcus pneumoniae* in combination with the *Agrobacterium tumefaciens* decaprenyl diphosphate synthase (ddsA) gene produced coenzyme $Q_{10}$ ($CoQ_{10}$) in more than 2400 μg/g cell dry weight (Zahiri et al. Met. Eng. (2006) 8: 406-416. Increased production of $CoQ_{10}$ was also obtained by engineering a *Rhodobacter sphaeroides* strain with the mevalonate pathway from *Paracoceus zeaxanthinifaciens* in its native (WO 2005/005650) and a mutated form (WO 2006/018211).

Also host cells with an endogenous MEV pathway (like *S. cerevisiae*) have been the subject of multiple engineering studies to obtain isoprenoid hyper producing strains. Introduction into *S. cerevisiae* of the heterologous *E. coli* derived DXP pathway in combination with the gene encoding the Citrus santalene synthase resulted in a strain accumulating approximately 10-fold more santalene compared to the strain expressing only the santalene synthase (WO 2007/093962). Most improvements in the industrially-important yeasts *Candida utilis* and *S. cerevisiae*, however, have centred on the engineering of the homologous MEV pathway. Especially overexpression of the enzyme HMG-CoA reductase, which is believed to be the main regulatory enzyme in the DXP pathway, in its full-length or truncated version, has appeared to be an efficient method to increase production of isoprenoids. This stimulating effect of overexpression of the N-terminal truncated HMG-CoA reductase has, for instance, been observed in case of lycopene production in *C. utilis* (Shimada et al. Appl. Env. Microbiol. (1998) 64: 2676-2680) and epi-cedrol production in *S. cerevisiae* (Jackson et al. Org. Lett. (2003) 5: 1629-1632). In the last case, the production of this sesquiterpene could be further enhanced by introduction of upc2-1, an allele that elicitates an increase in the metabolic flux to sterol biosynthesis. Another method to increase the flux through the MEV pathway is the employment of a mevalonate kinase variant that is less sensitive for feedback inhibition by FPP and other isoprenoid precursors. WO 2006/063752, for instance, shows that *Paracoccus zeaxanthinifaciens* R114, a bacterium with an endogenous MEV pathway, after introduction of the *S. cerevisiae* mevalonate kinase mutant N66K/I152M and the ddsA gene from *P. zeaxanthinifaciens* ATCC 21588 produces significantly more coenzyme $Q_{10}$ than the corresponding *P. zeaxanthinifaciens* strain expressing the wild type *S. cerevisiae* mevalonate kinase. Similar positive results on $CoQ_{10}$ production with *P. zeaxanthinifaciens* R114 have also been obtained with the feedback resistant variant K93E of the *P. zeaxanthinifaciens* mevalonate kinase (WO 2004/111214).

A second approach to increased amounts of FPP is based on reducing or elimination of enzymatic side activities on FPP. In yeast the gene ERG9 encodes the enzyme farnesyl diphosphate farnesyl transferase (squalene synthase), which catalyzes the condensation of two farnesyl diphosphate moieties to form squalene. Because this is the first step after FPP in the sterol biosynthesis and thus regulates the flux of isoprene units into the sterol pathway, ERG9 is a frequent target in yeast metabolic engineering for increased sesquiterpene and carotenoids production. Disruption of ERG9 in combination with overexpression of the tHMG-CoA reductase in the yeast *C. utilus* led to increased production of lycopene (Shimada et at Appl. Env. Microbiol. (1998) 64: 2676-2680). A similar combination of overexpression of tHMG-CoA reductase and downregulation of ERG9 using a methionine repressible promoter increased the production of the sesquiterpene amorphadiene in yeast with approx. 10-fold as compared to the yeast strain only expressing the amorphadiene synthase gene (Ro et al. Nature (2006) 440: 940-943; Lenihan et al. Biotechnol. Prog. (2008) 24: 1026-1032). Since ergosterol is vital for yeast growth and yeast cells cannot assimilate externally fed ergosterol during aerobic growth, downregulation/knockout of ERG9 is frequently combined with mutations that equip the yeast strain with efficient aerobic uptake of ergosterol from the culture medium. Examples are the sue allele (Takahishi et al. Biotechnol. Bioeng. (2007) 97: 170-181) and the upc2-1 allele (Jackson et al. Org. Lett. (2003) 5: 1629-1632). Takahashi et al (Biotechnol. Bioeng. (2007) 97: 170-181) also investigated the effect of limiting the endogenous phosphatase activity by knocking out the phosphatase gene dpp1 in yeast. Although this knockout clearly limited the dephosphorylation of FPP reflected by much less farnesol accumulation, it did not improve sesquiterpene production beyond that of the combined erg9/sue mutations under the growth conditions applied.

Reaction conditions for fermentatively preparing santalene may be chosen depending upon known conditions for the species of host cell used (e.g. *Rhodobacter capsulatus, Rhodobacter sphaeroides, Paraeoccus zeaxanthinifaciens, Escherichia coli, Aspergillus nidulans, Aspergillus niger, Aspergillus oryzae, Saccharomyces cerevisiae, Penicillium chrysogenum, Phaffia rhodozyma* and *Pichia pastoris*), the information disclosed herein, common general knowledge and optionally some routine experimentation. In principle, the pH of the reaction medium (culture medium) used in a method according to the invention may be chosen within wide limits, as long as the santalene synthase (in the host cell) is active and displays a wanted specificity under the pH conditions. In case the method includes the use of cells, for expressing the santalene synthase, the pH is selected such that the cells are capable of performing its intended function or functions. The pH may in particular be chosen within the range of four pH units below neutral pH and two pH units above neutral pH, i.e. between pH 3 and pH 9 in case of an essentially aqueous system at 25° C. Good results have e.g. been achieved in an aqueous reaction medium having a pH in the range of 6.8 to 7.5.

A system is considered aqueous if water is the only solvent or the predominant solvent (>50 wt. %, in particular >90 wt. %, based on total liquids), wherein e.g. a minor amount of alcohol or another solvent (<50 wt. %, in particular <10 wt. %, based on total liquids) may be dissolved (e.g. as a carbon source, in case of a full fermentative approach) in such a concentration that micro-organisms which are present remain active.

In particular, in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base. Anaerobic conditions are herein defined as conditions without any oxygen or in which substantially no oxygen is consumed by the cultured cells, in particular a micro-organism, and usually corresponds to an oxygen consumption of less than 5 mmol/l.h, preferably to an oxygen consumption of less than 2.5 mmol/l.h, or more preferably less than 1 mmol/l.h. Aerobic conditions are conditions in which a sufficient level of oxygen for unrestricted growth is dissolved in the medium, able to support a rate of oxygen consumption of at least 10 mmol/l.h, more preferably more than 20 mmol/l.h, even more preferably more than 50 mmol/l.h, and most preferably more than 100 mmol/l.h. Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l.h, and in particular at least 2.5 mmol/l.h, or at least 5 mmol/l.h. The upper limit for oxygen-limited conditions is determined by the lower limit for aerobic conditions, i.e. less than 100 mmol/l.h, less than 50 mmol/l.h, less than 20 mmol/l.h, or less than to 10 mmol/l.h.

Whether conditions are aerobic, anaerobic or oxygen-limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the santalene synthase (in the cells), shows substantial activity. Generally, the temperature may be at least 0° C., in particular at least 15° C., more in particular at least 20° C. A desired maximum temperature depends upon the santalene synthase and the cells, in ease of a method wherein use is made of cells for expressing the santalene synthase. The temperature is 70° or less, preferably 50° C. or less, more preferably 40° C. or less, in particular 35° C. or less.

In case of a fermentative process, the incubation conditions can be chosen within wide limits as long as the cells show sufficient activity and/or growth. This includes aerobic, oxygen-limited and anaerobic conditions.

In particular, if the catalytic reaction whereby santalene is formed, is carried out outside a host cell, a reaction medium comprising an organic solvent may be used in a high concentration (e.g. more than 50%, or more than 90 wt. %, based on total liquids), in case the santalene synthase that is used retains sufficient activity and specificity in such a medium.

If desired, santalene produced in a method according to the invention, or a further compound into which santalene has been converted after its preparation (such as santalol), is recovered from the reaction medium, wherein it has been made. A suitable method is liquid-liquid extraction with an extracting liquid that is non-miscible with the reaction medium.

In particular, suitable (for extraction from an aqueous reaction medium) is extraction with a liquid organic solvent, such as a liquid hydrocarbon. From initial results it is apparent that this method is also suitable to extract the santalene (or further product) from a reaction medium comprising cells according to the invention used for its production, without needing to lyse the cells for recovery of the santalene (or further product),In particular, the organic solvent may be selected from liquid alkanes, liquid long-chain alcohols (alcohols having at least 12 carbon atoms), and liquid esters of long-chain fatty acids (acids having at least 12 carbon atoms). Suitable liquid alkanes in particular include C6-C16 alkanes, such as hexane, octane, decane, dodecane, isododecane and hexadecane. Suitable long-chain aliphatic alcohol in particular include C12-C18 aliphatic alcohols, like oleyl alcohol and palmitoleyl alcohol. Suitable esters of long-chain fatty acids in particular include esters of C1-C4 alcohols of C12-C18 fatty acids, like isopropyl myristate, and ethyl oleate.

In an advantageous embodiment, santalene (or a further product) is produced in a reactor comprising a first liquid phase (the reaction phase), said first liquid phase containing cells according to the invention in which cells the santalene (or a further product) is produced, and a second liquid phase (organic phase that remains essentially phase-separated with the first phase when contacted), said second liquid phase being the extracting phase, for which the formed product has a higher affinity.

This method is advantageous in that it allows in situ product recovery. Also, it contributes to preventing or at least reducing potential toxic effects of santalene (or a further product) to the cells, because due to the presence of the second phase, the santalene (or a further product) concentration in the reaction phase may be kept relatively low throughout the process. Finally, there are strong indications that the extracting phase contributes to extracting the santalene (or further product) out of the reaction phase.

In a preferred method of the invention the extracting phase forms a layer on top of the reaction phase or is mixed with the reaction phase to form a dispersion of the reaction phase in the extracting phase or a dispersion of the extracting phase in the reaction phase. Thus, the extracting phase not only extracts product from the reaction phase, but also helps to reduce or completely avoid losses of the formed product from the reactor through the off-gas, that may occur if santalene is produced in the (aqueous) reaction phase or excreted into the (aqueous) reaction phase. Santalene is poorly soluble in water and therefore easily volatilizes from water. It is contemplated that santalene solvated in the organic phase (as a layer or dispersion) is at least substantially prevented from volatilization.

Suitable liquids for use as extracting phase combine a lower density than the reaction phase with a good biocompatibility (no interference with the viability of living cells), low volatility, and near absolute immiscibility with the aqueous reaction phase.

Examples of suitable liquids for this application are liquid alkanes like decane, dodecane, isododecane, tetradecane, and hexadecane or long-chain aliphatic alcohols like oleyl alcohol, and palmitoleyl alcohol, or esters of long-chain fatty acids like isopropyl myristate, and ethyl oleate (see e.g. Asadollahi et al. (Biotechnol. Bioeng. (2008) 99: 666-677), Newman et al. (Biotechnol, Bioeng. (2006) 95: 684-691) and WO 2009/042070).

The santalene produced in accordance with the invention may be used as such, e.g. for use as a flavour or fragrance, or as an insect repellent, or may be used as a starting material for another compound, in particular another flavour or fragrance. In particular, santalene may be converted into santalol. The conversion of santalene into santalol may be carried out intracellularly, or extracellularly. If this preparation is carried out inside a cell, the santalol is usually isolated from the host cell after its production. The invention further relates to a method for preparing santalol, preferably β-santalol, comprising converting FPP to santalene, preferably β-santalene, in the presence of a santalene synthase according to the invention, further comprising converting the santalene into santalol, preferably β-santalol. Preferably, the santalene is prepared in a host cell, a plant or plant culture, or a mushroom or mushroom culture, expressing said santalene synthase, according to the invention. In a preferred embodiment, a method for preparing santalol, preferably β-santalol, according to the invention is provided, further comprising isolating the santalol.

In general, suitable methods to prepare santalol from santalene may be divided in: i) purely chemical methods as described in Willis et al. (1985) in example 11, ii) biocatalytic methods (e.g. those using P450 monooxygenases) as exemplified by Daviet et al. (2015) which could also be performed as a bioconversion (i.e. methods applying whole living cells), and iv. full fermentation and iii) autocatalytic oxidation of santalene as exemplified by Ngo & Brown (2000).In a specific embodiment the conversion comprises a regiospecific hydroxylation of santalene to form santalol.

It is contemplated that one or more genes encoding an enzyme or plurality of enzymes for catalysing the conversion of santalene into santalol may be incorporated in a host cell according to the invention. Such enzymes may in for instance be selected from the enzymes of *Chlorella* or *Botryosphaeria*, or Premnaspirodiene oxidase from *Hyoscyamus muticus*, or the P450cam or P450BM-3 mutants referred to herein above.

As indicated above, the invention relates to an antibody having binding affinity to a santalene synthase according to the invention. The term "antibody" includes reference to antigen binding forms of antibodies (e. g., Fab, F (ab)2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The antibodies or fragments thereof can be produced by any method known in the art for the synthesis of antibodies, in particular, by chemical synthesis or preferably, by recombinant expression techniques.

Polyclonal antibodies to santalene synthase can be produced by various procedures well known in the art. For example, a heterologous santalene synthase can be administered to various host animals including, but not limited to, rabbits, mice, rats, etc. to induce the production of sera containing polyclonal antibodies specific for santalene synthase. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parcum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal. Antibodies and T-Cell Hybridomas* 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with santalene synthase and once an immune response is detected, e.g., antibodies specific for the santalene synthase are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

In certain embodiments, a method of generating monoclonal antibodies comprises culturing a hybridoma cell secreting an antibody of the invention wherein, preferably, the hybridoma is generated by fusing splenocytes isolated from a mouse immunized with santalene synthase with myeloma cells and then screening the hybridomas resulting from the fusion for hybridoma clones that secrete an antibody able to bind santalene synthase. An antibody according to the invention may for instance be used in a method for isolating a santalene synthase produced in accordance with the invention, e.g. by using the antibody immobilised on a chromatographic support material.

Further, the present disclosure is directed to a method for preparing santalene or santalol, the method comprising converting a polyprenyl diphosphate substrate into the santalene or santalol in the presence of an enzyme, the enzyme comprising a first segment comprising a tag-peptide and a second segment comprising a santalene synthase according to the invention. An enzyme comprising said first and said second segment may herein be referred to as a 'tagged enzyme'.

For santalene preparation in particular use can be made of a method, an amino acid sequence, a nucleic acid sequence or a host cell as described herein. Santalol can, for instance, be prepared by oxygenation/oxidation of santalene in a manner known per se.

The tag-peptide is preferably selected from the group of nitrogen utilization proteins (NusA; SEQ ID NO: 26), thioredoxins (Trx; SEQ ID NO: 27), maltose-binding proteins (MBP; SEQ ID NO: 28), a so called SET-tag, SEQ ID NO: 29), and functional homologues thereof. As used herein a functional homologue of a tag peptide is a tag peptide having at least about the same effect on the solubility of the tagged enzyme, compared to the non-tagged enzyme. Typically the homologue differs in that one or more amino acids have been inserted, substituted, deleted from or extended to the peptide of which it is a homologue. The homologue may in particular comprise one or more substitutions of a hydrophilic amino acid for another hydrophilic amino acid or of a hydrophobic amino acid for another. The homologue may in particular have a sequence identity of at least 40%, more in particular of at least 50%, preferably of at least 55%, more preferably of at least 60%, at least 70%, at least 75%, at least 80%, at least 85%, at least, 90%, at least 95%, at least. 98% or at least 99% with the sequence of a NusA, Trx, MBP or SET.

Particularly suitable is maltose binding protein from *Escherichia coli*, or a functional homologue thereof.

The use of a tagged enzyme according to the invention is in particular advantageous in that it may contribute to an increased production, especially increased cellular production of a terpenoid or a terpene, such as α-santalene and β-santalene.

For improved solubility of the tagged enzyme (compared to the enzyme without the tag), the first segment of the enzyme is preferably bound at its C-terminus to the N-terminus of the second segment. Alternatively, the first segment of the tagged enzyme is bound at its N-terminus to the C-terminus of the second segment.

Further, the present disclosure is directed to a nucleic acid comprising a nucleotide sequence encoding a polypeptide, the polypeptide comprising a first segment comprising a tag-peptide, preferably an MBP, a NusA, a Trx, a SET-tag) or a functional homologue of any of these, and a second segment comprising a a santalene synthase or an amorphadiene synthase. The second segment may for instance comprise an amino acid sequence as shown in SEQ ID NO: 3.

Further, the present disclosure is directed to a host cell comprising said nucleic acid encoding said tagged santalene synthase. Specific nucleic acids according to the invention encoding a tagged enzyme are shown in SEQ ID NO: 4, SEQ ID NO: 6, SEQ ID NO: 30, SEQ ID NO: 31. The host cell may in particular comprise a gene comprising any of these sequences or a functional analogue thereof.

Further, the present disclosure is directed to an enzyme, comprising a first segment comprising a tag-peptide and a second segment comprising a polypeptide having enzymatic activity for converting a polyprenyl diphosphate into a terpene, in particular a santalene synthase, the tag-peptide preferably being selected from the group of MBP, NusA, Trx or SET). Specific enzymes comprising a tagged enzyme according to the invention are shown in SEQ ID NO: 5, SEQ ID NO: 7, SEQ ID NO: 32, SEQ ID NO: 33.

The invention will now be illustrated by the following examples.

FIGURE LEGENDS

FIG. 1 Map of plasmid p-m-LPppa-CiCaSSy-mpmii alt.

Figure 2:
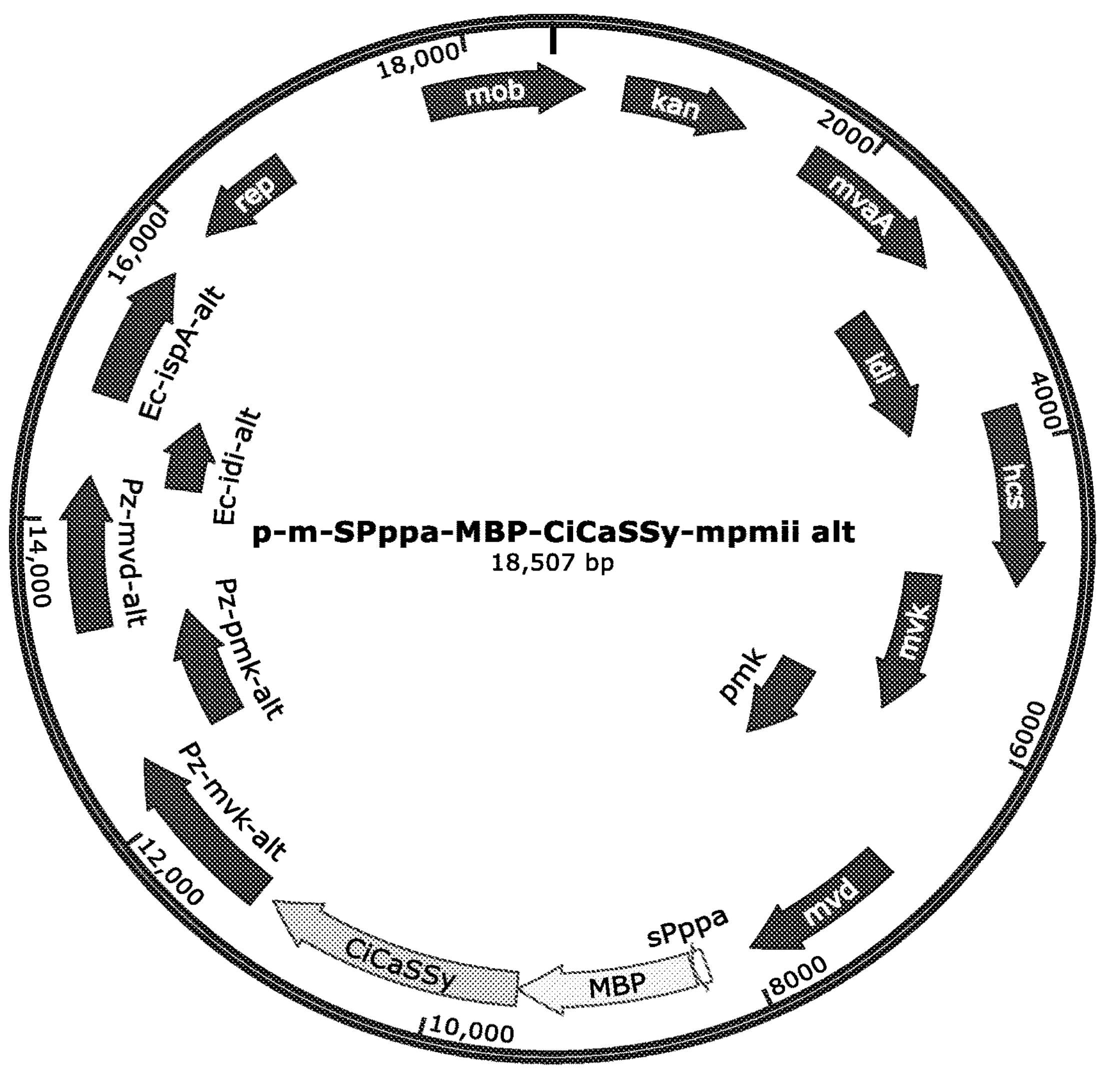

FIG. 2 Map of plasmid p-m-SPppa-MBP-CiCaSSy-mpmii alt.

Figure 3:
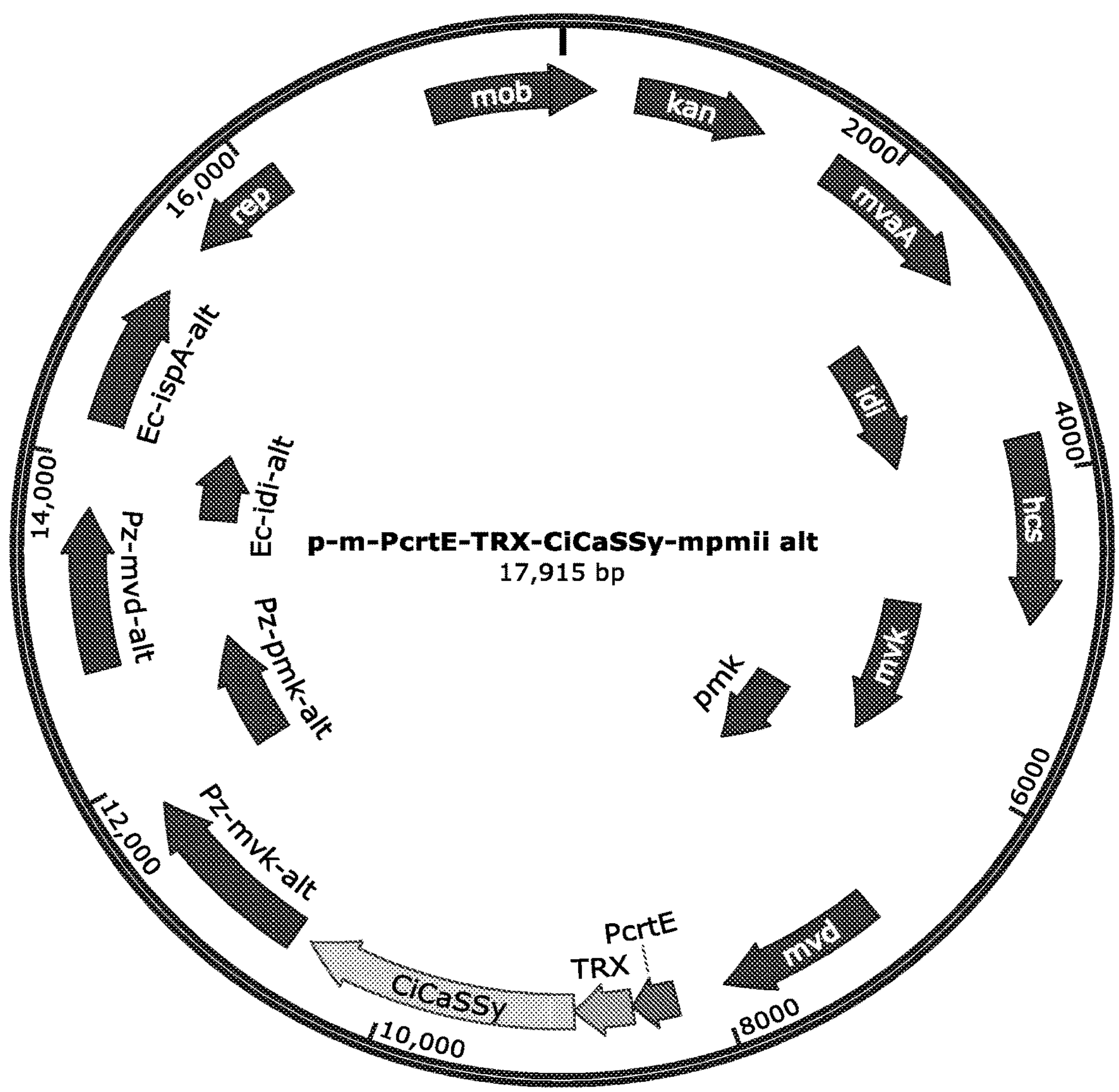

FIG. 3 Map of plasmid p-m-PcrtE-TRX-CiCaSSy-mpmii alt.

Figure 4:
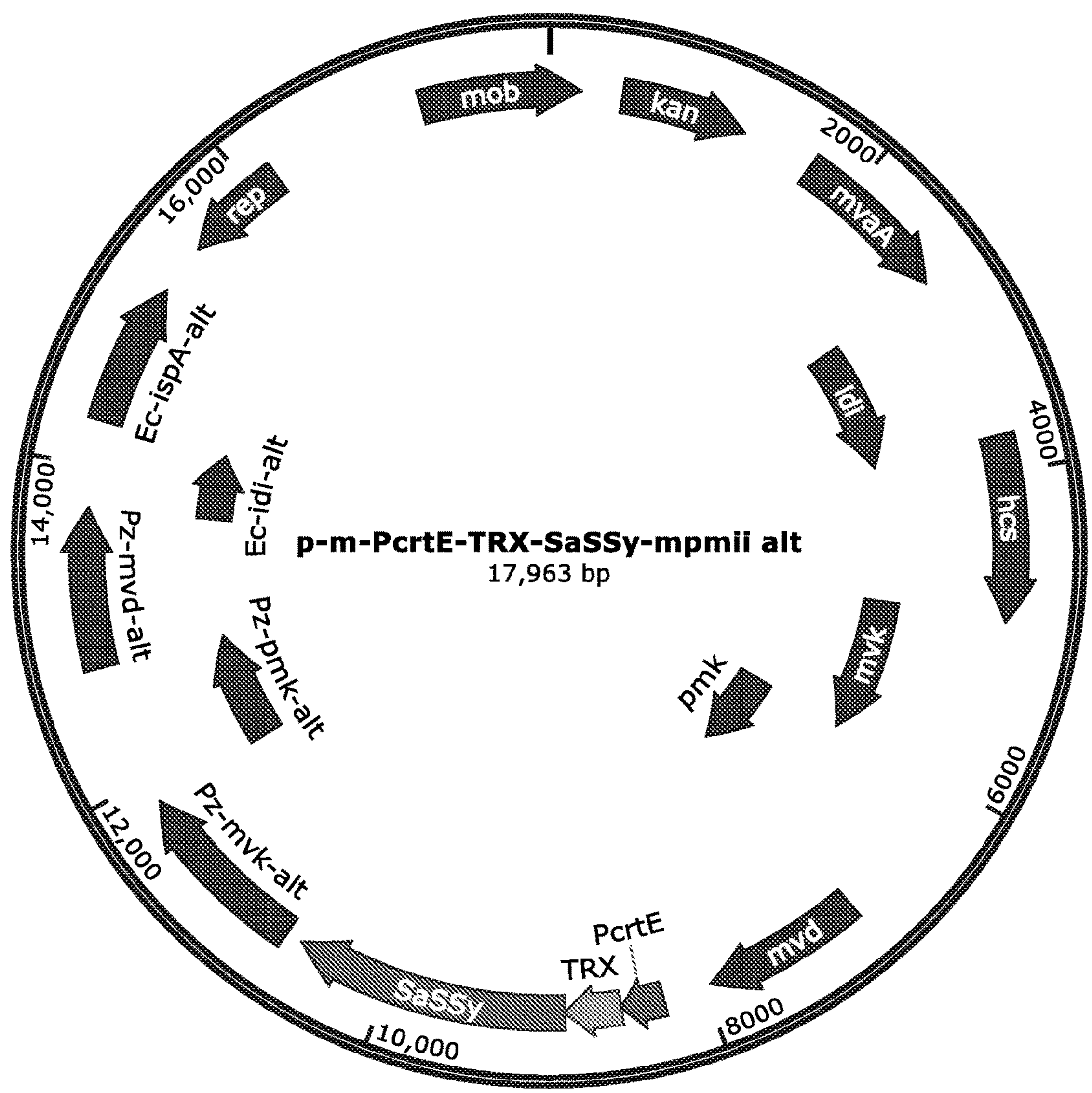

FIG. 4 Map of plasmid p-m-PcrtE-TRX-SaSSy-mpmii alt.

Figure 5:
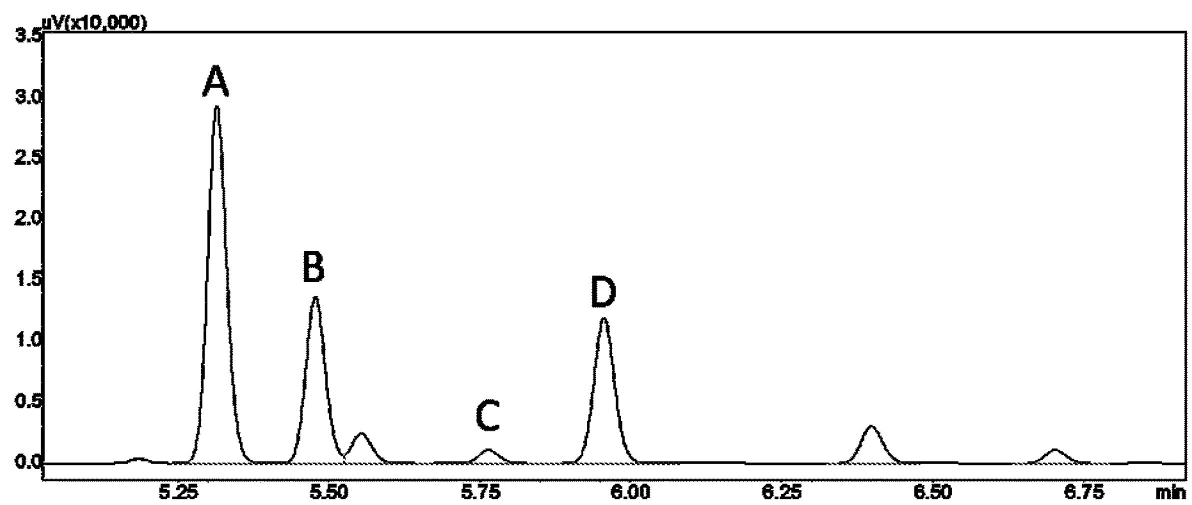

FIG. 5 GC chromatogram of terpene species produced by CiCaSSy in *R. sphaeroides*. The compounds identified by GC-MS are: α-santalene (Retention time: 5.3 min), trans-α-bergamotene (Rt: 5.45 min), epi-β-santalene (Rt: 5.75 min) and β-santalene (Rt: 5.95 min).

Figure 6:
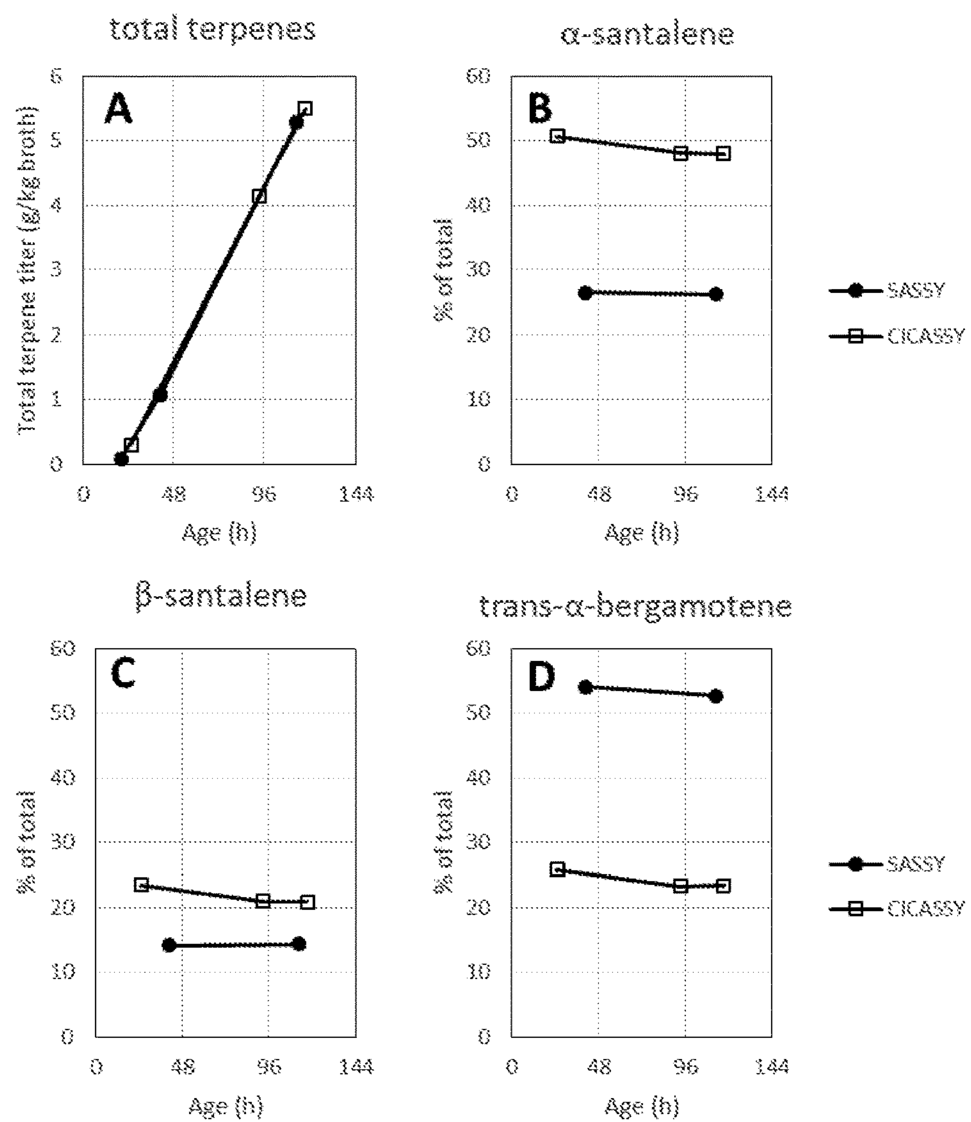

FIG. 6 Production of total terpenes (A), α-santalene (B), β-santalene (C), and trans-α-bergamotene (D) during fed-batch fermentation of *Rhodobacter sphaeroides* Rs265-9c strains harbouring plasmids with either the gene encoding SaSSy or CiCaSSy santalene synthase. The product ratios for the individual terpenes (B, C and D) are represented as the amount (area) relative to the area total of the components as indicated in the GC chromatogram of FIG. 5.

FIG. 7 Alignment of CiCaSSY with relevant proteins The CiCaSSY (TS23-3) protein sequence (SEQ ID NO: 3) was aligned to the protein sequences of its nearest variants TS23-1 (SEQ ID NO: 10) and TS23-2 (SEQ ID) NO: 11) found in *C. camphora*. The 21 out of 553 residues which were different between the protein of TS23-1 and CiCaSSY are highlighted.

Figure 8:
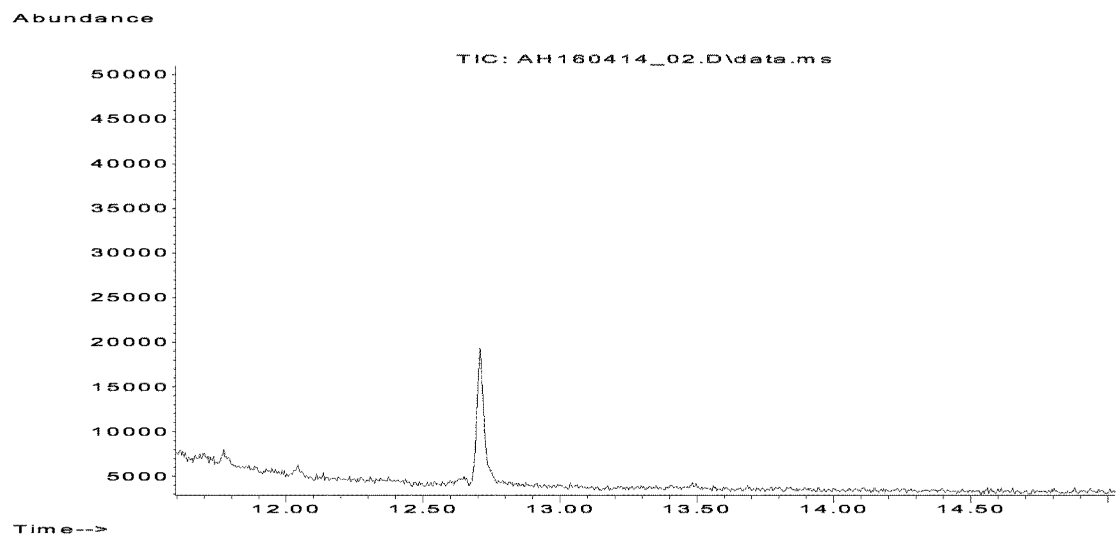

FIG. 8 GC-MS analysis of terpene production in *E. coli* (example 5), vector control sample: *E. coli* transformed with pACYCDUET.

Figure 9:
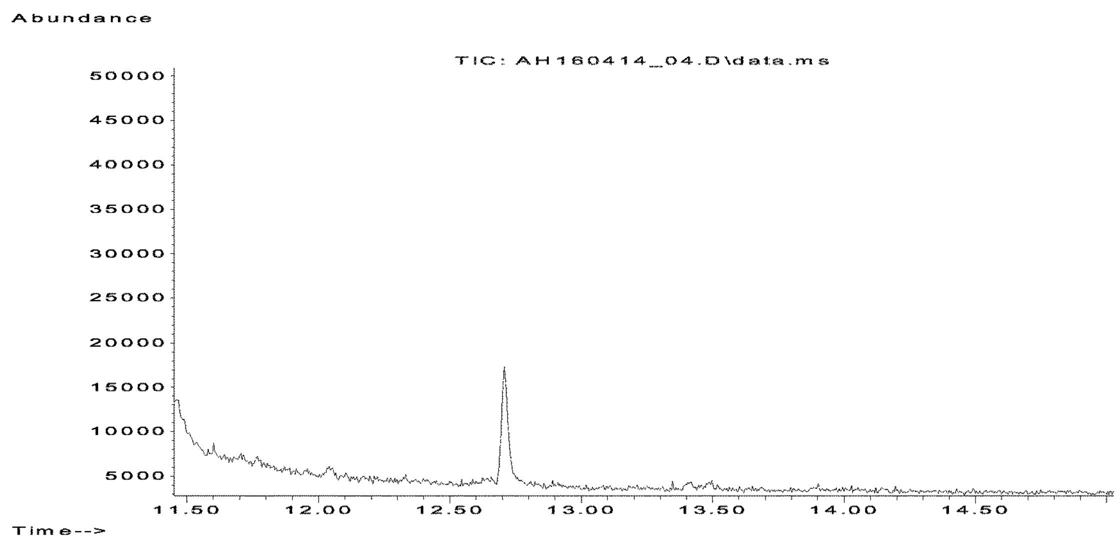

FIG. 9 GC-MS analysis of terpene production in *E. coli* (example 5), clone TS23-1 sample: *E. coli* transformed with pACYCDuet_TS23-1

Figure 10:
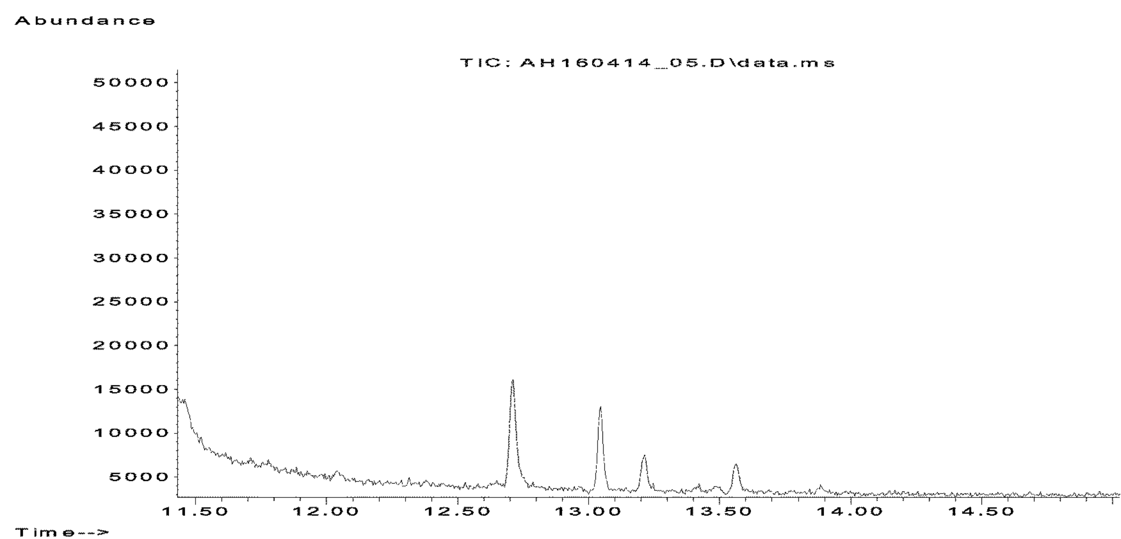

FIG. 10 GC-MS analysis of terpene production in *E. coli* (example 5), clone TS23-3 sample: *E. coli* transformed with pACYCDuet_TS23-3 (CicaSSy)

Figure 11:
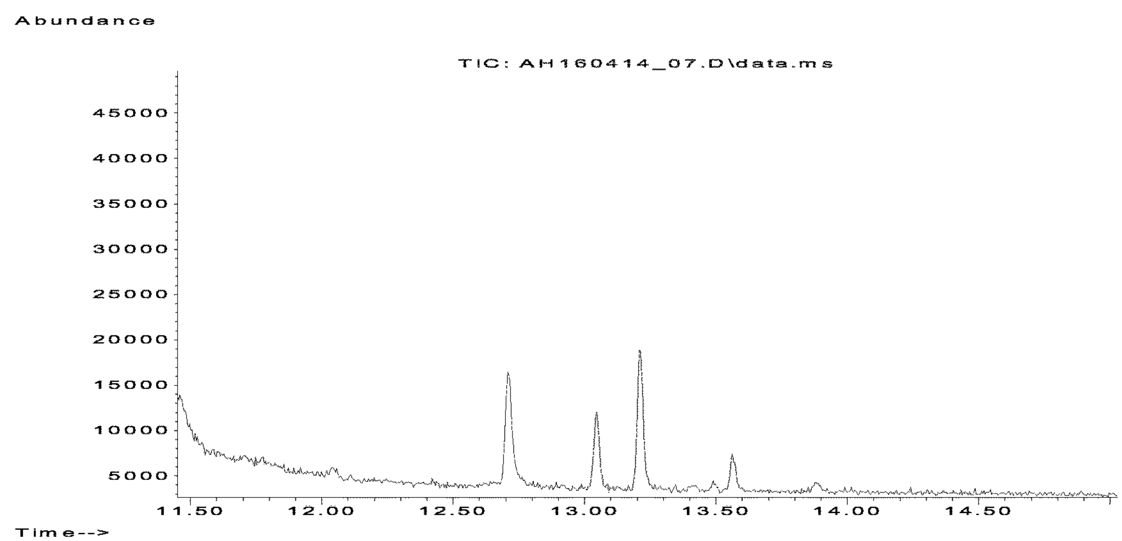

FIG. 11 GC-MS analysis of terpene production in *E. coli* (example 5), clone SaSSy sample: *E. coli* transformed with pACYCDuet_SaSSy)

EXAMPLES

Example 1

GC-MS Analysis of *Cinnamomum camphora*

A *Cinnamomum camphora* plant of about 30 cm tall was purchased from Planfor (Pépinières PLANFOR, RD 651 40090 UCHACQ—FRANCE). *Cinnamomum camphora* is known to occur in several chemotypes. In particular the cineole type appears to contain santalene (Stubbs et al., 2004, Pelissier et al., 1995), while other chemotypes (camphor, linalool) have not been reported to contain santalene (e.g. Frizzo 2000; Pino 1998). The plant was dissected in leaf, stem and root material. 0.5 g of plant material was weighed in a precooled glass tube, and 2 mL of dichloromethane was added. The suspension was vortexed for 1 min, sonicated for 5 min in an ultrasonic bath and centrifuged for 5 min at 1500 g at room temperature. The supernatant was collected and filtered over a column of 1 g sodium sulphate. About 2 μL was analysed by GC/MS using a gas chromatograph as described in detail by Cankar et al. (2015). Santalenes were identified by the comparison of retention times and mass spectra to those of sandalwood oil (Sigma-Aldrich).

Results:

The roots, leaves and stem of *C. camphora* appeared to contain compounds that correspond to α-santalene (Rt 13.17 min), α-bergamotene (Rt 13.34 min), epi-β-santalene (Rt 13.54 min) and β-santalene (Rt 13.69 min). The concentration of santalenes was highest in the roots. Other compounds found in the roots of the Cinnamomum plant were identified as guaiol, guaiadiene, intermedeol, eremoligenol, germacrene D, isolepidozene, saffrol, limonene, pinene, camphene, myrcene, sabinene, 1,8-cineol and camphor. Therefore, this tissue was further taken for extraction of RNA.

Example 2

RNA Extraction and Analysis

The RNA of *C. camphora* root material was isolated as follows: About 15 mL extraction buffer (2% hexadecyltrimethylammonium bromide, 2% polyvinylpyrrolidinone K 30, 100 mM Tris-HCl (pH 8.0), 25 mM EDTA, 2.0 M NaCl, 0.5 g/L spermidine and 2% β-mercaptoethanol) was warmed to 65° C., after which 3 g ground tissue was added and mixed. The mixture was extracted two times with an equal volume of chloroform:isoamylalcohol (1:24), and one-fourth volume of 10 M LiCl was added to the supernatant and mixed. The RNA was precipitated overnight at 4° C. and harvested by centrifugation at 10 000 g for 20 min. The pellet was dissolved in 500 μL of SSTE [1.0 M NaCl, 0.5% SDS, 10 mM Tris-HCl (pH 8,0), 1 mM EDTA (pH 8.0)] and extracted once with an equal volume of chloroform: isoamylalcohol. Two volumes of ethanol were added to the supernatant, incubated for at least 2 h at −20° C., centrifuged at 13 000 g and the supernatant removed. The pellet was air-dried and resuspended in water. Total RNA (60 μg) was shipped to Vertis Biotechnology AG (Freising, Germany). PolyA+ RNA was isolated, random primed cDNA synthesized using a randomized N6 adapter primer and M-MLV H-reverse transcriptase. cDNA was sheared and fractionated, and fragments of a size of 500 bp were used for further analysis. The cDNAs carry attached to their 5' and 3' ends the adaptor sequences A and B as specified by Illumina. The material was subsequently analysed on an Illumina MiSeq Sequencing device. In total, 27,919,287 sequences were read by the MiSeq, with a total sequence length of 10,592,407,803 basepairs. Trimmomatic-0.32 was used to trim sequences from Illumina sequencing adapters, Seqprep was used to overlap paired end sequences, and bowtie2 (version 2.2.1) was used to remove phiX contamination (phiX DNA is used as a spike-in control, usually present in <1%). Paired end reads and single reads were used in a Trinity assembly (trinityrnaseq-2.0.2). A total number of 160871 contigs were assembled by Trinity.

In order to identify sesquiterpene synthases, the *C. camphora* contigs were used to create a database of cDNA sequences. In this database, the TBLASTN program was deployed to identify cDNA sequences that encode proteins that show identity with protein sequences of sesquiterpene synthases, including santalene synthases from *Santalum album* (GenBank accession E3W202). *Clausena lansium* (ADR71055) and *Solanum habrochaites* (ACJ38409), valencene synthase from *Callitropsis nootkatensis* (CDM55287) and trans-α-bergamotene synthase from *Phyla dulcis* (AFR23371). In total 95 contigs in the *C. camphora* cDNA database were identified which have significant homology to sesquiterpene synthases. The contigs were grouped into 28 groups according to their overlap in sequence. These 28 contigs were further characterized by analyzing them using the BLASTX program to align them to protein sequences present in the UniProt database (downloaded Aug. 28, 2015), and 14 of them were identified as putative sesquiterpene synthase sequences and other 14 as putative monoterpene synthases, according to their homology to terpene synthases sequences present in UniProt.

Contigs were screened for open reading frames encoding the full-length terpene synthase proteins, based on the alignments provided by the BLASTX analysis. The following criterion for identifying a protein full length was used: both sesquiterpene synthases and monoterpene synthases carry a RRxxxxxxxxW motif (RRX8W) close to their N-terminal start. An in-frame ATG codon should map 20-70 codons upstream from the region encoding the RRX8W motiv. or its orthologous position, to be identified as a startcodon.

Example 3

Cloning of *Cinnamomum camphora* Santalene Synthase (CiCaSSy)

Full length open reading frames were amplified from the cDNA of *C. camphora*. Forward and reverse primers as shown in Table 1 were designed and used to amplify total open reading frames in such a way that the reading frame was fused to the C-terminus of a His-6 tag in the plasmid pCDF-DUET-1 (Novagen corporation). A total of 37 different terpene synthase ORFs were cloned. Using the primers TS23fw and TS23re (Table 1), three different closely related cDNAs were obtained, which encoded proteins with SEQ ID NO:10 (TS23-1), SEQ ID NO:11 (TS23-2), and SEQ ID NO:3 (T523-3).

TABLE 1

| name | Sequence | clones |
|---|---|---|
| TS23 fw | atatggatcctATGGACTCCATGGAGGTACGCCGTCTG (SEQ ID NO: 8) | TS23-1, TS23-2, |
| TS23 re | atatgcggccgcTCATCCCAAGTTGATGGATTCCTTCAATGGCACTG (SEQ ID NO: 9) | TS23-3 |

The cloned variants were analysed by sequencing the TS insert. Different variants were introduced into chemical competent *E. coli* BL21-RIL (Stratagene), by heat shock transformation, and selected on LB-agar with 1% glucose, 50 ug/ml spectinomycin and 50 ul/ml chloramphenicol. Transformants were transferred to 5 ml LB liquid medium with 1% glucose 50 ug/ml spectinomycin and 50 ug/ml chloramphenicol and grown overnight at 37° C. and 250 rpm.

200 μL of those cultures was transferred to 20 mL of LB medium with the appropriate antibiotic in a 100 mL Erlenmeyer flask, and incubated at 37° C., 250 rpm until the A600 was 0.4 to 0.6. Subsequently, 1 mM IPTG was added and cultures were incubated overnight at 18° C. and 250 rpm. The next day, cells were harvested by centrifugation (10 min 8000×g). medium was removed, and cells were resuspended in 1 mL Resuspension buffer (50 mM Tris-HCl pH=7.5, 1.4 mM β-mercaptoethanol; 4° C.). Cells were disrupted by shaking 2 times for 10 seconds with 0.2 g zirconium sand in a Fastprep machine at speed 6.5. Insoluble particles were subsequently removed by centrifugation (10 min 13,000×g, 4° C.). Soluble protein was immediately used for enzyme assays.

Example 4

In Vitro Enzyme Assay

For enzyme assays, in a glass tube a mix was made of 800 μL of MOPSO buffer (15 mM MOPSO (3-[N-morpholino]-2-hydroxypropane sulphonic acid) pH=7.0, 12.5% glycerol, 1 mM MgCl2. 0.1% tween 20, 1 mM ascorbic acid, 1 mM dithiothreitol). 100 μL of purified enzyme solution and 5 μL of farnesyl diphosphate or geranyl diphosphate (10 mM, Sigma FPP dry-evaporated and dissolved in 50% ethanol) and 20 μL Na-orthovanadate 250 mM. This mix was incubated at 30° C. with mild agitation for 2 hours. Subsequently, the water-phase was extracted with 2 mL ethylacetate. Ethylacetate phase was collected, centrifuged at 1200× g, dried over a sodium sulphate column and analyzed by GC-MS.

The GC-MS analysis was performed on an Agilent Technologies system, comprising a 7980A GC system, a 597C inert MSD detector (70 eV), a 7683 auto-sampler and injector and a Phenomenex Zebron ZB-5 ms column of 30 m length×0.25 mm internal diameter and 0.25 μm stationary phase, with a Guardian precolumn (5 m). In this system, 1 μL of the sample was injected. The injection chamber was at 250° C., the injection was splitless, and the ZB5 column was maintained at 45° C. for 2 minutes after which a gradient of 10° C. per minute was started, until 300° C. Peaks were detected in chromatograms of the total ion count. Compounds were identified by their retention index and by their mass spectrum in combination with comparison of the mass spectrum to libraries (NIST8 and in-house).

Clone TS23-3 (SEQ ID NO: 3) was found to produce Santalenes in this in vitro assay, and thus to encode a santalene synthase, and was termed CiCaSSY.

The closely related clones TS23-1 (SEQ ID NO: 10) and TS23-2 (SEQ ID NO: 11) did not produce any santalenes or other sesquiterpenes in the in vitro assay.

Example 5

Expression of santalene synthase in *E. coli*

For the production of sesquiterpenes in *E. coli*, the terpene synthase has to be provided with the substrate FPP. Cicassy was therefore co-expressed with a plasmid containing all genes necessary for the synthesis of FPP (pBbA5c-MevT-MBIS-NPtII). This plasmid is a variant of plasmid pBbA5c-MevT(CO)-MBIS(CO, IspA) (Peralta-Yalta et al., 2011), in which the chloramphenicol resistance marker has been exchanged for a kanamycin resistance marker (NptII). From this plasmid, a 728 basepair fragment ranging from the ApaI site to the start of the chloramphenicol acyltransferase (CAT) was amplified using Phusion polymerase and primers P7 GCTGTTAGCGGGCCCATTAAG (SEQ ID NO: 12) and P2 GATATTCTCATTTTAGCCATTTTAGCTTCCTTAGCTCCTG (SEQ ID NO: 13). and the neomycin phosphotransferase II (NptII) gene from pBINPlus (van Engelen 1995) by using primers P5 CAGGAGCTAAGGAAGCTAAAATGGCTAAAATGAGAATATC (SEQ ID NO: 14) and P6 CCAAGCGAGCTCGATATCAAACTA_AAACAATTCATCCAG (SEQ ID NO: 15). Fragments were isolated from gel and used as template for a fusion PCR, using primers PG and P7 and amplified a 1524 bp fusion fragment. This fragment, and pBbA5c-MevT(CO)-MBIS(CO, IspA) were both digested with ApaI and SacI restriction enzymes, and the vector fragment of pBbA5c-MevT(CO)-MBIS(CO) and the digested fusion PCR fragment were ligated and transformed into *E. coli* DH5alpha by electroporation, and recombinant colonies were selected on LB+kanamycin. Presence of the genetic elements including the MEV pathway operon and the NptII gene was confirmed by isolating miniprep plasmid DNA and analysis of this DNA by digestion with ApaI and SacI, yielding bands of approximately 12000 bp and 1500 bp. The resulting plasmid was called pBbA5Sc-MevT-MBIS-NptII.

In addition, the 1670 bp BamHI NotI fragment of pCDF-DUET-1 vector in which CiCaSSY had been cloned was transferred to pACYC-DUET-1 (Novagen corporation), for a fair comparison to SaSSY, which had also been introduced in pACYC-DUET-1 in this way.

First plasmid pBbA5c-MevT-MBIS-NPtII was transformed by heat shock to commercially available competent BL21DE3 cells (New England Biolabs cat C2527). Transformants were selected on LB plates containing kanamycin 50 ug/ml and glucose 1%.

A pBbA5c-MevT-MBIS-NPtII transformant was grown and competent cells were made with the $CaCl_2$ method. Briefly, 10 ml culture of this transformant in LB+1% glucose+50 ug/ml Kanamycin was grown until A600=0.5. Subsequently, cells were centrifuged at 8000×g for 5 min, resuspended in 1 ml ice-cold 100 mM $CaCl_2$, centrifuged again for 5 minutes at 8000×g, supernatant was discarded and cells were resuspended in 1 ml ice-cold 100 mM $CaCl_2$ and 50 ul of these cells were used for transformation. The cells were transformed by heat-shock with 50 ng of plasmids pACYCDuet, pACYCDuet_TS23-1, pACYCDuet_CicaSSy and pACYCDuet_Sassy. Transformants were selected on LB plates containing kanamycin 50 ug/ml, chloroamphenicol 50 ug/ml and glucose 1%.

A tube with 5 ml LB medium with kanamycin 50 ug/ml, chloroamphenicol 50 ug/ml and glucose 1% was inoculated with a colony containing both plasmids and grown overnight at 37° C. The overnight culture was used to inoculate 20 ml LB plus antibiotics (but no glucose) to an OD of 0.1. The culture was grown to OD 0.45-0.55 and then induced with 20 ul 1M IPTG. The culture was overlaid with 2 ml of dodecane to prevent evaporation of sesquiterpenes from the flask and grown overnight at 28° C. and 250 rpm.

For GC-MS analysis the dodecane was separated from the culture by centrifugation and diluted 200 times with ethyl acetate. 2 μL were analysed by GC/MS using a gas chromatograph as described in detail by Cankar et al. (2015).

Ts23-1 did not produce a detectable amount of any terpene in this system (FIG. 9). The major product of SaSSY in this system was found to be trans α-bergamotene (FIG. 11); the major product of CiCaSSY was found to be α-santalene (FIG. 10).

Example 6

RS102 Medium 20 g/L Yeast extract (Gistex, DSM) and 0.5 g/L NaCl are dissolved in distilled water, pH is brought to 7.4 with NaOH, distilled water is added to a volume of 930 ml, and the medium is steam sterilised.

One ml of sterile 0.5 g/ml $MgSO_4$-$7H_2O$, 2 ml of sterie filtered microelements (80 g/L $(NH_4)_2Fe(SO_4)_2$-$6H_2O$; 6 g/L $ZnSO_4$-$7H_2O$; 2 g/L $MnSO_4$—$H_2O$; (0.2 g/L $NiSO_4$-$6H_2O$, optionally); 2 g/L Vitamin C), and 2 ml of autoclaved CaFe solution (75 g/L $CaCl_2$-$2H_2O$; 5 g/L $FeCl_3$-$6H_2O$; 3.75 ml HCl (37%)) and 66 ml of glucose solution are added to the sterilised medium, Example 7

Bacteria and Culture Conditions

*Rhodobacter sphaeroides* strain Rs265-9c was obtained from *Rhodobacter sphaeroides* strain ATCC 35053 [purchased from the American Type Culture Collection (ATCC—Manassas, Va., USA—www.atcc.org); number 35053; *Rhodobacter sphaeroides* (van Niel) Imhoff et al., isolated from a sewage settling pond in Indiana and deposited as *Rhodopseudomonas sphaeroides* van Niel] after two rounds of mutagenesis and was used as the base host for construction of recombinant strains having improved production of santalene. All *R. sphaeroides* strains were grown at 30° C. in medium RS102 unless otherwise stated.

*E. coli* strains were grown at 37° C. in LB medium (Becton Dickinson, Sparks, Md., USA). For maintenance of plasmids in recombinant *E. coli* and *R. sphaeroides* strains, ampicillin (100 mg/L), chloramphenicol (30 mg/L) and/or neomycin (25-50 mg/L, depending on the plasmid) were added to the culture medium. Liquid cultures were routinely grown aerobically in a rotary shaker. When solid media were required, agar (1.5% final concentration) was added.

Example 8

Cloning of Santalene Synthase (CiCaSSy) and Construction of Plasmid p-m-LPppa-CiCaSSy-mpmii alt For the expression of *Cinnamomum camphora* santalene synthase in *R. sphaeroides*, the full length ORF was custom synthesised and optimised in terms of codon usage for *R. sphaeroides* by Genscript USA Inc. (Piscataway, N.J., USA). Additionally, the sequence for the promoter LPppa was added at the 5' of the gene (SEQ ID NO:2). The construct was delivered cloned into plasmid pUC57. The complete construct was excised from the plasmid using the restriction enzymes EcoRI and BamHI (at the 5' and 3', respectively). The fragment containing the promoter and the gene (1758 bp) was ligated to the p-m-mpmii alt vector previously digested with the same two restriction enzymes. The ligation mixture was transformed into *E. coli* 517-1 cells. Transfer of p-m-LPppa-CiCaSSy-mpmii alt (FIG. 1) from S17-1 to *R. sphaeroides* Rs265-9c by conjugation was performed using standard procedures (Patent U.S. Pat. No. 9,260,709B2). The nucleotide sequence of the construct LPppa-CiCaSSy is given in SEQ ID NO:2; the protein sequence is represented in SEQ ID NO:3.

Example 9

Construction of plasmid p-m-SPppa-MBP-CiCaSSy-mpmii alt

For the expression of the CiCaSSy gene in combination with the MBP tag under the regulation of promoter SPppa, the construct SPppa-MBP was synthesized by Genscript USA Inc. (Piscataway, N.J., USA). The gene coding MBP was codon optimized for the expression in *R. sphaeroides*. The construct SPppa-MBP was then fused to the CiCaSSy sequence and cloned in the p-m-mpmii alt vector previously digested with EcoRI and Band-H. Briefly, the construct SPppa-MBP was amplified using the primers 5'-CTGTCCATGATCTTGTCGTCGTC-3' (SEQ ID NO): 16) and 5'-CTGGCCTCAGAATTCAAATTTATTTGCTTTGTGAGCCCATAAC-3' (SEQ ID NO: 17), and CiCaSSy was amplified with primers 5'-CAAGATCATGGACAGCATGCTC-3' (SEQ ID NO: 18) and 5'-TTTATGATTTGGATCCTCAGCCCAGGTT-3' (SEQ ID NO: 19). The amplicons and the digested vectors were then assembled using the InFusion® enzyme mix from Clontech. The reaction mixture was transformed into *E. coli* S17-1 cells. Transfer of p-m-SPppa-MBP-CiCaSSy-mpmii alt (FIG. 2) from S17-1 to *R. sphaeroides* Rs265-9c by conjugation was performed using standard procedures (U.S. Pat. No. 9,260,709B2). The nucleotide sequence of the construct SPppa-MBP-CiCaSSy is given in SEQ ID NO:4; the protein sequence is represented in SEQ ID NO:5.

Example 10

Construction of plasmid p-m-PcrtE-TRX-CiCaSSy-mpmii alt For the expression of the CiCaSSy gene in combination with the TRX tag under the regulation of promoter PcrtE, the construct PcrtE-TRX was synthesized by Genscript USA Inc. (Piscataway, N.J., USA). The gene coding TRX from *E. coli* was codon optimized for the expression in *R. sphaeroides*. The construct PcrtE-TRX was then fused to the CiCaSSy sequence and cloned in the p-m-mpmii alt vector previously digested with EcoRI and BamHI. Briefly, the construct PcrtE-TRX was amplified using the primers 5'-CTGTCCATAATCTTGTCGTCGTCAT-3' (SEQ ID NO: 20) and 5'-ACTGGCCTCAGATTCCCTCTGCTGAACG-3' (SEQ ID NO: 21), and CiCaSSy was amplified with primers 5'-CAAGATTATGGACAGCATGGAAGTCC-3' (SEQ ID NO: 22) and 5'-TTTATGATTTGGATCCTCAGCCAGGTT-3' (SEQ ID NO: 23). The amplicons and the digested vectors were then assembled using the InFusion® enzyme mix from Clontech. The reaction mixture was transformed into *E. coli* S17-1 cells.

Transfer of p-m-PcrtE-TRX-CiCaSSy-mpmii alt (FIG. 3) from S17-1 to *R. sphaeroides* Rs265-9c by conjugation was performed using standard procedures (U.S. Pat. No. 9,260,709B2).

The nucleotide sequence of the construct PcrtE-TRX-CiCaSSy is given in SEQ ID NO:6; the protein sequence is represented in SEQ ID NO:7

Example 11

Construction of Plasmid p-m-PcrtE-TRX-SaSSy-mpmii alt

For the expression of *Santalum album* santalene synthase (SaSSy) in *R. sphaeroides* in combination with the TRX tag under the regulation of promoter PcrtE, the full length ORF together with the TRX from *E. coli* was custom synthesised and optimised in terms of codon usage for *R. sphaeroides* by Genscript USA Inc. (Piscataway, N.J., USA). Additionally, the sequence for the promoter PcrtE was added at the 5' of the gene (SEQ ID NO: 24). The construct was delivered cloned into plasmid pUC57. The complete construct was excised from the plasmid using the restriction enzymes EcoRI and BamHI (at the 5' and 3', respectively). The fragment containing the promoter and the genes (2335 bp) was ligated to the p-m-mpmii alt vector previously digested with the same two restriction enzymes. The ligation mixture was transformed into *E. coli* S17-1 cells.

Transfer of p-m-PcrtE-TRX-SaSSy-mpmii alt (FIG. 4) from S17-1 to *R. sphaeroides* Rs265-9c by conjugation was performed using standard procedures (U.S. Pat. No. 9,260,709B2).

The nucleotide sequence of the construct PcrtE-TRX-SaSSy is given in SEQ ID NO: 24; the protein sequence is represented in SEQ ID NO: 25.

Example 12

Growth conditions shake flasks Seed cultures were performed in 100 ml shake flasks without baffles with 20 ml RS102 medium with 100 mg/L neomycin and a loop of glycerol stock. Seed culture flasks were grown for 72 hours at 30° C. in a shaking incubator with an orbit of 50 mm at 110 rpm.

At the end of the 72 hours, the OD600 of the culture was assessed in order to calculate the exact volume of culture to be transferred to the larger flasks.

Shake flask experiments were performed in 300 ml shake flasks with 2 bottom baffles. Twenty nil of RS102 medium and neomycin to a final concentration of 100 mg/L were added to the flask together with 2 ml of sterile n-dodecane. The volume of the inoculum was adjusted to obtain a final OD600 value of 0.05 in 20 ml medium. The flasks were kept for 72 hours at 30° C. in a shaking incubator with an orbit of 50 mm at 110 rpm. Shake flask experiments were performed in duplicates.

Example 13

Sample Preparation for Analysis of Isoprenoid Content in Organic Phase

Cultures were collected 72 hours after inoculation in pre-weighted 50 ml PP tubes which were then centrifuged at 4500×g for 20 minutes. The n-dodecane layer was transferred to a microcentrifuge tube for later GC analysis.

Ten microliters of ethyl laureate were weighed in a 10-ml glass vial to which 800 μl of the isolated dodecane solution were added and weighed. Subsequently, 8 ml of acetone were added to the vial to dilute the dodecane concentration for a more accurate GC analysis. Approximately, 1.5 ml of the terpene-containing dodecane in acetone solution were transferred to a chromatography vial.

Example 14

Gas Chromatography

Gas chromatography was performed on a Shimadzu GC2010 Plus equipped with a Restek RTX-5Sil MS capillary column (30 m×0.25 mm, 0.5 μm). The injector and FID detector temperatures were set to 280° C. and 300° C., respectively. Gas flow through the column was set at 40 ml/min. The oven initial temperature was 160° C., increased to 180° C. at a rate of 2° C./min, further increased to 300° C. at a rate of 50° C./min, and held at that temperature for 3 min. Injected sample volume was 1 μL with a 1:50 split-ratio, and the nitrogen makeup flow was 30 ml/min Example 15

Analysis of Terpenes Produced by CiCaSSy in *R. sphaeroides*

FIG. 5 shows the chromatogram obtained by analysing the organic phase isolated from all *R. sphaeroides* cultures expressing the CiCaSSy gene (strains from example 9. 10 and 11). Four principal compounds were identified: α-santalene (A), trans-α-bergamotene (B), epi-β-santalene (C) and β-santalene (B). The most abundant terpene was α-santalene, followed by trans-α-bergamotene and β-santalene. Since no purified santalenes are available to be used as standards, the terpene titre was calculated based on the GC response factor obtained with the terpene valencene. The total terpene production (cumulative area under the curve for all 4 terpenes) obtained in the strains from example 9, 10 and 11 are 5.3±0.12 g/kg dodecane, 5.8±0.29 g/kg dodecane and 3.4±0.09 g/kg dodecane, respectively. The ratio for the four terpene species was conserved in all the strains.

Example 16

Seed Medium for Fed-Batch Cultivation

The following components were dissolved in 1 L of water: 20.8 g yeast extract, 10.3 g $MgSO_4.7SO_4.7H_2O$, 86 mg $ZnSO_4.7H_2O$, 30 mg $MnSO_4.H_2O$, 1.1 g $CaCl_2.2H_2O$, 0.96 g $FeSO_4.7H_2O$, 1.44 g $KH_2PO_4$, and 1.44 g $K_2HPO_4$. The pH was adjusted to 7.4 with 10 M NaOH. After sterilisation (121° C., 20 min), 50 ml of 50% (w/w) glucose, and 1 ml of 0.1 mg/ml Neomycin sulfate is added per liter of medium.

Example 17

Medium for Fed-Batch Cultivation

The following components were dissolved in 1 L of water: 25 g Yeast extract. 1.7 g $MgSO_4.7H_2O$, 0.10 g $ZnSO_4.7H_2O$, 35 mg $MnSO_4.H_2O$, 1.3 g $CaCl_2.2H_2O$, 0.17 g $FeCl_3.6H_2O$, 1.7 g $K_2HPO_4$, 1.7 $KH_2PO_4$, 1.1 g $(NH_4)_2Fe(SO_4)_2.6H_2O$, 2.8 g $(NH_4)_2SO_4$, 1.1 g $(NH_4)H_2PO_4$, 1.9 g $MgCl_2.6H_2O$, and 1 mL antifoam.

After sterilisation (121° C., 20 min), the pH is adjusted to 7.0 with 25% Ammonium hydroxide solution. Per liter of sterile medium, 60 mL of 50% (w/w) glucose. 1 ml of 0.1 mg/ml Neomycine sulfate, 4 mg Niacin, 8 mg Thiamin.HCl. 4 mg Nicotinamide, 0.2 mg Biotin, and 150 mL of n-dodecane were added.

Example 18

Cultivation Conditions Fed-Batch Fermentation

Seed cultures for the fed-batch cultivations were prepared by inoculation of 500 ml of sterile seed medium (example 16) by adding 1 ml of glycerol stock of the appropriate *Rhodobacter sphaeroides* strain, and incubation for 48 hours at 30° C.

In a 1 L fermenter vessel. 350 mL of fed-batch medium was sterilized and supplemented with (filter) sterilized glucose, Neomycin, vitamins, and n-dodecane as indicated (example 17). By addition of 50 ml of seed culture, the medium was inoculated and incubated for approximately 24 hours at 30° C., agitation of 600 rpm, air flow of 0.3 vvm, and a pH of 7 (adjusted by automated addition of 12.5% Ammonium hydroxide solution). After 24 hours, the agition was increased to 1200 rpm, and 450-500 g of 50 (w/w) % glucose was fed to the fermenter within 100 hours.

Example 19

GC Sample Preparation Fed-Batch Fermentation

Broth samples of approximately 20 mL were collected during a fed-batch cultivation. Ten microliters of ethyl laureate were weighed in a 10 ml glass vial to which 0.8 ml of broth sample added and weighed. Subsequently, 8 ml of acetone were added to the vial and the aceton-broth mixture was incubated at room temperature for 25 minutes while shaken at 400 rpm. Approximately 1.5 ml of the terpene-containing aceton-broth mixture was transferred to a chromatography vial and used for analysis according to example 14.

Example 20

Comparison of Terpene Production by *Rhodobacter spaeroides* Strains Harbouring CiCassy and SaSSy

*Rhodobacter spaeroides* strains harbouring either CiCaSSy (p-m-SPppa-MBP-CiCaSSy-mpmii alt, example 10) or SaSSy (p-m-PcrtE-TRX-CiCaSSy-mpmii alt, example 11) were cultivated in fed-batch mode according to example 18. Samples were withdrawn from the fermentation broth at various time points and were analyzed for the production of terpenes according to example 19 and 14. The concentration of total terpenes produced (cumulative areas of the peaks A-D in FIG. 5) were nearly equal for both strains throughout the cultivation (FIG. 6A), and a final terpene concentration of approximately 5.5 g/kg of broth was obtained. Throughout 120 hours of fed-batch cultivation, the terpenes produced by the CiCaSSy strain consisted of approximately 49% of α-santalene (FIG. 6B), 21% of β-santalene (FIG. 3C), and 25% of trans-α-bergamotene (FIG. 6D), whereas the SaSSy strain produced approximately 28% of α-santalene (FIG. 6B), 14% of β-santalene (FIG. 6C), and 52% of trans-α-bergamotene (FIG. 6D). The percentage of α-santalene and β-santalene produced by the CiCaSSy strain were respectively 1.8 fold and 1.5 fold higher than that of the SaSSy strain. In contrast, the trans-α-bergamotene fraction produced by the CiCaSSy strain was 2 fold lower than that of the SaSSy strain.

REFERENCES

Amick, J. D., Julien, B. N., 2015. Modified Santalene synthase polypeptides, encoding nucleic acid molecules and uses thereof. WO/2015/153501

Baldovini, N., Delasalle, C., Joulain, D., 2011. Phytochemistry of the heartwood from fragrant *Santalum* species: a review. *Flavour Fragr. J.* 26, 7-26.

Cankar, Jongedijk, Klompmaker, Majdic, Mumm, Bouwmeester, Bosch & Beekwilder (2015) (+)-Valencene production in *Nicotiana benthamiana* is increased by down-regulation of competing pathways. Biotechnol. J. 10. 180-189

Chapuis, C., 2012. Intermediates for the preparation of Beta-Santalol. WO/2012/110375

Daviet, L., ROCCI, L., and Schalk, M. (2015). Method for producing fragrant alcohols. (WO2015040197)

Diaz-Chavez, M. L., Moniodis, J., Madilao, L. L., Jancsik, S., Keeling, C. I., Barbour, E. L., Ghisalberti, E. L., Plummer, J. A., Jones, C. G., Bohlmann, J., 2013. Biosynthesis of Sandalwood Oil: *Santalum album* CYP76F Cytochromes P450 Produce Santalols and Bergamotol. PLoS ONE 8.

Frizzo, Caren D. et al. Essential oils of camphor tree (*cinnamomum camphora* nees & eberm) cultivated in Southern Brazil. Braz. arch. biol. technol. [online]. 2000, vol. 43, n. 3 [cited 2016-02-26], pp. 313-316.

Jones C G, Moniodis J, Zulak K G, Scaffidi A, Plummer J A, Ghisalberti E L, Barbour E L, Bohlmann J. (2011) Sandalwood fragrance biosynthesis involves sesquiterpene synthases of both the terpene synthase (TPS)-a and TPS-b subfamilies, including santalene synthases. J Biol Chem. 286(20):17445-54. Ngo, K.-S., and Brown, G. D. (2000). Autoxidation of α-santalene. Journal of Chemical Research 2000, 68-70.

Pelissier, Y., Chantal, M., Prunac, S., Bessiere, J. 1995. Volatile components of leafs, stem and bark of *Cinnamomum camphora* Nees et Ebermaier. *J. Essent. Oil Res.* 7, 313-315.

Peralta-Yahya P P, Ouellet M, Chan R, Mukhopadhyay A, Keasling J D, Lee T S. (2011) Identification and microbial production of a terpene-based advanced biofuel. Nat Commun. 2:483.

Pino J A & Fuentes V. 1998, Leaf Oil of *Cinnamomum camphora* (L.) J. Presl. from Cuba. Journal of Essential Oil Research 10, 531-532

Schalk, M., 2016. Method for producing α-santalene. U.S. Pat. No. 9,297,004.

Schalk, M., 2014. Method for producing beta-santalene. EP2376643.

Schalk, M., 2006. Novel sesquiterpene synthases and methods of their use. WO/2006/13452.

Stubbs, B. J., Specht, A., and Brushett, D. 2004. The Essential Oil of *Cinnamomum camphora* (L.) Nees and Eberm.—Variation in Oil Composition Throughout the Tree in Two Chemotypes from Eastern Australia. *Journal of Essential Oil Research* 16, 9-14.

Teixeira da Silva, J. A., Kher, M. M., Soner, D., Page, T., Zhang, X., Nataraj, M., Ma, G., 2016. Sandalwood: basic biology, tissue culture, and genetic transformation. *Planta* 243, 847-887.

van Engelen F A, Molthoff J W, Conner A J, Nap J P, Pereira A, Stiekema W J. (1995) pBINPLUS: an improved plant transformation vector based on pBIN19. Transgenic Res. 4(4):288-90.

Willis, B. J., Eilerman, R. G., Christenson, P. A., and Yurecko Jr., J. M. 1985. Functionalization of terminal tri-substituted alkenes and derivatives thereof. U.S. Pat. No. 4,510,319

Zulak, K., Jones, C., Moniodis, J., Bohlmann, J., 2016. Terpene synthases from *Santalum*. U.S. Pat. No. 9,260,728.

The invention claimed is:

1. A santalene synthase comprising a functional homologue of an amino acid sequence as shown in SEQ ID NO: 3 An isolated santalene, said homologue being a santalene synthase comprising an amino acid sequence which has a sequence identity of at least 95% with SEQ ID NO: 3, wherein said functional homologue does not have 100% identity with SEQ ID NO: 3.

2. The santalene synthase according to claim 1, having at least 98% sequence identity with SEQ ID NO: 3.

3. A nucleic acid, comprising a heterologous nucleic acid sequence encoding the santalene synthase according to claim 1.

4. The nucleic acid according to claim 3, wherein the nucleic acid comprises a nucleic acid sequence having a sequence identity of at least 95% with a sequence shown in SEQ ID NO: 1 or SEQ ID NO: 2, or the complementary sequence thereof.

5. An expression vector comprising a nucleic acid sequence encoding a santalene synthase comprising an amino acid sequence as shown in SEQ ID NO: 3 or a functional homologue thereof, said homologue being a santalene synthase comprising an amino acid sequence which has a sequence identity of at least 95% with SEQ ID NO: 3.

6. A host cell, which may be an organism per se or part of a multi-cellular organism, said host cell comprising an expression vector comprising a heterologous nucleic acid sequence encoding a santalene synthase comprising an amino acid sequence as shown in SEQ ID NO: 3 or a functional homologue thereof, said homologue being a santalene synthase comprising an amino acid sequence which has a sequence identity of at least 95% with SEQ ID NO: 3.

7. The host cell according to claim 6, wherein the host cell is a bacterial cell selected from the group of Gram negative bacteria.

8. The host cell according to claim 6, wherein the host cell is a fungal cell selected from the group of *Aspergillus, Blakeslea, Penicillium, Phaffia Xanthophyllomyces, Pichia, Saccharomyces*, and *Yarrowia*.

9. A transgenic plant or culture comprising transgenic plant cells, said plant or culture comprising the host cell according to claim 6, wherein the host cell is of a transgenic plant selected from *Nicotiana* spp, *Solanum* spp, Cichorum *intybus, Lactuca sativa*, Mentha spp, *Artemisia annua*, and *Physcomitrella patens.*

10. A transgenic mushroom or culture comprising transgenic mushroom cells, said mushroom or culture comprising the host cell according to claim 6, wherein the host cell is selected from *Schizophyllum, Agaricus* and Pleurotis.

11. A method for preparing santalene in a transformed host cell, a transgenic plant or plant culture, or a mushroom or mushroom culture, comprising converting a farnesyl diphosphate to santalene in the presence of a recombinant santalene synthase comprising an amino acid sequence as shown in SEQ ID NO: 3 or a functional homologue thereof, said homologue being a santalene synthase comprising an amino acid sequence which has a sequence identity of at least 95% with SEQ ID NO: 3.

12. The method for preparing santalene according to claim 11, wherein the santalene is prepared in a host cell, a transgenic plant or plant culture, or a mushroom or mushroom culture, expressing said santalene synthase.

13. The method according to claim 11, further comprising isolating the santalene.

14. The method according to claim 11, wherein the ratio α-santalene to α-bergamotene ratio is higher than 1.

15. The method according to claim 11, wherein the β-santalene to α-bergamotene ratio is higher than 0.5:1.

16. The method according to claim 11, wherein the ratio of santalenes (α- and (β-santalene) to α-bergamotene is higher than 2:1.

17. A method for preparing santalol, comprising converting farnesyl diphosphate to santalene in the presence of an isolated or recombinant santalene synthase comprising an amino acid sequence as shown in SEQ ID NO: 3 or a functional homologue thereof, said homologue being a santalene synthase comprising an amino acid sequence which has a sequence identity of at least 95% with SEQ ID NO: 3, further comprising converting the santalene into santalol.

18. The method for preparing santalol, according to claim 17, wherein the santalene is prepared in a host cell, a plant or plant culture, or a mushroom or mushroom culture, expressing said santalene synthase.

19. The method according to claim 17, further comprising isolating the santalol.

20. A transgenic plant or culture comprising transgenic plant cells, said plant or culture comprising the host cell according to claim 6, wherein the host cell is of a transgenic plant selected from tuber forming plants, oil crops, liquid culture plants, tobacco BY2 cells, and trees.

21. The host cell according to claim 6, wherein the host cell is a bacterial cell selected from the group of *Rhodobacter, Paracoccus* and *Escherichia.*

* * * * *

SEQUENCE LISTING

```
<160> NUMBER OF SEQ ID NOS: 33

<210> SEQ ID NO 1
<211> LENGTH: 1662
<212> TYPE: DNA
<213> ORGANISM: Cinnamomum camphora

<400> SEQUENCE: 1

atggactcca tggaggtacg ccgctctgca atctatcact cgaccttttg ggatattgat      60

agcattcgcg ccctgctcgc aagaagagac tgcactgctg cagctgcatt gagtcctgac     120

catcacaaaa gactcaagga aagaattcag cgccggctac aagacatcac acagccacac     180

catctgcttg gattgatcga cgctgtccaa cgcctcggtg tggcctacca gtttgaggaa     240

gaaatcagtg acgcactgca tgggcttcac tcagagaaca cggagcatgc aattaaggac     300

agtctgcacc acacatctct ctattttaga ttgcttaggc aacatgggtg taacctttca     360

tcagacatat tcaacaaatt taagaaggaa ggaggaggtt tcaaggcaag cctatgtgag     420

gatgcaatgg gacttttgag cttgtatgag gctgtacgtc ttagcgtcaa aggtgaagcc     480

atcttggagg aagctcaggt cttctcgatc gcgaatttga agattctgat ggaaagggtg     540

gagaggaagc tggcagatag aatagaacat gccttggaga tccccttgta ttggagggcg     600

ccgagactgg aagctagatg gtacatagat gtatatgaaa aggaagatgg gaggattgat     660

gacttgcttg attttgcaaa gctagatttc aacagggtgc aaatgttgta ccaaaccgaa     720

ctgaaggaat tatcaatgtg gtgggaattg ctggggttac cagcgaagat ggggttcttc     780

cgagacagac tattggagaa ccatctcttt tcaattgcag tggttgtcga gcctcaatac     840
```

```
tcccagtgta gagtagcaat tacaaaagcc atagtcctta tgacagcaat ggatgacttt    900

tatgatgtgc atggtttgcc agatgagcta aaagtcttca cggacaccgt taatcggtgg    960

gatttagagg gaattgatca actaccagag tatatgaagc tgtactactt ggcgttatat   1020

aatacaacca atgagaccgc atacatcatc ctcaaggaga agggattcaa tgctacacat   1080

tatctgaaga aactgtgggc aatgcaaagt aacgcgtact ttcgggaagc tcaatggttc   1140

aacagtggtt acatacctaa atttgatgag tatttagaca atgctttagt ctcagttggg   1200

gcgccctttg tattgggtct ctcataccc atgatacaac aacaaatatc aaaggaggaa    1260

attgatttaa tccccgaaga tctaaatctc ctccgttggg catcgatcat atttcgacta   1320

tatgatgatt tggccacttc aaaggctgag caacaacgtg ggacgtgcc aaaatccatc    1380

caatgttata tgcatgaaac tggtagttcg gaggaagttg cagcaaacca tatcagggac   1440

ctcatcagtg atgcttggaa ggaagtgaat gcagagtgtt tgaaacctac ttctctgtca   1500

aagcattacg tgggagtagc tccaaattcg gctaggtctg gagtgctgat gtaccatcat   1560

gactttgatg gctttgcaag tccccatggc aggactaatg ctcatatcac gtcaatattt   1620

tttgaaccag tgccattgaa ggaatccatc aacttgggat ga                      1662
```

```
<210> SEQ ID NO 2
<211> LENGTH: 1758
<212> TYPE: DNA
<213> ORGANISM: artificial sequence
<220> FEATURE:
<223> OTHER INFORMATION: codon optimized sequence

<400> SEQUENCE: 2

aaatcataaa aaatttattt gctttgtgag cggataacaa ttattagatt caccggcgag     60

ccagcaggaa tttcacttag atgacaggag ggacatatgg acagcatgga agtccggcgg    120

tcggcgatct accacagcac gttctgggac atcgacagca tccgggcgct cctggcgcgg    180

cgggactgca cggcggccgc ggccctctcg cccgaccacc ataagcgcct gaaggagcgc    240

atccagcgcc gcctccagga catcacccag ccccaccatc tgctcggcct catcgacgcc    300

gtgcagcgcc tgggcgtggc ctaccagttc gaggaagaga tctcggacgc gctgcacggc    360

ctccattcgg agaacaccga gcacgccatc aaggactcgc tgcaccatac gtcgctctat    420

ttccgcctgc tccgccagca tggctgcaac ctgtcgtcgg acatcttcaa caagttcaag    480

aaggaaggcg gcggcttcaa ggcctcgctc tgcgaggacg ccatgggcct gctctcgctg    540

tatgaggccg tgcgcctctc ggtgaagggc gaggccatcc tggaggaagc ccaggtgttc    600

tcgatcgcca acctgaagat cctcatggag cgcgtggagc gcaagctcgc cgaccgcatc    660

gagcatgccc tggagatccc gctctattgg cgcgccccgc gtctggaggc ccgctggtac    720

atcgacgtgt atgagaagga agacggccgc atcgacgacc tgctcgactt cgcgaagctg    780

gacttcaacc gcgtgcagat gctctatcag accgagctga aggagctctc gatgtggtgg    840

gagctgctgg gcctgcccgc caagatgggc ttcttccgcg accgcctgct cgagaaccac    900

ctcttctcga tcgccgtggt ggtggagccc cagtactcgc agtgccgcgt ggccatcacc    960

aaggcgatcg tgctgatgac ggcgatggac gacttctatg acgtgcatgg cctgccggac   1020

gagctcaagg tgttcaccga cacggtgaac cgctgggacc tggagggcat cgaccagctc   1080

cccgagtaca tgaagctgta ctatctggcg ctctacaaca ccacgaacga gacggcctat   1140

atcatcctga aggagaaggg cttcaacgcc acgcattacc tgaagaagct ctgggccatg   1200
```

```
cagtcgaacg cgtatttccg cgaggcccag tggttcaact cgggctacat cccgaagttc   1260

gacgagtatc tggacaacgc cctcgtgtcg gtgggcgccc cgttcgtgct gggcctctcg   1320

tatcccatga tccagcagca gatctcgaag gaagagatcg acctgatccc cgaggacctc   1380

aacctgctcc gctgggcctc gatcatcttc cgcctgtacg acgacctggc cacctcgaag   1440

gccgagcagc agcgcggcga cgtgcccaag tcgatccagt gctatatgca tgagacgggc   1500

tcgtcggagg aagtggcggc caaccatatc cgcgacctga tctcggacgc gtggaaggaa   1560

gtgaacgccg agtgcctgaa gccgacctcg ctctcgaagc actacgtggg cgtggccccc   1620

aactcggccc gctcgggcgt gctcatgtat caccatgact tcgacggctt cgcgtcgccc   1680

catggccgca cgaacgccca catcacgagc atcttcttcg agccggtccc cctcaaggag   1740

agcatcaacc tgggctga                                                 1758
```

<210> SEQ ID NO 3
<211> LENGTH: 553
<212> TYPE: PRT
<213> ORGANISM: Cinnamomum camphora

<400> SEQUENCE: 3

```
Met Asp Ser Met Glu Val Arg Arg Ser Ala Ile Tyr His Ser Thr Phe
1               5                   10                  15

Trp Asp Ile Asp Ser Ile Arg Ala Leu Leu Ala Arg Arg Asp Cys Thr
            20                  25                  30

Ala Ala Ala Ala Leu Ser Pro Asp His His Lys Arg Leu Lys Glu Arg
        35                  40                  45

Ile Gln Arg Arg Leu Gln Asp Ile Thr Gln Pro His His Leu Leu Gly
    50                  55                  60

Leu Ile Asp Ala Val Gln Arg Leu Gly Val Ala Tyr Gln Phe Glu Glu
65                  70                  75                  80

Glu Ile Ser Asp Ala Leu His Gly Leu His Ser Glu Asn Thr Glu His
                85                  90                  95

Ala Ile Lys Asp Ser Leu His His Thr Ser Leu Tyr Phe Arg Leu Leu
            100                 105                 110

Arg Gln His Gly Cys Asn Leu Ser Ser Asp Ile Phe Asn Lys Phe Lys
        115                 120                 125

Lys Glu Gly Gly Gly Phe Lys Ala Ser Leu Cys Glu Asp Ala Met Gly
    130                 135                 140

Leu Leu Ser Leu Tyr Glu Ala Val Arg Leu Ser Val Lys Gly Glu Ala
145                 150                 155                 160

Ile Leu Glu Glu Ala Gln Val Phe Ser Ile Ala Asn Leu Lys Ile Leu
                165                 170                 175

Met Glu Arg Val Glu Arg Lys Leu Ala Asp Arg Ile Glu His Ala Leu
            180                 185                 190

Glu Ile Pro Leu Tyr Trp Arg Ala Pro Arg Leu Glu Ala Arg Trp Tyr
        195                 200                 205

Ile Asp Val Tyr Glu Lys Glu Asp Gly Arg Ile Asp Asp Leu Leu Asp
    210                 215                 220

Phe Ala Lys Leu Asp Phe Asn Arg Val Gln Met Leu Tyr Gln Thr Glu
225                 230                 235                 240

Leu Lys Glu Leu Ser Met Trp Trp Glu Leu Leu Gly Leu Pro Ala Lys
                245                 250                 255

Met Gly Phe Phe Arg Asp Arg Leu Leu Glu Asn His Leu Phe Ser Ile
            260                 265                 270
```

```
Ala Val Val Val Glu Pro Gln Tyr Ser Gln Cys Arg Val Ala Ile Thr
        275                 280                 285

Lys Ala Ile Val Leu Met Thr Ala Met Asp Asp Phe Tyr Asp Val His
    290                 295                 300

Gly Leu Pro Asp Glu Leu Lys Val Phe Thr Asp Thr Val Asn Arg Trp
305                 310                 315                 320

Asp Leu Glu Gly Ile Asp Gln Leu Pro Glu Tyr Met Lys Leu Tyr Tyr
                325                 330                 335

Leu Ala Leu Tyr Asn Thr Thr Asn Glu Thr Ala Tyr Ile Ile Leu Lys
            340                 345                 350

Glu Lys Gly Phe Asn Ala Thr His Tyr Leu Lys Lys Leu Trp Ala Met
        355                 360                 365

Gln Ser Asn Ala Tyr Phe Arg Glu Ala Gln Trp Phe Asn Ser Gly Tyr
    370                 375                 380

Ile Pro Lys Phe Asp Glu Tyr Leu Asp Asn Ala Leu Val Ser Val Gly
385                 390                 395                 400

Ala Pro Phe Val Leu Gly Leu Ser Tyr Pro Met Ile Gln Gln Gln Ile
                405                 410                 415

Ser Lys Glu Glu Ile Asp Leu Ile Pro Glu Asp Leu Asn Leu Leu Arg
            420                 425                 430

Trp Ala Ser Ile Ile Phe Arg Leu Tyr Asp Asp Leu Ala Thr Ser Lys
        435                 440                 445

Ala Glu Gln Gln Arg Gly Asp Val Pro Lys Ser Ile Gln Cys Tyr Met
    450                 455                 460

His Glu Thr Gly Ser Ser Glu Glu Val Ala Ala Asn His Ile Arg Asp
465                 470                 475                 480

Leu Ile Ser Asp Ala Trp Lys Glu Val Asn Ala Glu Cys Leu Lys Pro
                485                 490                 495

Thr Ser Leu Ser Lys His Tyr Val Gly Val Ala Pro Asn Ser Ala Arg
            500                 505                 510

Ser Gly Val Leu Met Tyr His His Asp Phe Asp Gly Phe Ala Ser Pro
        515                 520                 525

His Gly Arg Thr Asn Ala His Ile Thr Ser Ile Phe Phe Glu Pro Val
    530                 535                 540

Pro Leu Lys Glu Ser Ile Asn Leu Gly
545                 550
```

<210> SEQ ID NO 4
<211> LENGTH: 2636
<212> TYPE: DNA
<213> ORGANISM: artificial sequence
<220> FEATURE:
<223> OTHER INFORMATION: SPppa-MBP-CiCaSSy

<400> SEQUENCE: 4

```
aaatttattt gctttgtgag cggataacaa ttattagatt caccggcgag ccagcaggaa      60

tttcactcta gatgacagga gggacatcat acgacgacga caagatcttc caggacaagc     120

tctatccctt cacgtgggac gccgtgcgct acaacggcaa gctgatcgcg tatcccatcg     180

cggtggaggc cctgtcgctc atctataaca aggacctgct cccgaacccg cccaagacct     240

gggaggagat ccccgccctc gacaaggagc tgaaggccaa gggcaagtcg gcgctcatgt     300

tcaacctgca ggagccgtac ttcacctggc ccctgatcgc ggccgacggc ggctacgcgt     360

tcaagtatga gaacggcaag tatgacatca aggacgtggg cgtggacaac gcgggcgcca     420

aggccggcct gaccttcctc gtggacctga tcaagaacaa gcacatgaac gccgacacgg     480
```

```
actactcgat cgcggaggcc gcgttcaaca agggcgagac cgccatgacg atcaacggcc    540
cgtgggcgtg gtcgaacatc gacacctcga aggtgaacta tggcgtgacc gtgctcccca    600
cgttcaaggg ccagccctcg aagcccttcg tgggcgtgct gtcggcgggc atcaacgccg    660
cgtcgccgaa caaggagctc gcgaaggagt tcctggagaa ctacctgctc accgacgagg    720
gcctggaggc cgtgaacaag gacaagcccc tgggcgccgt ggccctgaag tcgtatgagg    780
aagagctggt gaaggacccg cgcatcgcgg ccaccatgga gaacgcgcag aagggcgaga    840
tcatgccgaa catcccccag atgtcggcct tctggtatgc ggtgcgcacc gccgtgatca    900
acgcggcctc gggccgccag accgtggacg aggccctcaa ggacgcccag accggcgacg    960
acgacgacaa gatcatggac agcatggaag tccggcggtc ggcgatctac cacagcacgt   1020
tctgggacat cgacagcatc cgggcgctcc tggcgcggcg ggactgcacg gcggccgcgg   1080
ccctctcgcc cgaccaccat aagcgcctga aggagcgcat ccagcgccgc ctccaggaca   1140
tcacccagcc ccaccatctg ctcggcctca tcgacgccgt gcagcgcctg ggcgtggcct   1200
accagttcga ggaagagatc tcggacgcgc tgcacggcct ccattcggag aacaccgagc   1260
acgccatcaa ggactcgctg caccatacgt cgctctattt ccgcctgctc cgccagcatg   1320
gctgcaacct gtcgtcggac atcttcaaca agttcaagaa ggaaggcggc ggcttcaagg   1380
cctcgctctg cgaggacgcc atgggcctgc tctcgctgta tgaggccgtg cgcctctcgg   1440
tgaagggcga ggccatcctg gaggaagccc aggtgttctc gatcgccaac ctgaagatcc   1500
tcatggagcg cgtggagcgc aagctcgccg accgcatcga gcatgccctg gagatcccgc   1560
tctattggcg cgccccgcgt ctggaggccc gctggtacat cgacgtgtat gagaaggaag   1620
acggccgcat cgacgacctg ctcgacttcg cgaagctgga cttcaaccgc gtgcagatgc   1680
tctatcagac cgagctgaag gagctctcga tgtggtggga gctgctgggc ctgcccgcca   1740
agatgggctt cttccgcgac cgcctgctcg agaaccacct cttctcgatc gccgtggtgg   1800
tggagcccca gtactcgcag tgccgcgtgg ccatcaccaa ggcgatcgtg ctgatgacgg   1860
cgatggacga cttctatgac gtgcatggcc tgccggacga gctcaaggtg ttcaccgaca   1920
cggtgaaccg ctgggacctg gagggcatcg accagctccc cgagtacatg aagctgtact   1980
atctggcgct ctacaacacc acgaacgaga cggcctatat catcctgaag gagaagggct   2040
tcaacgccac gcattacctg aagaagctct gggccatgca gtcgaacgcg tatttccgcg   2100
aggcccagtg gttcaactcg ggctacatcc cgaagttcga cgagtatctg gacaacgccc   2160
tcgtgtcggt gggcgccccg ttcgtgctgg gcctctcgta tcccatgatc cagcagcaga   2220
tctcgaagga agagatcgac ctgatccccg aggacctcaa cctgctccgc tgggcctcga   2280
tcatcttccg cctgtacgac gacctggcca cctcgaaggc cgagcagcag cgcggcgacg   2340
tgcccaagtc gatccagtgc tatatgcatg agacgggctc gtcggaggaa gtggcggcca   2400
accatatccg cgacctgatc tcggacgcgt ggaaggaagt gaacgccgag tgcctgaagc   2460
cgacctcgct ctcgaagcac tacgtgggcg tggcccccaa ctcggcccgc tcgggcgtgc   2520
tcatgtatca ccatgacttc gacggcttcg cgtcgcccca tggccgcacg aacgcccaca   2580
tcacgagcat cttcttcgag ccggtccccc tcaaggagag catcaacctg ggctga       2636
```

<210> SEQ ID NO 5
<211> LENGTH: 927
<212> TYPE: PRT
<213> ORGANISM: artificial protein
<220> FEATURE:

```
<223> OTHER INFORMATION: MBP-CiCaSSy

<400> SEQUENCE: 5

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Asp Asp Asp Asp Lys Ile Met Asp Ser Met Glu Val Arg Arg Ser Ala
    370                 375                 380

Ile Tyr His Ser Thr Phe Trp Asp Ile Asp Ser Ile Arg Ala Leu Leu
385                 390                 395                 400
```

```
Ala Arg Arg Asp Cys Thr Ala Ala Ala Ala Leu Ser Pro Asp His His
                405                 410                 415

Lys Arg Leu Lys Glu Arg Ile Gln Arg Arg Leu Gln Asp Ile Thr Gln
            420                 425                 430

Pro His His Leu Leu Gly Leu Ile Asp Ala Val Gln Arg Leu Gly Val
        435                 440                 445

Ala Tyr Gln Phe Glu Glu Glu Ile Ser Asp Ala Leu His Gly Leu His
    450                 455                 460

Ser Glu Asn Thr Glu His Ala Ile Lys Asp Ser Leu His His Thr Ser
465                 470                 475                 480

Leu Tyr Phe Arg Leu Leu Arg Gln His Gly Cys Asn Leu Ser Ser Asp
                485                 490                 495

Ile Phe Asn Lys Phe Lys Lys Glu Gly Gly Gly Phe Lys Ala Ser Leu
            500                 505                 510

Cys Glu Asp Ala Met Gly Leu Leu Ser Leu Tyr Glu Ala Val Arg Leu
        515                 520                 525

Ser Val Lys Gly Glu Ala Ile Leu Glu Glu Ala Gln Val Phe Ser Ile
    530                 535                 540

Ala Asn Leu Lys Ile Leu Met Glu Arg Val Glu Arg Lys Leu Ala Asp
545                 550                 555                 560

Arg Ile Glu His Ala Leu Glu Ile Pro Leu Tyr Trp Arg Ala Pro Arg
                565                 570                 575

Leu Glu Ala Arg Trp Tyr Ile Asp Val Tyr Glu Lys Glu Asp Gly Arg
            580                 585                 590

Ile Asp Asp Leu Leu Asp Phe Ala Lys Leu Asp Phe Asn Arg Val Gln
        595                 600                 605

Met Leu Tyr Gln Thr Glu Leu Lys Glu Leu Ser Met Trp Trp Glu Leu
    610                 615                 620

Leu Gly Leu Pro Ala Lys Met Gly Phe Phe Arg Asp Arg Leu Leu Glu
625                 630                 635                 640

Asn His Leu Phe Ser Ile Ala Val Val Val Glu Pro Gln Tyr Ser Gln
                645                 650                 655

Cys Arg Val Ala Ile Thr Lys Ala Ile Val Leu Met Thr Ala Met Asp
            660                 665                 670

Asp Phe Tyr Asp Val His Gly Leu Pro Asp Glu Leu Lys Val Phe Thr
        675                 680                 685

Asp Thr Val Asn Arg Trp Asp Leu Glu Gly Ile Asp Gln Leu Pro Glu
    690                 695                 700

Tyr Met Lys Leu Tyr Tyr Leu Ala Leu Tyr Asn Thr Thr Asn Glu Thr
705                 710                 715                 720

Ala Tyr Ile Ile Leu Lys Glu Lys Gly Phe Asn Ala Thr His Tyr Leu
                725                 730                 735

Lys Lys Leu Trp Ala Met Gln Ser Asn Ala Tyr Phe Arg Glu Ala Gln
            740                 745                 750

Trp Phe Asn Ser Gly Tyr Ile Pro Lys Phe Asp Glu Tyr Leu Asp Asn
        755                 760                 765

Ala Leu Val Ser Val Gly Ala Pro Phe Val Leu Gly Leu Ser Tyr Pro
    770                 775                 780

Met Ile Gln Gln Gln Ile Ser Lys Glu Glu Ile Asp Leu Ile Pro Glu
785                 790                 795                 800

Asp Leu Asn Leu Leu Arg Trp Ala Ser Ile Ile Phe Arg Leu Tyr Asp
                805                 810                 815
```

```
Asp Leu Ala Thr Ser Lys Ala Glu Gln Gln Arg Gly Asp Val Pro Lys
            820                 825                 830

Ser Ile Gln Cys Tyr Met His Glu Thr Gly Ser Ser Glu Glu Val Ala
        835                 840                 845

Ala Asn His Ile Arg Asp Leu Ile Ser Asp Ala Trp Lys Glu Val Asn
    850                 855                 860

Ala Glu Cys Leu Lys Pro Thr Ser Leu Ser Lys His Tyr Val Gly Val
865                 870                 875                 880

Ala Pro Asn Ser Ala Arg Ser Gly Val Leu Met Tyr His His Asp Phe
                885                 890                 895

Asp Gly Phe Ala Ser Pro His Gly Arg Thr Asn Ala His Ile Thr Ser
            900                 905                 910

Ile Phe Phe Glu Pro Val Pro Leu Lys Glu Ser Ile Asn Leu Gly
        915                 920                 925


<210> SEQ ID NO 6
<211> LENGTH: 2282
<212> TYPE: DNA
<213> ORGANISM: artificial sequence
<220> FEATURE:
<223> OTHER INFORMATION: PcrtE-TRX-CiCaSSy

<400> SEQUENCE: 6

cgctgctgaa cgcgatggcg gcgcggggcg cgacgcgcgg ggccgcatcc gtctgcatcg      60

gcgggggcga ggcgacggcc atcgcgctgg aacggctgag ctaattcatt tgcgcgaatc     120

cgcgtttttc gtgcacgatg gggaaccgg aaacggccac gcctgttgtg gttgcgtcga     180

cctgtcttcg ggccatgccc gtgacgcgat gtggcaggcg catggggcgt tgccgatccg     240

gtcgcatgac tgacgcaacg aaggcacata tgtcggacaa gatcatccac ctgaccgacg     300

acagcttcga caccgacgtg ctgaaggccg acggcgccat cctcgtcgat ttctgggccg     360

aatggtgcgg cccctgcaag atgatcgcgc cgatcctcga cgagatcgcc gacgaatatc     420

agggcaagct gaccgtcgcc aagctgaaca tcgaccagaa cccgggcacg gcgccgaaat     480

acggcatccg cggcatcccg acgctgctgc tcttcaagaa cggcgaggtg gcggccacca     540

aggtcggcgc gctgtcgaag ggccagctga aggagttcct cgatgcgaac ctcgccggtg     600

gtgatgacga cgacaagatt atggacagca tggaagtccg gcggtcggcg atctaccaca     660

gcacgttctg ggacatcgac agcatccggg cgctcctggc gcggcgggac tgcacggcgg     720

ccgcggccct ctcgcccgac caccataagc gcctgaagga gcgcatccag cgccgcctcc     780

aggacatcac ccagccccac catctgctcg gcctcatcga cgccgtgcag cgcctgggcg     840

tggcctacca gttcgaggaa gagatctcgg acgcgctgca cggcctccat tcggagaaca     900

ccgagcacgc catcaaggac tcgctgcacc atacgtcgct ctatttccgc ctgctccgcc     960

agcatggctg caacctgtcg tcggacatct tcaacaagtt caagaaggaa ggcggcggct    1020

tcaaggcctc gctctgcgag gacgccatgg gcctgctctc gctgtatgag gccgtgcgcc    1080

tctcggtgaa gggcgaggcc atcctggagg aagcccaggt gttctcgatc gccaacctga    1140

agatcctcat ggagcgcgtg gagcgcaagc tcgccgaccg catcgagcat gccctggaga    1200

tcccgctcta ttggcgcgcc ccgcgtctgg aggcccgctg gtacatcgac gtgtatgaga    1260

aggaagacgg ccgcatcgac gacctgctcg acttcgcgaa gctggacttc aaccgcgtgc    1320

agatgctcta tcagaccgag ctgaaggagc tctcgatgtg gtgggagctg ctgggcctgc    1380

ccgccaagat gggcttcttc cgcgaccgcc tgctcgagaa ccacctcttc tcgatcgccg    1440
```

```
tggtggtgga gccccagtac tcgcagtgcc gcgtggccat caccaaggcg atcgtgctga   1500

tgacggcgat ggacgacttc tatgacgtgc atggcctgcc ggacgagctc aaggtgttca   1560

ccgacacggt gaaccgctgg gacctggagg gcatcgacca gctccccgag tacatgaagc   1620

tgtactatct ggcgctctac aacaccacga acgagacggc ctatatcatc ctgaaggaga   1680

agggcttcaa cgccacgcat tacctgaaga agctctgggc catgcagtcg aacgcgtatt   1740

tccgcgaggc ccagtggttc aactcgggct acatcccgaa gttcgacgag tatctggaca   1800

acgccctcgt gtcggtgggc gccccgttcg tgctgggcct ctcgtatccc atgatccagc   1860

agcagatctc gaaggaagag atcgacctga tccccgagga cctcaacctg ctccgctggg   1920

cctcgatcat cttccgcctg tacgacgacc tggccacctc gaaggccgag cagcagcgcg   1980

gcgacgtgcc caagtcgatc cagtgctata tgcatgagac gggctcgtcg gaggaagtgg   2040

cggccaacca tatccgcgac ctgatctcgg acgcgtggaa ggaagtgaac gccgagtgcc   2100

tgaagccgac ctcgctctcg aagcactacg tgggcgtggc ccccaactcg gcccgctcgg   2160

gcgtgctcat gtatcaccat gacttcgacg gcttcgcgtc gccccatggc cgcacgaacg   2220

cccacatcac gagcatcttc ttcgagccgg tccccctcaa ggagagcatc aacctgggct   2280

ga                                                                  2282
```

```
<210> SEQ ID NO 7
<211> LENGTH: 670
<212> TYPE: PRT
<213> ORGANISM: artificial sequence
<220> FEATURE:
<223> OTHER INFORMATION: TRX-CiCaSSy

<400> SEQUENCE: 7

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Asp
            100                 105                 110

Asp Asp Asp Lys Ile Met Asp Ser Met Glu Val Arg Arg Ser Ala Ile
        115                 120                 125

Tyr His Ser Thr Phe Trp Asp Ile Asp Ser Ile Arg Ala Leu Leu Ala
    130                 135                 140

Arg Arg Asp Cys Thr Ala Ala Ala Ala Leu Ser Pro Asp His His Lys
145                 150                 155                 160

Arg Leu Lys Glu Arg Ile Gln Arg Arg Leu Gln Asp Ile Thr Gln Pro
                165                 170                 175

His His Leu Leu Gly Leu Ile Asp Ala Val Gln Arg Leu Gly Val Ala
            180                 185                 190

Tyr Gln Phe Glu Glu Glu Ile Ser Asp Ala Leu His Gly Leu His Ser
        195                 200                 205
```

```
Glu Asn Thr Glu His Ala Ile Lys Asp Ser Leu His His Thr Ser Leu
    210                 215                 220

Tyr Phe Arg Leu Leu Arg Gln His Gly Cys Asn Leu Ser Ser Asp Ile
225                 230                 235                 240

Phe Asn Lys Phe Lys Lys Glu Gly Gly Gly Phe Lys Ala Ser Leu Cys
                245                 250                 255

Glu Asp Ala Met Gly Leu Leu Ser Leu Tyr Glu Ala Val Arg Leu Ser
            260                 265                 270

Val Lys Gly Glu Ala Ile Leu Glu Glu Ala Gln Val Phe Ser Ile Ala
        275                 280                 285

Asn Leu Lys Ile Leu Met Glu Arg Val Glu Arg Lys Leu Ala Asp Arg
    290                 295                 300

Ile Glu His Ala Leu Glu Ile Pro Leu Tyr Trp Arg Ala Pro Arg Leu
305                 310                 315                 320

Glu Ala Arg Trp Tyr Ile Asp Val Tyr Glu Lys Glu Asp Gly Arg Ile
                325                 330                 335

Asp Asp Leu Leu Asp Phe Ala Lys Leu Asp Phe Asn Arg Val Gln Met
            340                 345                 350

Leu Tyr Gln Thr Glu Leu Lys Glu Leu Ser Met Trp Trp Glu Leu Leu
        355                 360                 365

Gly Leu Pro Ala Lys Met Gly Phe Phe Arg Asp Arg Leu Leu Glu Asn
    370                 375                 380

His Leu Phe Ser Ile Ala Val Val Val Glu Pro Gln Tyr Ser Gln Cys
385                 390                 395                 400

Arg Val Ala Ile Thr Lys Ala Ile Val Leu Met Thr Ala Met Asp Asp
                405                 410                 415

Phe Tyr Asp Val His Gly Leu Pro Asp Glu Leu Lys Val Phe Thr Asp
            420                 425                 430

Thr Val Asn Arg Trp Asp Leu Glu Gly Ile Asp Gln Leu Pro Glu Tyr
        435                 440                 445

Met Lys Leu Tyr Tyr Leu Ala Leu Tyr Asn Thr Thr Asn Glu Thr Ala
    450                 455                 460

Tyr Ile Ile Leu Lys Glu Lys Gly Phe Asn Ala Thr His Tyr Leu Lys
465                 470                 475                 480

Lys Leu Trp Ala Met Gln Ser Asn Ala Tyr Phe Arg Glu Ala Gln Trp
                485                 490                 495

Phe Asn Ser Gly Tyr Ile Pro Lys Phe Asp Glu Tyr Leu Asp Asn Ala
            500                 505                 510

Leu Val Ser Val Gly Ala Pro Phe Val Leu Gly Leu Ser Tyr Pro Met
        515                 520                 525

Ile Gln Gln Gln Ile Ser Lys Glu Glu Ile Asp Leu Ile Pro Glu Asp
    530                 535                 540

Leu Asn Leu Leu Arg Trp Ala Ser Ile Ile Phe Arg Leu Tyr Asp Asp
545                 550                 555                 560

Leu Ala Thr Ser Lys Ala Glu Gln Gln Arg Gly Asp Val Pro Lys Ser
                565                 570                 575

Ile Gln Cys Tyr Met His Glu Thr Gly Ser Ser Glu Glu Val Ala Ala
            580                 585                 590

Asn His Ile Arg Asp Leu Ile Ser Asp Ala Trp Lys Glu Val Asn Ala
        595                 600                 605

Glu Cys Leu Lys Pro Thr Ser Leu Ser Lys His Tyr Val Gly Val Ala
    610                 615                 620
```

```
Pro Asn Ser Ala Arg Ser Gly Val Leu Met Tyr His His Asp Phe Asp
625                 630                 635                 640

Gly Phe Ala Ser Pro His Gly Arg Thr Asn Ala His Ile Thr Ser Ile
                645                 650                 655

Phe Phe Glu Pro Val Pro Leu Lys Glu Ser Ile Asn Leu Gly
            660                 665                 670


<210> SEQ ID NO 8
<211> LENGTH: 39
<212> TYPE: DNA
<213> ORGANISM: artificial sequence
<220> FEATURE:
<223> OTHER INFORMATION: primer

<400> SEQUENCE: 8

atatggatcc tatggactcc atggaggtac gccgctctg                             39


<210> SEQ ID NO 9
<211> LENGTH: 47
<212> TYPE: DNA
<213> ORGANISM: artificial sequence
<220> FEATURE:
<223> OTHER INFORMATION: TS23 RE

<400> SEQUENCE: 9

atatgcggcc gctcatccca agttgatgga ttccttcaat ggcactg                    47


<210> SEQ ID NO 10
<211> LENGTH: 553
<212> TYPE: PRT
<213> ORGANISM: artificial sequence
<220> FEATURE:
<223> OTHER INFORMATION: TS23-1

<400> SEQUENCE: 10

Met Asp Ser Met Glu Val Arg Arg Ser Ala Asn Tyr His Ser Thr Phe
1               5                   10                  15

Trp Asp Ile Asp Ser Ile Arg Ala Leu Leu Ala Arg Arg Asp Cys Thr
            20                  25                  30

Val Ala Ala Ala Leu Ser His Asp His His Lys Arg Leu Lys Glu Arg
        35                  40                  45

Ile Gln Arg Arg Leu Gln Asp Ile Thr Gln Pro His His Leu Leu Gly
    50                  55                  60

Leu Ile Asp Ala Val Gln Arg Leu Gly Val Ala Tyr Gln Phe Glu Glu
65                  70                  75                  80

Glu Ile Ser Asp Ala Leu His Gly Leu His Ser Glu Asn Thr Glu His
                85                  90                  95

Ala Ile Lys Asp Ser Leu His His Thr Ser Leu Tyr Phe Arg Leu Leu
            100                 105                 110

Arg Gln His Gly Cys Asn Leu Ser Ser Asp Ile Phe Asn Lys Phe Lys
        115                 120                 125

Lys Glu Gly Gly Gly Phe Lys Ala Ser Leu Cys Glu Asp Ala Met Gly
    130                 135                 140

Leu Leu Ser Leu Tyr Glu Ala Ala His Leu Gly Val Lys Ser Glu Ala
145                 150                 155                 160

Ile Leu Glu Glu Ala Gln Val Phe Ser Thr Ser Asn Leu Lys Ile Leu
                165                 170                 175

Met Glu Arg Val Glu Arg Lys Leu Ala Asp Arg Ile Asp His Ala Leu
            180                 185                 190
```

```
Glu Ile Pro Leu Tyr Trp Arg Ala Pro Arg Val Glu Ala Arg Trp Tyr
        195                 200                 205

Ile Asp Val Tyr Glu Lys Glu Asp Gly Arg Ile Asp Asp Leu Leu Asp
    210                 215                 220

Phe Ala Lys Leu Asp Phe Asn Arg Val Gln Met Leu Tyr Gln Thr Glu
225                 230                 235                 240

Leu Lys Glu Leu Ser Met Trp Trp Glu Leu Leu Gly Leu Pro Glu Lys
                245                 250                 255

Met Gly Phe Phe Arg Asp Arg Leu Leu Glu Ser His Leu Phe Ser Ile
            260                 265                 270

Gly Val Val Val Glu Pro Gln Tyr Ser Gln Cys Arg Val Ala Ile Thr
        275                 280                 285

Lys Ala Leu Val Leu Phe Thr Ala Met Asp Asp Phe Tyr Asp Val His
    290                 295                 300

Gly Leu Pro Glu Glu Leu Lys Val Phe Thr Asp Thr Val Asn Arg Trp
305                 310                 315                 320

Asp Leu Glu Gly Ile Asp Gln Leu Pro Glu Tyr Met Lys Leu Tyr Tyr
                325                 330                 335

Leu Ala Leu Tyr Asn Thr Thr Asn Glu Thr Ala Tyr Ile Ile Leu Lys
            340                 345                 350

Glu Lys Gly Phe Asn Ala Thr His Tyr Leu Lys Lys Leu Trp Ala Met
        355                 360                 365

Gln Ser Asn Ser Tyr Phe Arg Glu Ala Gln Trp Phe Asn Ser Gly Tyr
    370                 375                 380

Ile Pro Lys Phe Asp Glu Tyr Leu Asp Asn Ala Leu Val Ser Val Gly
385                 390                 395                 400

Val Pro Leu Leu Leu Gly Leu Ser Tyr Pro Met Ile Gln Gln His Ile
                405                 410                 415

Ser Lys Ala Glu Ile Asp Leu Ile Pro Glu Asp Leu Asn Leu Leu Arg
            420                 425                 430

Trp Ala Ser Ile Ile Phe Arg Leu Tyr Asn Asp Leu Ala Thr Ser Lys
        435                 440                 445

Ala Glu Gln Gln Arg Gly Asp Val Pro Lys Ser Ile Gln Cys Tyr Met
    450                 455                 460

His Glu Thr Gly Ser Ser Glu Glu Val Ala Ala Asn His Ile Arg Asp
465                 470                 475                 480

Leu Ile Ser Asp Ala Trp Lys Glu Leu Asn Ala Glu Cys Leu Lys Pro
                485                 490                 495

Thr Ser Leu Ser Lys His Tyr Val Gly Val Ala Pro Asn Ser Ala Arg
            500                 505                 510

Ser Gly Val Leu Met Tyr His His Asp Phe Asp Gly Phe Ala Ser Pro
        515                 520                 525

His Ser Arg Thr Asn Ala His Ile Thr Ser Ile Phe Phe Glu Pro Val
    530                 535                 540

Pro Leu Lys Glu Ser Ile Asn Leu Gly
545                 550
```

<210> SEQ ID NO 11
<211> LENGTH: 553
<212> TYPE: PRT
<213> ORGANISM: artificial sequence
<220> FEATURE:
<223> OTHER INFORMATION: TS23-2

<400> SEQUENCE: 11

```
Met Asp Ser Met Glu Val Arg Arg Ser Ala Asn Tyr His Ser Thr Phe
1               5                   10                  15

Trp Asp Ile Asp Ser Ile Arg Ala Leu Leu Ala Arg Arg Asp Cys Thr
            20                  25                  30

Val Ala Ala Ala Leu Ser His Asp His His Lys Arg Leu Lys Glu Arg
        35                  40                  45

Ile Gln Arg Arg Leu Gln Asp Ile Thr Gln Pro His His Leu Leu Gly
    50                  55                  60

Leu Ile Asp Ala Val Gln Arg Leu Gly Val Ala Tyr Gln Phe Glu Glu
65                  70                  75                  80

Glu Ile Ser Asp Ala Leu His Gly Leu His Ser Glu Asn Thr Glu His
                85                  90                  95

Ala Val Lys Asp Ser Leu His His Thr Ser Leu Tyr Phe Arg Leu Leu
            100                 105                 110

Arg Gln His Gly Cys Asn Leu Ser Thr Asp Ile Phe Asn Lys Phe Lys
        115                 120                 125

Lys Glu Gly Gly Gly Phe Lys Ala Ser Leu Cys Glu Asp Ala Met Gly
    130                 135                 140

Leu Leu Ser Leu Tyr Glu Ala Ala His Leu Gly Val Lys Ser Glu Ala
145                 150                 155                 160

Ile Leu Glu Glu Ala Gln Val Phe Ser Thr Ser Asn Leu Lys Ile Leu
                165                 170                 175

Met Glu Arg Val Glu Arg Lys Leu Ala Asp Arg Ile Asp His Ala Leu
            180                 185                 190

Glu Ile Pro Leu Tyr Trp Arg Ala Pro Arg Val Glu Ala Arg Trp Tyr
        195                 200                 205

Ile Asp Val Tyr Glu Lys Glu Asp Gly Arg Ile Asp Asp Leu Leu Asp
    210                 215                 220

Phe Ala Lys Leu Asp Phe Asn Arg Val Gln Met Leu Tyr Gln Thr Glu
225                 230                 235                 240

Leu Lys Glu Leu Ser Met Trp Trp Glu Leu Leu Gly Leu Pro Glu Lys
                245                 250                 255

Met Gly Phe Phe Arg Asp Arg Leu Leu Glu Ser His Leu Phe Ser Ile
            260                 265                 270

Gly Val Val Val Glu Pro Gln Tyr Ser Gln Cys Arg Val Ala Ile Thr
        275                 280                 285

Lys Ala Leu Val Leu Phe Thr Ala Met Asp Asp Phe Tyr Asp Val His
    290                 295                 300

Gly Leu Pro Glu Glu Leu Lys Val Phe Thr Asp Thr Val Asn Arg Trp
305                 310                 315                 320

Asp Leu Glu Gly Ile Asp Gln Leu Pro Glu Tyr Met Lys Leu Tyr Tyr
                325                 330                 335

Leu Ala Leu Tyr Asn Thr Thr Asn Glu Thr Ala Tyr Ile Ile Leu Lys
            340                 345                 350

Glu Lys Gly Phe Asn Ala Thr His Tyr Leu Lys Lys Leu Trp Ala Met
        355                 360                 365

Gln Ser Asn Ser Tyr Phe Arg Glu Ala Gln Trp Phe Asn Ser Gly Tyr
    370                 375                 380

Ile Pro Lys Phe Asp Glu Tyr Leu Asp Asn Ala Leu Val Ser Val Gly
385                 390                 395                 400
```

-continued

```
Val Pro Leu Leu Leu Gly Leu Ser Tyr Pro Met Ile Gln Gln His Ile
                405                 410                 415

Ser Lys Ala Glu Ile Asp Leu Ile Pro Glu Asp Leu Asn Leu Leu Arg
            420                 425                 430

Trp Ala Ser Ile Ile Phe Arg Leu Tyr Asn Asp Leu Ala Thr Ser Lys
        435                 440                 445

Ala Glu Gln Gln Arg Gly Asp Val Pro Lys Ser Ile Gln Cys Tyr Met
    450                 455                 460

His Glu Thr Gly Ser Ser Glu Glu Val Ala Ala Asn His Ile Arg Asp
465                 470                 475                 480

Leu Ile Ser Asp Ala Trp Lys Glu Val Asn Ala Glu Cys Leu Lys Pro
                485                 490                 495

Thr Ser Leu Ser Lys His Tyr Val Gly Val Ala Pro Asn Ser Ala Arg
            500                 505                 510

Ser Gly Val Leu Met Tyr His His Asp Phe Asp Gly Phe Ala Ser Pro
        515                 520                 525

His Ser Arg Thr Asn Ala His Ile Thr Ser Ile Phe Phe Glu Pro Val
    530                 535                 540

Pro Leu Lys Glu Ser Ile Asn Leu Gly
545                 550


<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12

gctgttagcg ggcccattaa g                                                21


<210> SEQ ID NO 13
<211> LENGTH: 40
<212> TYPE: DNA
<213> ORGANISM: artificial sequence
<220> FEATURE:
<223> OTHER INFORMATION: primer

<400> SEQUENCE: 13

gatattctca ttttagccat tttagcttcc ttagctcctg                            40


<210> SEQ ID NO 14
<211> LENGTH: 40
<212> TYPE: DNA
<213> ORGANISM: artificial sequence
<220> FEATURE:
<223> OTHER INFORMATION: primer

<400> SEQUENCE: 14

caggagctaa ggaagctaaa atggctaaaa tgagaatatc                            40


<210> SEQ ID NO 15
<211> LENGTH: 39
<212> TYPE: DNA
<213> ORGANISM: artificial sequence
<220> FEATURE:
<223> OTHER INFORMATION: primer

<400> SEQUENCE: 15

ccaagcgagc tcgatatcaa actaaaacaa ttcatccag                             39
```

<210> SEQ ID NO 16
<211> LENGTH: 23
<212> TYPE: DNA
<213> ORGANISM: artificial sequence
<220> FEATURE:
<223> OTHER INFORMATION: primer

<400> SEQUENCE: 16
ctgtccatga tcttgtcgtc gtc 23

<210> SEQ ID NO 17
<211> LENGTH: 44
<212> TYPE: DNA
<213> ORGANISM: artificial sequence
<220> FEATURE:
<223> OTHER INFORMATION: primer

<400> SEQUENCE: 17
actggcctca gaattcaaat ttatttgctt tgtgagcgga taac 44

<210> SEQ ID NO 18
<211> LENGTH: 25
<212> TYPE: DNA
<213> ORGANISM: artificial sequence
<220> FEATURE:
<223> OTHER INFORMATION: primer

<400> SEQUENCE: 18
caagatcatg gacagcatgg aagtc 25

<210> SEQ ID NO 19
<211> LENGTH: 28
<212> TYPE: DNA
<213> ORGANISM: artificial sequence
<220> FEATURE:
<223> OTHER INFORMATION: primer

<400> SEQUENCE: 19
tttatgattt ggatcctcag cccaggtt 28

<210> SEQ ID NO 20
<211> LENGTH: 25
<212> TYPE: DNA
<213> ORGANISM: artificial sequence
<220> FEATURE:
<223> OTHER INFORMATION: primer

<400> SEQUENCE: 20
ctgtccataa tcttgtcgtc gtcat 25

<210> SEQ ID NO 21
<211> LENGTH: 28
<212> TYPE: DNA
<213> ORGANISM: artificial sequence
<220> FEATURE:
<223> OTHER INFORMATION: primer

<400> SEQUENCE: 21
actggcctca gaattccgct gctgaacg 28

<210> SEQ ID NO 22
<211> LENGTH: 26
<212> TYPE: DNA
<213> ORGANISM: artificial
<220> FEATURE:
<223> OTHER INFORMATION: primer

<400> SEQUENCE: 22
caagattatg gacagcatgg aagtcc 26

<210> SEQ ID NO 23
<211> LENGTH: 28
<212> TYPE: DNA
<213> ORGANISM: artificial
<220> FEATURE:
<223> OTHER INFORMATION: primer

<400> SEQUENCE: 23
tttatgattt ggatcctcag cccaggtt 28

<210> SEQ ID NO 24
<211> LENGTH: 2330
<212> TYPE: DNA
<213> ORGANISM: artificial
<220> FEATURE:
<223> OTHER INFORMATION: PcrtE-TRX-SaSSy

<400> SEQUENCE: 24
cgctgctgaa cgcgatggcg gcgcggggcg cgacgcgcgg ggccgcatcc gtctgcatcg 60
gcgggggcga ggcgacggcc atcgcgctgg aacggctgag ctaattcatt tgcgcgaatc 120
cgcgtttttc gtgcacgatg ggggaaccgg aaacggccac gcctgttgtg gttgcgtcga 180
cctgtcttcg ggccatgccc gtgacgcgat gtggcaggcg catggggcgt tgccgatccg 240
gtcgcatgac tgacgcaacg aaggcacata tgtcggacaa gatcatccac ctgaccgacg 300
acagcttcga caccgacgtg ctgaaggccg acggcgccat cctcgtcgat ttctgggccg 360
aatggtgcgg cccctgcaag atgatcgcgc cgatcctcga cgagatcgcc gacgaatatc 420
agggcaagct gaccgtcgcc aagctgaaca tcgaccagaa cccgggcacg gcgccgaaat 480
acggcatccg cggcatcccg acgctgctgc tcttcaagaa cggcgaggtg gcggccacca 540
aggtcggcgc gctgtcgaag ggccagctga aggagttcct cgatgcgaac ctcgccggtg 600
gtgatgacga cgacaagatt atggacagca gcaccgcgac cgccatgacc gccccccttca 660 tcgaccccac cgaccacgtg aacctcaaga ccgacaccga cgccagcgag aaccgtcgca 720
tgggcaacta caagccgtcg atctggaact atgacttcct gcagagcctc gccacccacc 780
ataacatcgt ggaggagcgc cacctcaagc tggcggagaa gctgaagggc caggtcaagt 840
tcatgttcgg cgcccctatg gagcccctcg cgaagctcga gctggtcgac gtggtccagc 900
ggctcggcct gaaccacctg ttcgagaccg agatcaagga agccctcttc tcgatctaca 960
aggacggcag caacgggtgg tggttcggcc acctgcatgc gacgtcgctc cgcttccggc 1020
tgctccgcca gtgcggcctg ttcatccccc aggacgtgtt caagaccttc cagaacaaga 1080
cgggcgagtt cgacatgaag ctctgcgaca acgtcaaggg cctgctctcg ctgtacgagg 1140
ccagctatct cggctggaag ggcgagaaca tcctggacga ggccaaggcg ttcaccacga 1200
agtgcctcaa gtcggcctgg gagaacatca gcgagaagtg gctggcgaag cgcgtgaagc 1260
acgccctcgc gctgccgctc cattggcgcg tcccccggat cgaggcgcgg tggttcatcg 1320
aggcctatga gcaggaagcc aacatgaacc cgaccctgct caagctggcc aagctcgact 1380
tcaacatggt gcagtcgatc caccagaagg agatcggcga gctggcgcgg tggtgggtca 1440
ccacgggcct ggacaagctc gccttcgcgc ggaacaacct gctccagtcg tacatgtgga 1500
gctgcgccat cgcgtcggac cccaagttca agctggcccg cgagaccatc gtggagatcg 1560

```
gctcggtcct cacggtggtc gacgacggct acgacgtgta tggcagcatc gacgagctgg   1620

acctctatac ctcgagcgtg gagcggtggt cgtgcgtcga gatcgacaag ctcccgaaca   1680

ccctgaagct catcttcatg tcgatgttca acaagacgaa cgaggtcggc ctccgcgtcc   1740

agcatgagcg gggctacaac tcgatcccca cgttcatcaa ggcctgggtg gagcagtgca   1800

agtcgtatca gaaggaagcc cgctggttcc acggtggcca taccccgccc ctggaggagt   1860

actcgctgaa cggcctcgtg agcatcggct tcccgctgct cctgatcacg ggctatgtgg   1920

ccatcgcgga gaacgaggcc gcgctggaca aggtccaccc gctccccgac ctgctgcatt   1980

actcgagcct cctgtcgcgc ctgatcaacg acatcggcac cagccccgac gagatggcgc   2040

ggggcgacaa cctcaagtcg atccactgct atatgaacga gacgggcgcc agcgaggaag   2100

tggcgcgcga gcatatcaag ggcgtcatcg aggagaactg gaagatcctg aaccagtgct   2160

gcttcgacca gtcgcagttc caggagccgt tcatcacctt caacctcaac tcggtgcgcg   2220

gcagccactt cttctacgag ttcggcgacg gcttcggcgt cacggactcg tggacgaagg   2280

tggacatgaa gagcgtgctg atcgacccca tccccctggg cgaggagtga              2330
```

```
<210> SEQ ID NO 25
<211> LENGTH: 686
<212> TYPE: PRT
<213> ORGANISM: artificial
<220> FEATURE:
<223> OTHER INFORMATION: TRX-SaSSy

<400> SEQUENCE: 25

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Asp
            100                 105                 110

Asp Asp Asp Lys Ile Met Asp Ser Ser Thr Ala Thr Ala Met Thr Ala
        115                 120                 125

Pro Phe Ile Asp Pro Thr Asp His Val Asn Leu Lys Thr Asp Thr Asp
    130                 135                 140

Ala Ser Glu Asn Arg Arg Met Gly Asn Tyr Lys Pro Ser Ile Trp Asn
145                 150                 155                 160

Tyr Asp Phe Leu Gln Ser Leu Ala Thr His His Asn Ile Val Glu Glu
                165                 170                 175

Arg His Leu Lys Leu Ala Glu Lys Leu Lys Gly Gln Val Lys Phe Met
            180                 185                 190

Phe Gly Ala Pro Met Glu Pro Leu Ala Lys Leu Glu Leu Val Asp Val
        195                 200                 205

Val Gln Arg Leu Gly Leu Asn His Leu Phe Glu Thr Glu Ile Lys Glu
    210                 215                 220
```

```
Ala Leu Phe Ser Ile Tyr Lys Asp Gly Ser Asn Gly Trp Trp Phe Gly
225                 230                 235                 240

His Leu His Ala Thr Ser Leu Arg Phe Arg Leu Leu Arg Gln Cys Gly
                245                 250                 255

Leu Phe Ile Pro Gln Asp Val Phe Lys Thr Phe Gln Asn Lys Thr Gly
            260                 265                 270

Glu Phe Asp Met Lys Leu Cys Asp Asn Val Lys Gly Leu Leu Ser Leu
        275                 280                 285

Tyr Glu Ala Ser Tyr Leu Gly Trp Lys Gly Glu Asn Ile Leu Asp Glu
    290                 295                 300

Ala Lys Ala Phe Thr Thr Lys Cys Leu Lys Ser Ala Trp Glu Asn Ile
305                 310                 315                 320

Ser Glu Lys Trp Leu Ala Lys Arg Val Lys His Ala Leu Ala Leu Pro
                325                 330                 335

Leu His Trp Arg Val Pro Arg Ile Glu Ala Arg Trp Phe Ile Glu Ala
            340                 345                 350

Tyr Glu Gln Glu Ala Asn Met Asn Pro Thr Leu Leu Lys Leu Ala Lys
        355                 360                 365

Leu Asp Phe Asn Met Val Gln Ser Ile His Gln Lys Glu Ile Gly Glu
    370                 375                 380

Leu Ala Arg Trp Trp Val Thr Thr Gly Leu Asp Lys Leu Ala Phe Ala
385                 390                 395                 400

Arg Asn Asn Leu Leu Gln Ser Tyr Met Trp Ser Cys Ala Ile Ala Ser
                405                 410                 415

Asp Pro Lys Phe Lys Leu Ala Arg Glu Thr Ile Val Glu Ile Gly Ser
            420                 425                 430

Val Leu Thr Val Val Asp Asp Gly Tyr Asp Val Tyr Gly Ser Ile Asp
        435                 440                 445

Glu Leu Asp Leu Tyr Thr Ser Ser Val Glu Arg Trp Ser Cys Val Glu
    450                 455                 460

Ile Asp Lys Leu Pro Asn Thr Leu Lys Leu Ile Phe Met Ser Met Phe
465                 470                 475                 480

Asn Lys Thr Asn Glu Val Gly Leu Arg Val Gln His Glu Arg Gly Tyr
                485                 490                 495

Asn Ser Ile Pro Thr Phe Ile Lys Ala Trp Val Glu Gln Cys Lys Ser
            500                 505                 510

Tyr Gln Lys Glu Ala Arg Trp Phe His Gly Gly His Thr Pro Pro Leu
        515                 520                 525

Glu Glu Tyr Ser Leu Asn Gly Leu Val Ser Ile Gly Phe Pro Leu Leu
    530                 535                 540

Leu Ile Thr Gly Tyr Val Ala Ile Ala Glu Asn Glu Ala Ala Leu Asp
545                 550                 555                 560

Lys Val His Pro Leu Pro Asp Leu Leu His Tyr Ser Ser Leu Leu Ser
                565                 570                 575

Arg Leu Ile Asn Asp Ile Gly Thr Ser Pro Asp Glu Met Ala Arg Gly
            580                 585                 590

Asp Asn Leu Lys Ser Ile His Cys Tyr Met Asn Glu Thr Gly Ala Ser
        595                 600                 605

Glu Glu Val Ala Arg Glu His Ile Lys Gly Val Ile Glu Glu Asn Trp
    610                 615                 620

Lys Ile Leu Asn Gln Cys Cys Phe Asp Gln Ser Gln Phe Gln Glu Pro
625                 630                 635                 640
```

```
Phe Ile Thr Phe Asn Leu Asn Ser Val Arg Gly Ser His Phe Phe Tyr
                645                 650                 655

Glu Phe Gly Asp Gly Phe Gly Val Thr Asp Ser Trp Thr Lys Val Asp
            660                 665                 670

Met Lys Ser Val Leu Ile Asp Pro Ile Pro Leu Gly Glu Glu
        675                 680                 685


<210> SEQ ID NO 26
<211> LENGTH: 495
<212> TYPE: PRT
<213> ORGANISM: artificial
<220> FEATURE:
<223> OTHER INFORMATION: NusA

<400> SEQUENCE: 26

Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320
```

```
Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala
                485                 490                 495


<210> SEQ ID NO 27
<211> LENGTH: 117
<212> TYPE: PRT
<213> ORGANISM: artificial
<220> FEATURE:
<223> OTHER INFORMATION: TRX

<400> SEQUENCE: 27

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Gly Asp
            100                 105                 110

Asp Asp Asp Lys Ile
        115


<210> SEQ ID NO 28
<211> LENGTH: 374
<212> TYPE: PRT
<213> ORGANISM: artificial
<220> FEATURE:
<223> OTHER INFORMATION: MBP

<400> SEQUENCE: 28

Met Lys Ile Glu Glu Gly Lys Leu Val Ile Trp Ile Asn Gly Asp Lys
1               5                   10                  15
```

```
Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
        355                 360                 365

Asp Asp Asp Asp Lys Ile
    370
```

<210> SEQ ID NO 29
<211> LENGTH: 40
<212> TYPE: PRT
<213> ORGANISM: artificial
<220> FEATURE:
<223> OTHER INFORMATION: SET

<400> SEQUENCE: 29

```
Glu Glu Ala Ser Val Thr Ser Thr Glu Glu Thr Leu Thr Pro Ala Gln
1               5                   10                  15

Glu Ala Ala Arg Thr Arg Ala Ala Asn Lys Ala Arg Lys Glu Ala Glu
            20                  25                  30

Leu Ala Ala Ala Thr Ala Glu Gln
        35                  40
```

<210> SEQ ID NO 30
<211> LENGTH: 3147
<212> TYPE: DNA
<213> ORGANISM: artificial
<220> FEATURE:
<223> OTHER INFORMATION: NusA-CiCaSSy

<400> SEQUENCE: 30

```
atgaacaagg agatcctcgc ggtggtggag gcggtgtcga acgagaaggc gctgccccgc     60

gagaagatct tcgaggccct ggagtcggcc ctggccaccg cgaccaagaa gaagtacgag    120

caggagatcg acgtgcgcgt gcagatcgac cgcaagtcgg gcgacttcga cacgttccgc    180

cgctggctcg tggtggacga ggtgacccag cccacgaagg agatcaccct ggaggcggcc    240

cgctatgagg acgagtcgct gaacctcggc gactatgtgg aggaccagat cgagtcggtg    300

accttcgacc gcatcaccac gcagacggcg aagcaggtga tcgtgcagaa ggtgcgcgag    360

gccgagcgcg ccatggtggt ggaccagttc cgcgagcacg agggcgagat catcaccggc    420

gtggtgaaga aggtgaaccg cgacaacatc tcgctggacc tgggcaacaa cgcggaggcc    480

gtgatcctgc gcgaggacat gctcccgcgc gagaacttcc gcccgggcga ccgcgtgcgc    540

ggcgtgctct attcggtgcg ccccgaggcc cgtggcgccc agctgttcgt gacccgctcg    600

aagccggaga tgctgatcga gctcttccgc atcgaggtgc ccgagatcgg cgaggaagtg    660

atcgagatca aggcggccgc ccgcgacccg ggctcgcgcg cgaagatcgc cgtgaagacc    720

aacgacaagc gcatcgaccc cgtgggcgcc tgcgtgggca tgcgtggcgc ccgcgtgcag    780

gccgtgtcga ccgagctcgg cggcgagcgc atcgacatcg tgctgtggga cgacaacccg    840

gcgcagttcg tgatcaacgc catggccccg gcggacgtgg cctcgatcgt ggtggacgag    900

gacaagcata ccatggacat cgccgtggag gcgggcaacc tggcccaggc catcggccgc    960

aacggccaga acgtgcgcct ggcctcgcag ctctcgggct gggagctgaa cgtgatgacg   1020

gtggacgacc tgcaggccaa gcatcaggcc gaggcccatg ccgccatcga caccttcacg   1080

aagtacctcg acatcgacga ggacttcgcg accgtgctcg tggaggaagg cttctcgacg   1140

ctggaggagc tcgcctatgt gccgatgaag gagctgctcg agatcgaggg cctggacgag   1200

ccgacggtgg aggcgctccg cgagcgcgcc aagaacgccc tggccaccat cgcccaggcc   1260

caggaagagt cgctgggcga caacaagccg gccgacgacc tgctcaacct ggagggcgtg   1320

gaccgcgacc tggccttcaa gctcgccgcc cgcggcgtgt gcacgctcga ggacctggcc   1380

gagcagggca tcgacgacct ggccgacatc gagggcctca ccgacgagaa ggccggcgcc   1440

ctgatcatgg ccgcccgcaa catctgctgg ttcggcgacg aggcgatgga cagcatggaa   1500

gtccggcggt cggcgatcta ccacagcacg ttctgggaca tcgacagcat ccgggcgctc   1560

ctggcgcggc gggactgcac ggcggccgcg gccctctcgc ccgaccacca taagcgcctg   1620

aaggagcgca tccagcgccg cctccaggac atcacccagc cccaccatct gctcggcctc   1680

atcgacgccg tgcagcgcct gggcgtggcc taccagttcg aggaagagat ctcggacgcg   1740
```

```
ctgcacggcc tccattcgga gaacaccgag cacgccatca aggactcgct gcaccatacg   1800
tcgctctatt tccgcctgct ccgccagcat ggctgcaacc tgtcgtcgga catcttcaac   1860
aagttcaaga aggaaggcgg cggcttcaag gcctcgctct gcgaggacgc catgggcctg   1920
ctctcgctgt atgaggccgt gcgcctctcg gtgaagggcg aggccatcct ggaggaagcc   1980
caggtgttct cgatcgccaa cctgaagatc ctcatggagc gcgtggagcg caagctcgcc   2040
gaccgcatcg agcatgccct ggagatcccg ctctattggc gcgccccgcg tctggaggcc   2100
cgctggtaca tcgacgtgta tgagaaggaa gacggccgca tcgacgacct gctcgacttc   2160
gcgaagctgg acttcaaccg cgtgcagatg ctctatcaga ccgagctgaa ggagctctcg   2220
atgtggtggg agctgctggg cctgcccgcc aagatgggct tcttccgcga ccgcctgctc   2280
gagaaccacc tcttctcgat cgccgtggtg gtggagcccc agtactcgca gtgccgcgtg   2340
gccatcacca aggcgatcgt gctgatgacg gcgatggacg acttctatga cgtgcatggc   2400
ctgccggacg agctcaaggt gttcaccgac acggtgaacc gctgggacct ggagggcatc   2460
gaccagctcc ccgagtacat gaagctgtac tatctggcgc tctacaacac cacgaacgag   2520
acggcctata tcatcctgaa ggagaagggc ttcaacgcca cgcattacct gaagaagctc   2580
tgggccatgc agtcgaacgc gtatttccgc gaggcccagt ggttcaactc gggctacatc   2640
ccgaagttcg acgagtatct ggacaacgcc ctcgtgtcgg tgggcgcccc gttcgtgctg   2700
ggcctctcgt atcccatgat ccagcagcag atctcgaagg aagagatcga cctgatcccc   2760
gaggacctca acctgctccg ctgggcctcg atcatcttcc gcctgtacga cgacctggcc   2820
acctcgaagg ccgagcagca gcgcggcgac gtgcccaagt cgatccagtg ctatatgcat   2880
gagacgggct cgtcggagga agtggcggcc aaccatatcc gcgacctgat ctcggacgcg   2940
tggaaggaag tgaacgccga gtgcctgaag ccgacctcgc tctcgaagca ctacgtgggc   3000
gtggccccca actcggcccg ctcgggcgtg ctcatgtatc accatgactt cgacggcttc   3060
gcgtcgcccc atggccgcac gaacgcccac atcacgagca tcttcttcga gccggtcccc   3120
ctcaaggaga gcatcaacct gggctga                                      3147
```

<210> SEQ ID NO 31
<211> LENGTH: 1791
<212> TYPE: DNA
<213> ORGANISM: artificial
<220> FEATURE:
<223> OTHER INFORMATION: SET-CiCaSSy

<400> SEQUENCE: 31

```
atggaggagg ccagcgtgac cagcaccgag gagaccctga ccccggccca ggaggccgcc     60
cgcacccgcg ccgccaacaa ggcccgcaag gaggccgagc tggccgccgc caccgccgag    120
caggccgcca tggacagcat ggaagtccgg cggtcggcga tctaccacag cacgttctgg    180
gacatcgaca gcatccgggc gctcctggcg cggcgggact gcacggcggc cgcggccctc    240
tcgcccgacc accataagcg cctgaaggag cgcatccagc gccgcctcca ggacatcacc    300
cagccccacc atctgctcgg cctcatcgac gccgtgcagc gcctgggcgt ggcctaccag    360
ttcgaggaag agatctcgga cgcgctgcac ggcctccatt cggagaacac cgagcacgcc    420
atcaaggact cgctgcacca tacgtcgctc tatttccgcc tgctccgcca gcatggctgc    480
aacctgtcgt cggacatctt caacaagttc aagaaggaag gcggcggctt caaggcctcg    540
ctctgcgagg acgccatggg cctgctctcg ctgtatgagg ccgtgcgcct ctcggtgaag    600
```

```
ggcgaggcca tcctggagga agcccaggtg ttctcgatcg ccaacctgaa gatcctcatg     660

gagcgcgtgg agcgcaagct cgccgaccgc atcgagcatg ccctggagat cccgctctat     720

tggcgcgccc cgcgtctgga ggcccgctgg tacatcgacg tgtatgagaa ggaagacggc     780

cgcatcgacg acctgctcga cttcgcgaag ctggacttca accgcgtgca gatgctctat     840

cagaccgagc tgaaggagct ctcgatgtgg tgggagctgc tgggcctgcc cgccaagatg     900

ggcttcttcc gcgaccgcct gctcgagaac cacctcttct cgatcgccgt ggtggtggag     960

ccccagtact cgcagtgccg cgtggccatc accaaggcga tcgtgctgat gacggcgatg    1020

gacgacttct atgacgtgca tggcctgccg gacgagctca aggtgttcac cgacacggtg    1080

aaccgctggg acctggaggg catcgaccag ctccccgagt acatgaagct gtactatctg    1140

gcgctctaca acaccacgaa cgagacggcc tatatcatcc tgaaggagaa gggcttcaac    1200

gccacgcatt acctgaagaa gctctgggcc atgcagtcga acgcgtattt ccgcgaggcc    1260

cagtggttca actcgggcta catcccgaag ttcgacgagt atctggacaa cgccctcgtg    1320

tcggtgggcg ccccgttcgt gctgggcctc tcgtatccca tgatccagca gcagatctcg    1380

aaggaagaga tcgacctgat ccccgaggac ctcaacctgc tccgctgggc ctcgatcatc    1440

ttccgcctgt acgacgacct ggccacctcg aaggccgagc agcagcgcgg cgacgtgccc    1500

aagtcgatcc agtgctatat gcatgagacg ggctcgtcgg aggaagtggc ggccaaccat    1560

atccgcgacc tgatctcgga cgcgtggaag gaagtgaacg ccgagtgcct gaagccgacc    1620

tcgctctcga agcactacgt gggcgtggcc cccaactcgg cccgctcggg cgtgctcatg    1680

tatcaccatg acttcgacgg cttcgcgtcg ccccatggcc gcacgaacgc ccacatcacg    1740

agcatcttct tcgagccggt cccccctcaag gagagcatca acctgggctg a            1791
```

<210> SEQ ID NO 32
<211> LENGTH: 1048
<212> TYPE: PRT
<213> ORGANISM: artificial
<220> FEATURE:
<223> OTHER INFORMATION: NusA-CiCaSSy

<400> SEQUENCE: 32

```
Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45

Ile Asp Arg Lys Ser Gly Asp Phe Asp Thr Phe Arg Arg Trp Leu Val
    50                  55                  60

Val Asp Glu Val Thr Gln Pro Thr Lys Glu Ile Thr Leu Glu Ala Ala
65                  70                  75                  80

Arg Tyr Glu Asp Glu Ser Leu Asn Leu Gly Asp Tyr Val Glu Asp Gln
                85                  90                  95

Ile Glu Ser Val Thr Phe Asp Arg Ile Thr Thr Gln Thr Ala Lys Gln
            100                 105                 110

Val Ile Val Gln Lys Val Arg Glu Ala Glu Arg Ala Met Val Val Asp
        115                 120                 125

Gln Phe Arg Glu His Glu Gly Glu Ile Ile Thr Gly Val Val Lys Lys
    130                 135                 140

Val Asn Arg Asp Asn Ile Ser Leu Asp Leu Gly Asn Asn Ala Glu Ala
145                 150                 155                 160
```

```
Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
            180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
    210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
            260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
    290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
            340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
    370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
            420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
    450                 455                 460

Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Met
                485                 490                 495

Asp Ser Met Glu Val Arg Arg Ser Ala Ile Tyr His Ser Thr Phe Trp
            500                 505                 510

Asp Ile Asp Ser Ile Arg Ala Leu Leu Ala Arg Arg Asp Cys Thr Ala
        515                 520                 525

Ala Ala Ala Leu Ser Pro Asp His His Lys Arg Leu Lys Glu Arg Ile
    530                 535                 540

Gln Arg Arg Leu Gln Asp Ile Thr Gln Pro His His Leu Leu Gly Leu
545                 550                 555                 560

Ile Asp Ala Val Gln Arg Leu Gly Val Ala Tyr Gln Phe Glu Glu Glu
                565                 570                 575
```

```
Ile Ser Asp Ala Leu His Gly Leu His Ser Glu Asn Thr Glu His Ala
            580                 585                 590

Ile Lys Asp Ser Leu His His Thr Ser Leu Tyr Phe Arg Leu Leu Arg
        595                 600                 605

Gln His Gly Cys Asn Leu Ser Ser Asp Ile Phe Asn Lys Phe Lys Lys
    610                 615                 620

Glu Gly Gly Gly Phe Lys Ala Ser Leu Cys Glu Asp Ala Met Gly Leu
625                 630                 635                 640

Leu Ser Leu Tyr Glu Ala Val Arg Leu Ser Val Lys Gly Glu Ala Ile
                645                 650                 655

Leu Glu Glu Ala Gln Val Phe Ser Ile Ala Asn Leu Lys Ile Leu Met
            660                 665                 670

Glu Arg Val Glu Arg Lys Leu Ala Asp Arg Ile Glu His Ala Leu Glu
        675                 680                 685

Ile Pro Leu Tyr Trp Arg Ala Pro Arg Leu Glu Ala Arg Trp Tyr Ile
    690                 695                 700

Asp Val Tyr Glu Lys Glu Asp Gly Arg Ile Asp Asp Leu Leu Asp Phe
705                 710                 715                 720

Ala Lys Leu Asp Phe Asn Arg Val Gln Met Leu Tyr Gln Thr Glu Leu
                725                 730                 735

Lys Glu Leu Ser Met Trp Trp Glu Leu Leu Gly Leu Pro Ala Lys Met
            740                 745                 750

Gly Phe Phe Arg Asp Arg Leu Leu Glu Asn His Leu Phe Ser Ile Ala
        755                 760                 765

Val Val Val Glu Pro Gln Tyr Ser Gln Cys Arg Val Ala Ile Thr Lys
    770                 775                 780

Ala Ile Val Leu Met Thr Ala Met Asp Asp Phe Tyr Asp Val His Gly
785                 790                 795                 800

Leu Pro Asp Glu Leu Lys Val Phe Thr Asp Thr Val Asn Arg Trp Asp
                805                 810                 815

Leu Glu Gly Ile Asp Gln Leu Pro Glu Tyr Met Lys Leu Tyr Tyr Leu
            820                 825                 830

Ala Leu Tyr Asn Thr Thr Asn Glu Thr Ala Tyr Ile Ile Leu Lys Glu
        835                 840                 845

Lys Gly Phe Asn Ala Thr His Tyr Leu Lys Lys Leu Trp Ala Met Gln
    850                 855                 860

Ser Asn Ala Tyr Phe Arg Glu Ala Gln Trp Phe Asn Ser Gly Tyr Ile
865                 870                 875                 880

Pro Lys Phe Asp Glu Tyr Leu Asp Asn Ala Leu Val Ser Val Gly Ala
                885                 890                 895

Pro Phe Val Leu Gly Leu Ser Tyr Pro Met Ile Gln Gln Gln Ile Ser
            900                 905                 910

Lys Glu Glu Ile Asp Leu Ile Pro Glu Asp Leu Asn Leu Leu Arg Trp
        915                 920                 925

Ala Ser Ile Ile Phe Arg Leu Tyr Asp Asp Leu Ala Thr Ser Lys Ala
    930                 935                 940

Glu Gln Gln Arg Gly Asp Val Pro Lys Ser Ile Gln Cys Tyr Met His
945                 950                 955                 960

Glu Thr Gly Ser Ser Glu Glu Val Ala Ala Asn His Ile Arg Asp Leu
                965                 970                 975

Ile Ser Asp Ala Trp Lys Glu Val Asn Ala Glu Cys Leu Lys Pro Thr
            980                 985                 990
```

```
Ser Leu Ser Lys His Tyr Val Gly  Val Ala Pro Asn Ser  Ala Arg Ser
        995                 1000                 1005

Gly Val  Leu Met Tyr His His  Asp Phe Asp Gly Phe  Ala Ser Pro
    1010                 1015                 1020

His Gly  Arg Thr Asn Ala His  Ile Thr Ser Ile Phe  Phe Glu Pro
    1025                 1030                 1035

Val Pro  Leu Lys Glu Ser Ile  Asn Leu Gly
    1040                 1045


<210> SEQ ID NO 33
<211> LENGTH: 594
<212> TYPE: PRT
<213> ORGANISM: artificial
<220> FEATURE:
<223> OTHER INFORMATION: SET-CiCaSSy

<400> SEQUENCE: 33

Met Glu Glu Ala Ser Val Thr Ser Thr Glu Glu Thr Leu Thr Pro Ala
1               5                   10                  15

Gln Glu Ala Ala Arg Thr Arg Ala Ala Asn Lys Ala Arg Lys Glu Ala
            20                  25                  30

Glu Leu Ala Ala Ala Thr Ala Glu Gln Met Asp Ser Met Glu Val Arg
        35                  40                  45

Arg Ser Ala Ile Tyr His Ser Thr Phe Trp Asp Ile Asp Ser Ile Arg
    50                  55                  60

Ala Leu Leu Ala Arg Arg Asp Cys Thr Ala Ala Ala Ala Leu Ser Pro
65                  70                  75                  80

Asp His His Lys Arg Leu Lys Glu Arg Ile Gln Arg Arg Leu Gln Asp
                85                  90                  95

Ile Thr Gln Pro His His Leu Leu Gly Leu Ile Asp Ala Val Gln Arg
            100                 105                 110

Leu Gly Val Ala Tyr Gln Phe Glu Glu Glu Ile Ser Asp Ala Leu His
        115                 120                 125

Gly Leu His Ser Glu Asn Thr Glu His Ala Ile Lys Asp Ser Leu His
    130                 135                 140

His Thr Ser Leu Tyr Phe Arg Leu Leu Arg Gln His Gly Cys Asn Leu
145                 150                 155                 160

Ser Ser Asp Ile Phe Asn Lys Phe Lys Lys Glu Gly Gly Gly Phe Lys
                165                 170                 175

Ala Ser Leu Cys Glu Asp Ala Met Gly Leu Leu Ser Leu Tyr Glu Ala
            180                 185                 190

Val Arg Leu Ser Val Lys Gly Glu Ala Ile Leu Glu Glu Ala Gln Val
        195                 200                 205

Phe Ser Ile Ala Asn Leu Lys Ile Leu Met Glu Arg Val Glu Arg Lys
    210                 215                 220

Leu Ala Asp Arg Ile Glu His Ala Leu Glu Ile Pro Leu Tyr Trp Arg
225                 230                 235                 240

Ala Pro Arg Leu Glu Ala Arg Trp Tyr Ile Asp Val Tyr Glu Lys Glu
                245                 250                 255

Asp Gly Arg Ile Asp Asp Leu Leu Asp Phe Ala Lys Leu Asp Phe Asn
            260                 265                 270

Arg Val Gln Met Leu Tyr Gln Thr Glu Leu Lys Glu Leu Ser Met Trp
        275                 280                 285

Trp Glu Leu Leu Gly Leu Pro Ala Lys Met Gly Phe Phe Arg Asp Arg
    290                 295                 300
```

-continued

```
Leu Leu Glu Asn His Leu Phe Ser Ile Ala Val Val Val Glu Pro Gln
305                 310                 315                 320

Tyr Ser Gln Cys Arg Val Ala Ile Thr Lys Ala Ile Val Leu Met Thr
                325                 330                 335

Ala Met Asp Asp Phe Tyr Asp Val His Gly Leu Pro Asp Glu Leu Lys
            340                 345                 350

Val Phe Thr Asp Thr Val Asn Arg Trp Asp Leu Glu Gly Ile Asp Gln
        355                 360                 365

Leu Pro Glu Tyr Met Lys Leu Tyr Tyr Leu Ala Leu Tyr Asn Thr Thr
    370                 375                 380

Asn Glu Thr Ala Tyr Ile Ile Leu Lys Glu Lys Gly Phe Asn Ala Thr
385                 390                 395                 400

His Tyr Leu Lys Lys Leu Trp Ala Met Gln Ser Asn Ala Tyr Phe Arg
                405                 410                 415

Glu Ala Gln Trp Phe Asn Ser Gly Tyr Ile Pro Lys Phe Asp Glu Tyr
            420                 425                 430

Leu Asp Asn Ala Leu Val Ser Val Gly Ala Pro Phe Val Leu Gly Leu
        435                 440                 445

Ser Tyr Pro Met Ile Gln Gln Gln Ile Ser Lys Glu Glu Ile Asp Leu
    450                 455                 460

Ile Pro Glu Asp Leu Asn Leu Leu Arg Trp Ala Ser Ile Ile Phe Arg
465                 470                 475                 480

Leu Tyr Asp Asp Leu Ala Thr Ser Lys Ala Glu Gln Gln Arg Gly Asp
                485                 490                 495

Val Pro Lys Ser Ile Gln Cys Tyr Met His Glu Thr Gly Ser Ser Glu
            500                 505                 510

Glu Val Ala Ala Asn His Ile Arg Asp Leu Ile Ser Asp Ala Trp Lys
        515                 520                 525

Glu Val Asn Ala Glu Cys Leu Lys Pro Thr Ser Leu Ser Lys His Tyr
    530                 535                 540

Val Gly Val Ala Pro Asn Ser Ala Arg Ser Gly Val Leu Met Tyr His
545                 550                 555                 560

His Asp Phe Asp Gly Phe Ala Ser Pro His Gly Arg Thr Asn Ala His
                565                 570                 575

Ile Thr Ser Ile Phe Phe Glu Pro Val Pro Leu Lys Glu Ser Ile Asn
            580                 585                 590

Leu Gly
```